United States Patent
Fehr et al.

(10) Patent No.: US 10,138,515 B2
(45) Date of Patent: Nov. 27, 2018

(54) ILLUMINATION OF INTEGRATED ANALYTICAL SYSTEMS

(71) Applicant: Pacific Biosciences of California, Inc., Menlo Park, CA (US)

(72) Inventors: Adrian Fehr, San Francisco, CA (US); Nathaniel Joseph McCaffrey, Mill Valley, CA (US); Stephen Turner, Seattle, WA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 206 days.

(21) Appl. No.: 14/844,492

(22) Filed: Sep. 3, 2015

(65) Prior Publication Data
US 2016/0069806 A1  Mar. 10, 2016

Related U.S. Application Data

(63) Continuation of application No. 13/895,486, filed on May 16, 2013, now Pat. No. 9,157,864, which is a (Continued)

(51) Int. Cl.
*C12Q 1/68* (2018.01)
*C12Q 1/6874* (2018.01)
(Continued)

(52) U.S. Cl.
CPC ...... *C12Q 1/6874* (2013.01); *B01L 3/502707* (2013.01); *B01L 3/502715* (2013.01);
(Continued)

(58) Field of Classification Search
None
See application file for complete search history.

(56) References Cited

U.S. PATENT DOCUMENTS

| 4,818,710 A | 4/1989 | Sutherland et al. |
| 5,082,629 A | 1/1992 | Burgess, Jr. et al. |

(Continued)

FOREIGN PATENT DOCUMENTS

| EP | 1229133 A2 | 8/2002 |
| EP | 1105529 B1 | 11/2005 |

(Continued)

OTHER PUBLICATIONS

EP 14191733.6, Feb. 7, 2017, Examination Report.
(Continued)

*Primary Examiner* — Betty J Forman
(74) *Attorney, Agent, or Firm* — Morgan, Lewis & Bockius LLP

(57) ABSTRACT

An analytical device including an optically opaque cladding, a sequencing layer including a substrate disposed below the cladding, and a waveguide assembly for receiving optical illumination and introducing illumination into the device. The illumination may be received from a top, a side edge, and a bottom of the device. The waveguide assembly may include a nanoscale aperture disposed in the substrate and extending through the cladding. The aperture defines a reaction cell for receiving a set of reactants. In various aspects, the device includes a sensor element and the illumination pathway is through the sensor element. Waveguides and illumination devices, such as plasmonic illumination devices, are also disclosed. Methods for forming and operating the devices are also disclosed.

15 Claims, 45 Drawing Sheets

Related U.S. Application Data continuation of application No. 13/031,103, filed on Feb. 18, 2011, now Pat. No. 8,465,699.

(60) Provisional application No. 61/306,235, filed on Feb. 19, 2010, provisional application No. 61/387,916, filed on Sep. 29, 2010, provisional application No. 61/410,189, filed on Nov. 4, 2010.

(51) Int. Cl.

| | | |
|---|---|---|
| *B01L 3/00* | (2006.01) | |
| *G01N 21/64* | (2006.01) | |
| *G01N 21/75* | (2006.01) | |
| *B82Y 20/00* | (2011.01) | |
| *G01N 33/543* | (2006.01) | |
| *G02B 6/122* | (2006.01) | |
| *G01N 21/03* | (2006.01) | |
| *G01N 21/05* | (2006.01) | |
| *G01N 21/77* | (2006.01) | |
| *C12Q 1/6825* | (2018.01) | |
| *C12Q 1/6869* | (2018.01) | |

(52) U.S. Cl.
CPC ............ *B82Y 20/00* (2013.01); *C12Q 1/6825* (2013.01); *C12Q 1/6869* (2013.01); *G01N 21/03* (2013.01); *G01N 21/0303* (2013.01); *G01N 21/05* (2013.01); *G01N 21/64* (2013.01); *G01N 21/645* (2013.01); *G01N 21/648* (2013.01); *G01N 21/6428* (2013.01); *G01N 21/6452* (2013.01); *G01N 21/6456* (2013.01); *G01N 21/75* (2013.01); *G01N 21/77* (2013.01); *G01N 33/54373* (2013.01); *G02B 6/1226* (2013.01); *B01L 2300/0654* (2013.01); *B01L 2300/0663* (2013.01); *B01L 2300/0816* (2013.01); *B01L 2300/168* (2013.01); *G01N 2021/0346* (2013.01); *G01N 2021/6434* (2013.01); *G01N 2021/6439* (2013.01); *G01N 2021/6441* (2013.01); *G01N 2021/6463* (2013.01); *G01N 2021/757* (2013.01); *G01N 2021/7786* (2013.01); *G01N 2201/067* (2013.01); *G01N 2201/068* (2013.01); *G01N 2201/08* (2013.01); *Y10T 436/143333* (2015.01)

(56) References Cited

U.S. PATENT DOCUMENTS

| | | |
|---|---|---|
| 5,094,517 A | 3/1992 | Franke |
| 5,157,262 A | 10/1992 | Marsoner et al. |
| 5,159,661 A | 10/1992 | Ovshinsky et al. |
| 5,173,747 A | 12/1992 | Boiarski et al. |
| 5,192,502 A | 3/1993 | Attridge et al. |
| 5,233,673 A | 8/1993 | Vali et al. |
| 5,239,178 A | 8/1993 | Derndinger et al. |
| 5,439,647 A | 8/1995 | Saini |
| 5,446,534 A | 8/1995 | Goldman |
| 5,470,710 A | 11/1995 | Weiss et al. |
| 5,545,531 A | 8/1996 | Rava et al. |
| 5,578,832 A | 11/1996 | Trulson et al. |
| 5,605,662 A | 2/1997 | Heller et al. |
| 5,631,734 A | 5/1997 | Stern et al. |
| 5,677,196 A | 10/1997 | Herron et al. |
| 5,695,934 A | 12/1997 | Brenner |
| 5,744,305 A | 4/1998 | Fodor et al. |
| 5,812,709 A | 9/1998 | Arai et al. |
| 5,821,058 A | 10/1998 | Smith et al. |
| 5,832,165 A | 11/1998 | Reichert et al. |
| 5,867,266 A | 2/1999 | Craighead et al. |
| 5,919,712 A | 7/1999 | Herron et al. |
| 6,051,380 A | 4/2000 | Sosnowski et al. |
| 6,071,748 A | 6/2000 | Modlin et al. |
| 6,192,168 B1 | 2/2001 | Feldstein et al. |
| 6,198,869 B1 | 3/2001 | Kraus et al. |
| 6,210,896 B1 | 4/2001 | Chan |
| 6,236,945 B1 | 5/2001 | Simpson et al. |
| 6,263,286 B1 | 7/2001 | Gilmanshin et al. |
| 6,325,977 B1 | 12/2001 | Theil |
| 6,331,441 B1 | 12/2001 | Balch et al. |
| 6,384,912 B2 | 5/2002 | Kraus et al. |
| 6,388,788 B1 | 5/2002 | Harris et al. |
| 6,437,345 B1 | 8/2002 | Bruno-Raimondi et al. |
| 6,438,279 B1 | 8/2002 | Craighead et al. |
| 6,483,096 B1 | 11/2002 | Kunz et al. |
| 6,498,666 B1 | 12/2002 | Asghari |
| 6,545,758 B1 | 4/2003 | Sandstrom |
| 6,573,089 B1 | 6/2003 | Vann |
| 6,603,537 B1 | 8/2003 | Dietz et al. |
| 6,611,634 B2 | 8/2003 | Herron et al. |
| 6,633,659 B1 | 10/2003 | Zhou |
| 6,690,002 B2 | 2/2004 | Kuroda et al. |
| 6,692,697 B1 | 2/2004 | Melendez |
| 6,699,655 B2 | 3/2004 | Nikiforov et al. |
| 6,784,982 B1 | 8/2004 | Blumenfeld et al. |
| 6,800,860 B2 | 10/2004 | Dietz et al. |
| 6,818,395 B1 | 11/2004 | Quake et al. |
| 6,867,851 B2 | 3/2005 | Blumenfeld et al. |
| 6,917,726 B2 | 7/2005 | Levene et al. |
| 6,919,211 B1 | 7/2005 | Fodor et al. |
| 6,979,830 B2 | 12/2005 | Dietz et al. |
| 6,982,146 B1 | 1/2006 | Schneider et al. |
| 7,056,661 B2 | 6/2006 | Korlach et al. |
| 7,057,832 B2 | 6/2006 | Wu et al. |
| 7,075,695 B2 | 7/2006 | Gronbach |
| 7,081,954 B2 | 7/2006 | Sandstrom |
| 7,083,914 B2 | 8/2006 | Seul et al. |
| 7,130,041 B2 | 10/2006 | Bouzid et al. |
| 7,135,667 B2 | 11/2006 | Oldham et al. |
| 7,139,074 B2 | 11/2006 | Reel |
| 7,145,645 B2 | 12/2006 | Blumenfeld et al. |
| 7,150,997 B2 | 12/2006 | Kovacs |
| 7,175,811 B2 | 2/2007 | Bach et al. |
| 7,181,122 B1 | 2/2007 | Levene et al. |
| 7,189,361 B2 | 3/2007 | Carson |
| 7,197,196 B2 | 3/2007 | Lin et al. |
| 7,199,357 B1 | 4/2007 | Oldham et al. |
| 7,209,836 B1 | 4/2007 | Schermer et al. |
| 7,227,128 B2 | 6/2007 | Sagatelyan |
| 7,248,771 B2 | 7/2007 | Schmidt et al. |
| RE39,772 E | 8/2007 | Herron et al. |
| 7,271,896 B2 | 9/2007 | Chan et al. |
| 7,302,149 B2 | 11/2007 | Turner et al. |
| 7,302,348 B2 | 11/2007 | Ghosh et al. |
| 7,315,019 B2 | 1/2008 | Turner et al. |
| 7,323,681 B1 | 1/2008 | Oldham et al. |
| 7,385,460 B1 | 6/2008 | Wang et al. |
| 7,400,380 B2 | 7/2008 | Hahn |
| 7,443,489 B2 | 10/2008 | Natan |
| 7,476,504 B2 * | 1/2009 | Turner ................. B01L 3/5085 435/287.2 |
| 7,486,865 B2 | 2/2009 | Foque et al. |
| 7,501,241 B2 | 3/2009 | Matsushita et al. |
| 7,539,366 B1 | 5/2009 | Baks et al. |
| 7,626,704 B2 | 12/2009 | Lundquist et al. |
| 7,630,063 B2 | 12/2009 | Padmanabhan et al. |
| 7,630,073 B2 | 12/2009 | Lundquist et al. |
| 7,709,808 B2 | 5/2010 | Reel et al. |
| 7,767,441 B2 | 8/2010 | Chiou et al. |
| 7,811,810 B2 | 10/2010 | Chiou et al. |
| 7,820,983 B2 | 10/2010 | Lundquist et al. |
| 8,053,742 B2 * | 11/2011 | Lundquist .......... G01N 21/6452 250/458.1 |
| 8,247,216 B2 | 8/2012 | Zaccarin et al. |
| 8,748,947 B2 | 6/2014 | Milgrew |
| 9,096,898 B2 | 8/2015 | Williams et al. |
| 9,551,030 B2 * | 1/2017 | Turner ................. C12Q 1/6874 |
| 2001/0041025 A1 | 11/2001 | Farahi |
| 2002/0034457 A1 | 3/2002 | Reichert et al. |
| 2002/0094147 A1 | 7/2002 | Herron et al. |
| 2002/0110839 A1 | 8/2002 | Bach et al. |

(56) References Cited

U.S. PATENT DOCUMENTS

| | | |
|---|---|---|
| 2002/0113213 A1 | 8/2002 | Amirkhanian et al. |
| 2002/0146047 A1 | 10/2002 | Bendett et al. |
| 2002/0155592 A1 | 10/2002 | Kelleher et al. |
| 2003/0044781 A1 | 3/2003 | Korlach et al. |
| 2003/0132406 A1 | 7/2003 | Waldhausl et al. |
| 2003/0133681 A1 | 7/2003 | Bozhevolnyi |
| 2003/0138180 A1 | 7/2003 | Kondo |
| 2003/0174324 A1 | 9/2003 | Sandstrom |
| 2003/0174992 A1 | 9/2003 | Levene et al. |
| 2003/0201462 A1 | 10/2003 | Pommer et al. |
| 2003/0210399 A1 | 11/2003 | Bahatt et al. |
| 2003/0214057 A1 | 11/2003 | Huang |
| 2004/0040868 A1 | 3/2004 | Denuzzio et al. |
| 2004/0046128 A1 | 3/2004 | Abel et al. |
| 2004/0197793 A1 | 10/2004 | Hassibi et al. |
| 2004/0234417 A1 | 11/2004 | Schienle et al. |
| 2004/0249227 A1 | 12/2004 | Klapproth et al. |
| 2005/0014178 A1 | 1/2005 | Holm-Kennedy |
| 2005/0089993 A1 | 4/2005 | Boccazzi |
| 2005/0110989 A1 | 5/2005 | Schermer et al. |
| 2005/0135974 A1 | 6/2005 | Harvey et al. |
| 2005/0175273 A1 | 8/2005 | Iida et al. |
| 2005/0201899 A1 | 9/2005 | Weisbuch |
| 2005/0206895 A1 | 9/2005 | Salmelainen |
| 2006/0060766 A1 | 3/2006 | Turner et al. |
| 2006/0088818 A1 | 4/2006 | Beynon et al. |
| 2006/0098927 A1 | 5/2006 | Schmidt et al. |
| 2006/0103850 A1 | 5/2006 | Alphonse et al. |
| 2006/0183145 A1* | 8/2006 | Turner .................. B01L 3/5085 435/6.12 |
| 2006/0251371 A1 | 11/2006 | Schmidt et al. |
| 2006/0252070 A1 | 11/2006 | Boege et al. |
| 2006/0273245 A1 | 12/2006 | Kim et al. |
| 2007/0036511 A1 | 2/2007 | Lundquist et al. |
| 2007/0099212 A1 | 5/2007 | Harris |
| 2007/0146701 A1 | 6/2007 | Kiesel et al. |
| 2007/0188746 A1 | 8/2007 | Kraus et al. |
| 2007/0196815 A1 | 8/2007 | Lappe et al. |
| 2007/0279727 A1 | 12/2007 | Gandhi et al. |
| 2007/0281288 A1 | 12/2007 | Belkin et al. |
| 2008/0013877 A1 | 1/2008 | Schmidt et al. |
| 2008/0020938 A1 | 1/2008 | Kaplan |
| 2008/0037008 A1* | 2/2008 | Shepard ............. G01N 21/6408 356/73 |
| 2008/0039339 A1 | 2/2008 | Hassibi |
| 2008/0062290 A1 | 3/2008 | Lahav et al. |
| 2008/0081769 A1 | 4/2008 | Hassibi |
| 2008/0117421 A1 | 5/2008 | Yamaguchi et al. |
| 2008/0152280 A1 | 6/2008 | Lundquist |
| 2008/0161195 A1 | 7/2008 | Turner et al. |
| 2008/0212960 A1 | 9/2008 | Lundquist |
| 2008/0220537 A1 | 9/2008 | Foquet |
| 2008/0240543 A1 | 10/2008 | Budach et al. |
| 2008/0241866 A1 | 10/2008 | Korlach et al. |
| 2008/0260577 A1* | 10/2008 | Shirai ............... B01L 3/502761 422/52 |
| 2008/0308888 A1 | 12/2008 | Lee |
| 2009/0139576 A1 | 6/2009 | Crenshaw |
| 2009/0146076 A1 | 6/2009 | Chiou et al. |
| 2009/0181396 A1* | 7/2009 | Luong ................ G01N 21/6428 435/6.11 |
| 2009/0195784 A1 | 8/2009 | Ogura et al. |
| 2009/0247414 A1 | 10/2009 | Obradovic et al. |
| 2009/0253130 A1 | 10/2009 | Yoo et al. |
| 2009/0296188 A1 | 12/2009 | Jain et al. |
| 2009/0298075 A1 | 12/2009 | Travers et al. |
| 2009/0311774 A1 | 12/2009 | Chiou et al. |
| 2009/0321244 A1 | 12/2009 | Smith et al. |
| 2009/0323014 A1 | 12/2009 | Cunningham et al. |
| 2010/0009872 A1 | 1/2010 | Eid et al. |
| 2010/0065726 A1* | 3/2010 | Zhong .................. G01N 21/648 250/227.24 |
| 2010/0111475 A1 | 5/2010 | Lu et al. |
| 2010/0121582 A1 | 5/2010 | Pan et al. |
| 2010/0173394 A1 | 7/2010 | Colston et al. |
| 2010/0243449 A1 | 10/2010 | Oliver |
| 2010/0256918 A1 | 10/2010 | Chen et al. |
| 2011/0079704 A1 | 4/2011 | Yu et al. |
| 2011/0117637 A1 | 5/2011 | Gray et al. |
| 2011/0183320 A1 | 7/2011 | Flusberg et al. |
| 2011/0201099 A1 | 8/2011 | Anderson et al. |
| 2011/0210094 A1 | 9/2011 | Gray et al. |
| 2012/0014837 A1 | 1/2012 | Fehr et al. |

FOREIGN PATENT DOCUMENTS

| | | |
|---|---|---|
| EP | 1871902 B1 | 10/2006 |
| EP | 2362209 A2 | 8/2011 |
| FR | 2783919 A1 | 3/2000 |
| KR | 10-2005-0088782 A | 9/2005 |
| WO | WO 1991/006678 A1 | 5/1991 |
| WO | WO 2001/003833 A1 | 1/2001 |
| WO | WO 2001/016375 A2 | 3/2001 |
| WO | WO 2004/100068 A2 | 11/2004 |
| WO | WO 2006/116726 A2 | 2/2006 |
| WO | WO 2006/135782 A2 | 12/2006 |
| WO | WO 2007/002367 A2 | 1/2007 |
| WO | WO 2007/011549 A1 | 1/2007 |
| WO | WO 20081002765 A2 | 1/2008 |
| WO | WO 2009/001988 A1 | 12/2008 |
| WO | WO 2009/056065 A1 | 5/2009 |
| WO | WO 2009/131535 A1 | 10/2009 |
| WO | WO 2009/149125 A2 | 12/2009 |
| WO | WO 2010/009543 A1 | 1/2010 |
| WO | WO 2010/051773 A1 | 5/2010 |
| WO | WO 2010/102567 A1 | 9/2010 |
| WO | WO 2010/115147 A2 | 10/2010 |
| WO | WO 2011/076132 A2 | 6/2011 |

OTHER PUBLICATIONS

Bernini et al., "Polymer-on-glass waveguide structure for efficient fluorescence-based optical biosensors" Proc. SPIE (2005) 5728:101-111.

Boiarski et al., "Integrated-optic sensor with macro-flow cell" Proc. SPIE (1992) 1793:199-211.

Budach et al., "Planar waveguides as high-performance sensing platforms for fluorescence-based multiplexed oligonucleotide hybridization assays" Anal. Chem. (1999) 71(16):3347-3355.

Cottier et al., "Thickness-modulated waveguides for integrated optical sensing" Proc. SPIE (2002) 4616:53-63.

Deopura, M. et al., "Dielectric omnidirectional visible reflector" Optics Lett (2001) 26(15):1197-1199.

Duveneck et al., "Planar waveguides for ultra-high sensitivity of the analysis of nucleic acids" Anal Chem Acta (2002) 469:49-61.

Eid, J., et al., "Real-Time DNA Sequencing from Single Polymerase Molecules," Science, vol. 323, p. 133-138 (Jan. 2, 2009).

Feldstein et al., "Array Biosensor: optical and fluidics systems" J. Biomed Microdev. (1999) 1:139-153.

Fink, Y. et al., "A dielectric omnidirectional reflector" Science (1998) 282:1679-1682.

Gupta, P. "Single-Molecule DNA Sequencing Technologies for Future Genomics Research," Trends in Biotechnology, vol. 26, No. 11, p. 602-611.

Han, K.-H., et al., "An Active Microfluidic System Packaging Technology", Sensors and Actuators B 122, p. 337-346, 2007.

Herron et al., "Orientation and Activity of Immobilized Antibodies" Biopolymers at Interfaces 2nd Ed (2003) Surfactant Science Series vol. 110, Marcel Dekker, NY pp. 115-163.

Kumbhakar, M. "Single-Molecule Detection in Exploring Nanoenvironments: an Overview," J. of Photochemistry and Photobiology, n. 5, p. 113-137 (2004).

Levene, M.J. et al., "Zero-mode waveguides for single-molecule analysis at high concentrations" Science (2003) 299:682-686.

Ottesen et al., "Microfluidic Digital PCR Enables Multigene Analysis of Individual Environmental Bacteria," Science, 2006, v. 314, p. 1464.

(56) References Cited

OTHER PUBLICATIONS

Psaltis, Demetri, et al., "Developing Optofluidic Technology through the Fusion of Microfluidics and Optics," Nature, v. 442, p. 381-386, Jul. 27, 2006.
Salama et al., "Modeling and simulations of luminescence detection platforms" Biosensors & Bioelectronics (2004) 19:1377-1386.
Satoh, et al., "On-Chip Microfluidic Transport and Bio/Chemical Sensing Bsaed on Electrochemical Bubble Formation", Sensors and Actuators B 123, p. 1153-1160, 2007.
Wang, et al., "Generation of Radially and Azimuthally Polarized Light by Optical Transmission Through Concentric Circular Nanoslits in AG Films," Optics Express, 2010, vol. 18, issue 1, 63-71.
Weissman et al., "Mach-Zhnder type, evanescent-wave bio-sensor, in ion-exchanged glass, using periodically segmented waveguide" Proc. Spie (1999) 3596:210-216.
Wu et al., "DNA and protein microarray printing on silicon nitride waveguide surfaces" Biosensors and Bioelectronics (2006) 21:1252-1263.
Yang, Z. et al., "A World-to-Chip Socket for Microfluidic Prototype Development" Electrophoresis, v. 23, p. 3474-3478, Jan. 1, 2002.
Yang, Z. et al., "Socket with Built-In Valves for the Interconnection of Microfluidic Chips to Macro Constituents", J. of Chromatography, v. 1013, No. 1-2, p. 29-33, Sep. 26, 2003.
Yariv, A. et al., "Periodic structures for integrated optics" IEEE J Quantum Elec (1977) QE-13(4):233-253.

\* cited by examiner

2-D single use micro-pipette array insert for clamshell package

Top view of photonic and fluidic ports on top half of durable ATE socket

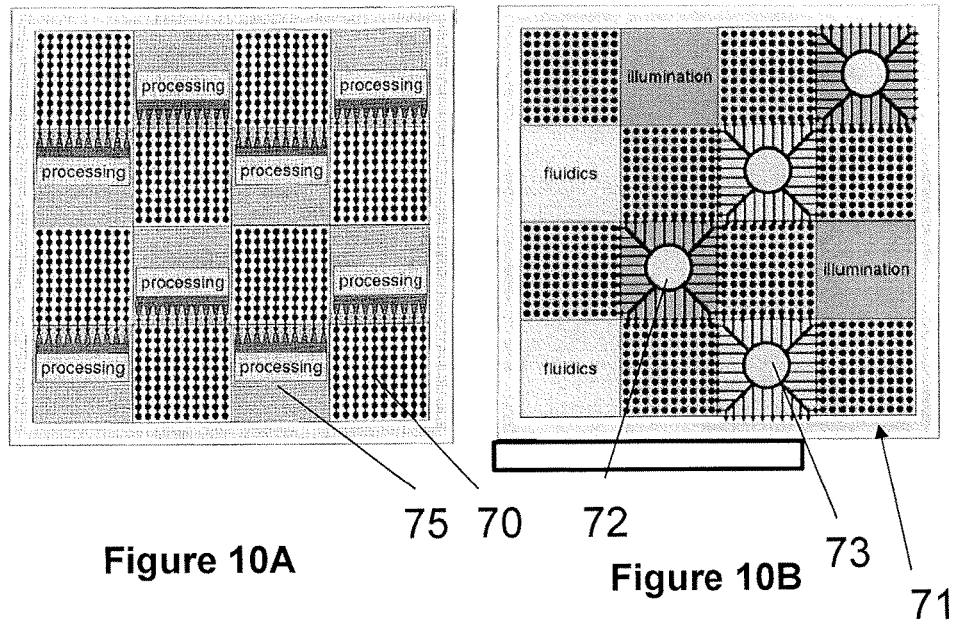
Figure 10A
Figure 10B
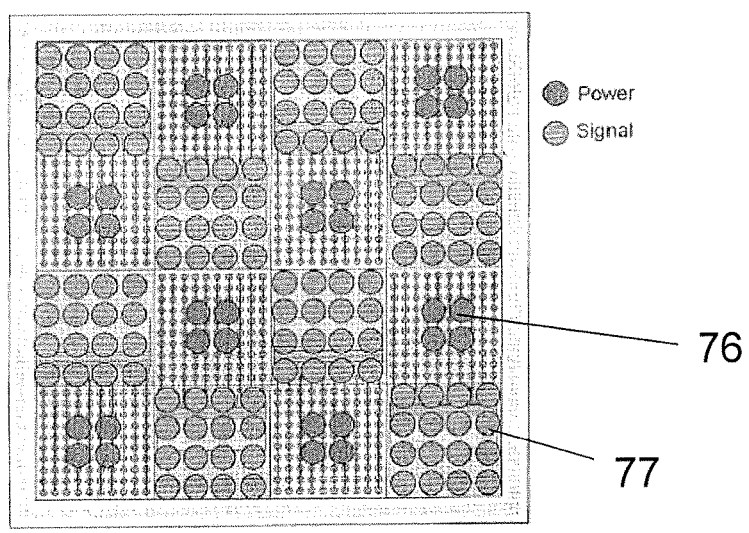
Figure 10C

MIM Structure for dual slab plasmon generation

ILLUMINATION OF INTEGRATED ANALYTICAL SYSTEMS

CROSS-REFERENCE TO RELATED APPLICATIONS

This application is a continuation of U.S. application Ser. No. 13/895,486 filed May 16, 2013 which is a continuation of U.S. application Ser. No. 13/031,103 filed Feb. 18, 2011 which claims priority to U.S. Provisional Application No. 61/306,235 filed Feb. 19, 2010 and entitled INTEGRATED ANALYTICAL DEVICES AND SYSTEMS, U.S. Provisional Patent Application No. 61/387,916 filed Sep. 29, 2010 and entitled INTEGRATED ANALYTICAL SYSTEM AND METHOD, and U.S. Provisional Patent Application No. 61/410,189 filed Nov. 4, 2010 and entitled ILLUMINATION OF INTEGRATED ANALYTICAL SYSTEMS, the entire contents of which applications is incorporated herein for all purposes by this reference.

STATEMENT REGARDING FEDERALLY SPONSORED RESEARCH

Not Applicable.

BACKGROUND OF THE INVENTION

Analytical technologies continue to advance far beyond the test tube scale evaluations of the $19^{th}$ and $20^{th}$ centuries, and have progressed to the point where researchers can look at very specific interactions in vivo, in vitro, at the cellular level, and even at the level of individual molecules. This progression is driven not just by the desire to understand important reactions in their purest form, but also by the realization that seemingly minor or insignificant reactions in living systems can prompt a cascade of other events that could potentially unleash a life or death result.

In this progression, these analyses not only have become more focused on lesser events, but also have had to become appropriately more sensitive in order to be able to monitor such reactions. In increasing sensitivity to the levels of cellular or even single molecular levels, one may inherently increase the sensitivity of the system to other non-relevant signals, or "noise." In some cases, the noise level can be of sufficient magnitude that it partially or completely obscures the desired signals, i.e., those corresponding to the analysis of interest. Accordingly, it is desirable to be able to increase sensitivity of detection while maintaining the signal-to-noise ratio.

A large number of systems for optical analysis of samples or materials employ complex optical trains that direct, focus, filter, split, separate and detect light to and/or from the sample materials. Such systems typically employ an assortment of different optical elements to direct, modify, and otherwise manipulate light directed to and/or received from a reaction site.

Conventional optical systems typically are complex and costly. The systems also tend to have significant space requirements. For example, typical systems employ mirrors and prisms in directing light (e.g. laser light) from its source to a desired destination. Additionally, such systems may include light splitting optics such as beam splitting prisms to generate two beams from a single original beam. In the case of modern analysis systems, there is a continuing need for systems with very high throughput and portability.

There is a continuing need for optical systems for creating more focused, localized excitation signals. For example, analytical systems for monitoring processes at the single molecule level show great promise but require illumination in a small volume. There is a need for delivering a focused optical signal with specific characteristics to achieve the desired affect (e.g. excitation of single particles of interest). There is a continuing need for illumination devices and analytical systems with reduced noise and improved performance.

There is a continuing need to improve upon the functionality, footprint and cost of systems for optical analysis. The present invention provides devices, systems, and methods for overcoming the above problems in addition to other benefits.

BRIEF SUMMARY OF THE INVENTION

The present invention is generally directed to an integrated analytical device for analyses of a sample. A variety of elements may be integrated into the device structure to enhance the performance and scalability of the device. Various aspects of the invention are directed to an analytical system employing an integrated analytical device and elements and methods for efficient integration.

Various aspects of the invention are directed to an analytical device including an optically opaque cladding layer, a sequencing layer including a substrate disposed below the cladding, and a waveguide assembly for receiving optical illumination and introducing illumination into the device. The illumination may be received from one of a top, a side edge, and/or a bottom of the device. The waveguide assembly may include a nanoscale aperture disposed in the substrate and extending through the cladding. The aperture defines a reaction cell for receiving a set of reactants.

Various aspects of the invention are directed to an analytical device including an optically opaque cladding layer, a sequencing layer, a sensor element disposed in optical communication with the at least one nanoscale aperture along a detection pathway, and a waveguide for receiving illumination and directing the illumination along an illumination pathway through the sensor element to the at least one nanoscale aperture for exciting a material of interest therein. The sequencing layer may include a transparent substrate disposed below the cladding and at least one nanoscale aperture extending through the cladding to a top of the substrate, each aperture separated from any other aperture by regions of the transparent substrate. In various embodiments, part or all of the detection pathway is essentially coextensive with and opposite the illumination pathway.

Various aspects of the invention are directed to a system for monitoring analytical reactions, the system including an analytical device having a nanoscale reaction cell housing a set of reactants, the set of reactants including an upconverting phosphor for receiving two or more photons of a first energy level and emitting fewer photons of a second energy level in response, the second energy level being greater than the first energy level.

Various aspects of the invention are directed to a device for exciting a fluorophore, the device including a first region having a reaction cell configured to receive a fluorophore, a second region laterally adjacent the first region, the second region including a metal-insulator-metal (MIM) structure for providing plasmonic energy to the reaction cell, a fourth region including an optical waveguide and inlet for receiving optical energy, and a third region operationally positioned between the second region and the fourth region. In various embodiments, the third region includes a transition portion at one end of the waveguide adjacent the MIM structure. In various embodiments, the transition portion is dimensioned and configured to direct the received optical energy to the MIM structure thereby exciting surface plasmon polaritons (SPP) that are applied to the reaction cell.

Various aspects of the invention are directed to methods for forming and operating the devices.

The methods and apparatuses of the present invention have other features and advantages which will be apparent from or are set forth in more detail in the accompanying drawings, which are incorporated herein, and the following Detailed Description of the Invention, which together serve to explain certain principles of the present invention.

BRIEF DESCRIPTION OF THE DRAWINGS

FIG. 10A-FIG. 10C show various layers in an optode array chip. FIG. 10A is a layer having detectors and processing components, FIG. 10B is a top view of the device showing distributed fluidics and illumination systems. FIG. 10C shows the bottom of the device having electrical contacts for connections with distributed power and signal systems.

DETAILED DESCRIPTION OF THE INVENTION

Figure 1:
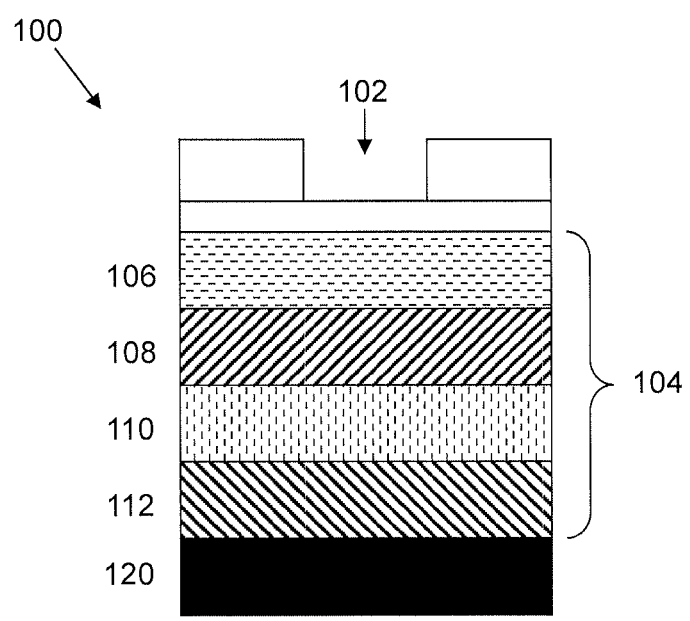
FIG. 1 is a block diagram of an optical analytical device architecture in accordance with the present invention.

Reference will now be made in detail to the various embodiments of the invention, examples of which are illustrated in the accompanying drawings. While the invention will be described in conjunction with the various embodiments, it will be understood that they are not intended to limit the invention to those embodiments. On the contrary, the invention is intended to cover alternatives, modifications and equivalents, which may be included within the spirit and scope of the invention as defined by the appended claims.

This application is related to U.S. Provisional Application No. 61/306,235, filed Feb. 19, 2010 and entitled INTEGRATED ANALYTICAL DEVICES AND SYSTEMS, the entire content of which is incorporated herein for all purposes by this reference.

I. Optical Analyses

The present invention is generally directed to improved systems, methods and devices for use in optical analyses, and particularly, optical analyses of biological and/or chemical samples and reactions. Various aspects of the invention are related to integrated devices and systems such as those described in U.S. Provisional Patent Application No. 61/387,916, entitled INTEGRATED ANALYTICAL SYSTEM AND METHOD and filed on Sep. 29, 2010.

In various respects, the optical analyses of the invention generally seek to gather and detect one or more optical signals, the appearance or disappearance of which, or localization of which, is indicative of a given chemical or biological reaction and/or the presence or absence of a given substance within a sample material. In some cases, reactants, their products, or substance of interest (all of which are referred to as reactants herein) inherently present an optically detectable signal which can be detected. In other cases, reactants are provided with exogenous labeling groups to facilitate their detection. Useful labeling groups include fluorescent labels, luminescent labels, mass labels, light scattering labels, electrochemical labels (e.g., carrying large charge groups), metal labels, and the like. Exemplars of such labeling groups are disclosed by U.S. Pat. No. 7,332,284 and U.S. Patent Publication Nos. 2009/0233302 filed Mar. 12, 2009, 2008/0241866 filed Mar. 27, 2008, and 2010/0167299 filed Nov. 17, 2009, the contents of which patents and applications are incorporated herein for all purposes by this reference.

In various embodiments, one or more reactants in an analysis is provided with a fluorescent labeling group that possesses a fluorescent emission spectrum that is shifted from its excitation spectrum, allowing discrimination between the excitation light source and the emission of the label group. These fluorescent labels typically have high quantum yields, further enhancing their detectability. A variety of different fluorescent label groups are well known in the art, and include fluorescein and rhodamine based organic dyes, such as those sold under the Cy3 and Cy5 labels from, e.g., GE Healthcare, and the AlexaFluor® dyes available from Life Technologies, Inc. A wide variety of organic dye structures have been previously described in the art.

Other fluorescent label groups include, for example, particle-based labeling groups. Some such particle label groups constitute encapsulated or otherwise entrained organic fluorophores, while others comprise fluorescent nanoparticles, such as inorganic semiconductor nanocrystals, e.g., as described in U.S. Pat. Nos. 6,207,392, 6,225,198, 6,251,303, 6,501,091, and 7,566,476, the full disclosures of which are incorporated herein by reference in their entirety for all purposes.

"Nano-scale" and "micro-scale" are to be understood as generally used in the analytical arts and physics. As used herein, however, the term "nano-scale" may include dimensions slightly larger or smaller than "nano-scale." In various respects, "nano" and "micro" are generally overlapping. For example, "nano-scale aperture" may refer to an aperture having dimensions on either the nano- or micro-scale. Similarly, "microfluidics" is not intended to limit the fluidic devices to the micro-scale. One will appreciate that the size and dimensions of the elements may vary depending on the application.

By detecting these fluorescent labeling groups, one can ascertain the localization of a given labeled reactant, or detect reaction events that result in changes in the spectral or other aspects of the fluorescently labeled reactant. For example, in binding or hybridization reactions, the ability of a labeled reactant to bind to another immobilized reactant is detected by contacting the reactants, washing unbound labeled reactant away, and observing the immobilized reactant to look for the presence of bound fluorescent label. Such assays are routinely employed in hybridization assays, antibody assays, and a variety of other analyses.

In a number of different nucleic acid sequencing analyses, fluorescently-labeled nucleotides are used to monitor the polymerase-mediated, template-dependent incorporation of nucleotides in a primer extension reaction. In particular, a labeled nucleotide is introduced to a primer template polymerase complex, and incorporation of the labeled nucleotide is detected. If a labeled nucleotide is incorporated, it is indicative of the underlying and complementary nucleotide in the sequence of the template molecule. In traditional Sanger sequencing processes, the detection of incorporation of labeled nucleotides utilizes a termination reaction where the labeled nucleotides carry a terminating group that blocks further extension of the primer. By mixing the labeled terminated nucleotides with unlabeled native nucleotides, one generates nested sets of fragments that terminate at different nucleotides. These fragments are then separated by capillary electrophoresis, to separate those fragments that differ by a single nucleotide, and the labels for the fragments are read in order of increasing fragment size to provide the sequence (as provided by the last-added, labeled terminated nucleotide). By providing a different fluorescent label on each of the types of nucleotides that are added, one can readily differentiate the different nucleotides in the sequence (e.g., U.S. Pat. No. 5,821,058, incorporated herein for all purposes by this reference).

In newer generation sequencing technologies, arrays of primer-template complexes are immobilized on surfaces of substrates such that individual molecules or individual and homogeneous groups of molecules are spatially discrete from other individual molecules or groups of molecules, respectively. Labeled nucleotides are added in a manner that results in a single nucleotide being added to each individual molecule or group of molecules. Following the addition of the nucleotide, the labeled addition is detected and identified.

In some cases, the processes utilize the addition of a single type of nucleotide at a time, followed by a washing step. The labeled nucleotides that are added are then detected, their labels removed, and the process repeated with a different nucleotide type. Sequences of individual template sequences are determined by the order of appearance of the labels at given locations on the substrate.

In other similar cases, the immobilized complexes are contacted with all four types of labeled nucleotides where each type bears a distinguishable fluorescent label and a terminator group that prevents the addition of more than one nucleotide in a given step. Following the single incorporation in each individual template sequence (or group of template sequences,) the unbound nucleotides are washed away, and the immobilized complexes are scanned to identify which nucleotide was added at each location. Repeating the process yields sequence information of each of the template sequences. In other cases, more than four types of labeled nucleotides are utilized.

In particularly elegant approaches, labeled nucleotides are detected during the incorporation process, in real time, by individual molecular complexes. Such methods are described, for example, in U.S. Pat. No. 7,056,661, which is incorporated herein by reference in its entirety for all purposes. In these processes, nucleotides are labeled on a terminal phosphate group that is released during the incorporation process so as to avoid accumulation of label on the extension product and avoid any need for label removal processes that can be deleterious to the complexes. Primer/template polymerase complexes are observed during the polymerization process, and nucleotides being added are detected by virtue of their associated labels. In one particular aspect, they are observed using an optically confined structure, such as a zero mode waveguide (e.g., U.S. Pat. No. 6,917,726, which is incorporated herein by reference in its entirety for all purposes) that limits exposure of the excitation radiation to the volume immediately surrounding an individual complex. As a result, only labeled nucleotides that are in the process of being incorporated are exposed to excitation illumination for a time that is sufficient to identify the nucleotide. In another approach, the label on the nucleotide is configured to interact with a complementary group on or near the complex, e.g., attached to the polymerase, where the interaction provides a unique signal. For example, a polymerase may be provided with a donor fluorophore that is excited at a first wavelength and emits at a second wavelength, while the nucleotide to be added is labeled with a fluorophore that is excited at the second wavelength but emits at a third wavelength (e.g., U.S. Pat. No. 7,056,661, previously incorporated herein). As a result, when the nucleotide and polymerase are sufficiently proximal to each other to permit energy transfer from the donor fluorophore to the label on the nucleotide, a distinctive signal is produced. Again, in these cases, the various types of nucleotides are provided with distinctive fluorescent labels that permit their identification by the spectral or other fluorescent signature of their labels.

As will be appreciated, a wide variety of analytical operations may be performed using the overall reaction framework described herein and are applicable to the present invention. Such reactions include reactive assays, e.g., examining the combination of reactants to monitor the rate of production of a product or consumption of a reagent, such as enzyme reactions, catalyst reactions, etc. Likewise, associative or binding reactions may be monitored where one is looking for specific association between two or more reactants, such as nucleic acid hybridization assays, antibody/antigen assays, coupling or cleavage assays, and the like.

II. Analytical Device

The analytical system in accordance with the present invention employs one or more analytical devices referred to as "optode" elements. In an exemplary embodiment, the system includes an array of analytical devices formed as a single integrated device. An exemplar of a suitable optode element is disclosed by U.S. Provisional Application No. 61/306,235 filed on Feb. 19, 2010, and entitled INTEGRATED ANALYTICAL DEVICES AND SYSTEMS (the '235 application), the entire contents of which are incorporated herein for all purposes by this reference. The exemplary array is configured for single use as a consumable. In various embodiments, the optode element includes other components including, but not limited to, local fluidics, electrical connections, a power source, illumination elements, detector elements, logic, and a processing circuit. Each analytical device or array is configured for performing an analytical operation as described above.

While the components of each device and the configuration of the devices in the system may vary, each analytical device typically comprises the general structure shown as a block diagram in FIG. 1. As shown, an analytical device 100 typically includes a reaction cell 102, in which the reactants are disposed and from which the detector optical signals emanate.

"Reaction cell" is to be understood as generally used in the analytical and chemical arts and refers to the location where the reaction of interest is occurring. Thus, "reaction cell" may include a fully self-contained reaction well, vessel, flow cell, chamber, or the like, e.g., enclosed by one or more structural barriers, walls, lids, etc., or it may comprise a particular region on a substrate and/or within a given reaction well, vessel, flow cell or the like, e.g., without structural confinement or containment between adjacent reaction cells. The reaction cell may include structural elements to enhance the reaction or its analysis, such as optical confinement structures, nanowells, posts, surface treatments such as hydrophobic or hydrophilic regions, binding regions, or the like.

In various respects, "analytical device" refers to a reaction cell and associated components that are functionally connected. In various respects, "analytical system" refers to one more associated analytical devices and associated components. In various respects, "analytical system" refers to the larger system including the analytical system and other off-chip instruments for performing an analysis operation such as a power source and reservoir.

In some cases, one or more reactants for the reaction of interest may be immobilized, entrained or otherwise localized within a given reaction cell. A wide variety of techniques are available for localization and/or immobilization of reactants including surface immobilization through covalent or non-covalent attachment, bead, or particle-based immobilization, followed by localization of the bead or particle, entrainment in a matrix at a given location, and the like. Reaction cells may include ensembles of molecules, such as solutions or patches of molecules, or it may include individual molecular reaction complexes, e.g., one molecule involved in the reaction of interest as a complex. Similarly, the overall devices and systems of the invention may include individual reaction cells or may comprise collections, arrays, or other groupings of reaction cells in an integrated structure, e.g., a multiwell or multi-cell plate, chip, substrate or system. Some examples of such arrayed reaction cells include nucleic acid array chips, e.g., GeneChip® arrays (Affymetrix, Inc.), zero mode waveguide arrays (as described elsewhere herein), microwell and nanowell plates, multichannel microfluidic devices, e.g., LabChip® devices (Caliper Life Sciences, Inc.), and any of a variety of other reaction cells. In various respects, the "reaction cell", sequencing layer, and zero mode waveguides are similar to those described in U.S. Pat. No. 7,486,865 to Foquet et al., the entire contents of which is incorporated herein for all purposes by this reference.

Although the exemplary analytical system includes an array of analytical devices having a single waveguide layer and reaction cell layer, one will appreciate that a wide variety of layer compositions may be employed in the waveguide array substrate and cladding/reaction cell layer and still achieve the goals of the invention (e.g., published U.S. Patent Application No. 2008-0128627, incorporated herein for all purposes by this reference).

The analysis system typically includes one or more analytical devices 100 having a detector element 120, which is disposed in optical communication with the reaction cell 102, that is, the detector element is configured for direct detection of an emission event within the reaction cell. One will appreciate that such optical communication may include radiative or non-radiative communication. Optical communication between the reaction cell 102 and the detector element 120 may be provided by an optical train 104 comprised of one or more optical elements generally designated 106, 108, 110 and 112 for efficiently directing the signal from the reaction cell 102 to the detector 120. These optical elements may generally comprise any number of elements, such as lenses, filters, gratings, mirrors, prisms, refractive material, or the like, or various combinations of these, depending upon the specifics of the application.

In various embodiments, the reaction cell 102 and detector 120 element are provided along with one or more optical elements in an integrated device structure. By integrating these elements into a single device architecture, one improves the efficiency of the optical coupling between the reaction cell and the detector. In particular, in conventional optical analysis systems, discrete reaction vessels are typically placed into optical instruments that utilize free-space optics to convey the optical signals to and from the reaction vessel and to the detector. These free space optics tend to include higher mass and volume components, and have free space interfaces that contribute to a number of weaknesses for such systems. For example, such systems have a propensity for greater losses given the introduction of unwanted leakage paths from these higher mass components, and typically introduce higher levels of auto-fluorescence, all of which reduce the signal to noise ratio (SNR) of the system and reduce its overall sensitivity, which in turn can impact the speed and throughput of the system. Additionally, in multiplexed applications, signals from multiple reaction regions (i.e., multiple reaction cells or multiple reaction locations within individual cells) are typically passed through a common optical train, or common portions of an optical train, using the full volume of the optical elements in that train to be imaged onto the detector plane. As a result, the presence of optical aberrations in these optical components, such as diffraction, scattering, astigmatism, and coma, degrade the signal in both amplitude and across the field of view resulting in greater noise contributions and cross talk among detected signals.

The devices of the invention, in contrast, include relatively low volumes between the reaction cell and the detector, thereby reducing the noise contributions from those components and provide few or no free space interfaces that can contribute to the noise profile of the system through the introduced reflections and losses from large index changes from the components to air or free space. Further, in preferred aspects, a given reaction region is provided with its own devoted optical train to direct signals to a devoted portion of the sensor.

In various embodiments, the device is configured such that emitted light from the fluorescent species in the nanoscale well is not transmitted through free space. By "not transmitted through free space" it is generally meant that the respective element (e.g. a signal or energy) is not transmitted through open space or free space optics, and in various respects, is transmitted only through light-modulating media. Such light-modulating media may include refractive devices such as an optical lens that makes use of the refractive index of a defined volume of air. By contrast, light-modulating media generally does not include ambient air open to the environment.

As a result of the integrated architecture, optical aberrations are confined to individual reaction regions as opposed to being applied across an entire array of reaction regions. Likewise, in a further aspect, the reaction region, optical train, and detector are fabricated in an integrated process, e.g., micromechanical lithographic fabrication processes so that the components are, by virtue of the manufacturing process, pre-aligned and locked into such alignment by virtue of the fabrication process. Such alignment is increasingly difficult using free space optics systems as reaction region sizes decrease and multiplex increases. In addition, by integrating such components into one unified component, relative movement between such sub-components, as is the case with free space optics, can make drift and continued alignment resulting from vibrations a more difficult task. Likewise, the potential for contamination in any of the intermediate spaces (e.g. dust and other contaminants), is eliminated (or at least substantially reduced) in an integrated system as compared to free space systems.

In addition to reducing noise contributions from the optical pathway, the integrated devices of the invention also benefit from fabrication processes and technology that eliminate other issues associated with discrete reaction cell, optic, and detection components. For example, with respect to certain highly multiplexed or arrayed reaction cells, initial alignment and maintaining alignment of the detection with the reaction cell over the full length of the analysis can raise difficulties. This is particularly the case where excitation illumination may be specifically targeted among different array locations of the reaction cell and/or among different reaction cells.

In the embodiment shown in FIG. 1, a signal source, a transmission layer comprising optical components to modulate the light transmitted therethrough, and a detector are joined together into an integrated device.

As used herein, the term "integrated" may have different meanings when used to refer to different aspects of the invention. For example, in the case of an integrated device or an integrated optical system, the term "integrated" generally means that the various components are physically connected, and that the optical signals pass from component to component without passing into air or free space, as would be understood by one in the field of optics. In the context of the description of a system, the term "integrated" is to be understood as generally used in the analytical and electrical engineering fields, where "integrated" would refer, for example, to a combination or coordination of otherwise different elements to provide a harmonious and interrelated whole, whether physically or functionally. The meaning of the term will generally be understood by one of skill in the art by the context in which it is used.

Being an integrated device, the light emitted from the reactor cell 102 will pass through to the detector without passing through air or free space. In some embodiments, the integrated analytical device also comprises components for providing illumination to the reactor cell 102. For example, in many cases where reactor cell 102 comprises a zero mode waveguide, it is often desirable to provide illumination from below the reactor cell, for example between the bottom of reactor cell 102 and the transmission layer or optical train 104. In some cases, a waveguide structure is incorporated into the analytical device to provide such illumination. Analytical devices comprising waveguides for illumination are described in more detail herein, and for example, in U.S. patent application Ser. No. 11/849,157 filed Aug. 31, 2007 and Ser. No. 12/560,308 filed Sep. 15, 2009, which are incorporated herein by reference for all purposes.

In various embodiments, the analytical device is a substrate including a reaction cell array, and a detector array on a bottom surface of the array. The device may also include other components such as processing circuits, optical guides, and processing circuits. In various embodiments, the analytical device may be formed by building layers on a substrate or by bonding two or more substrates. In an exemplary device, a fused silicon (FuSi) substrate, a ZMW layer, and a silicon substrate with a photodetector array are bonded together to form the array of analytical devices. One will appreciate that such integrated analytical devices have significant advantages in terms of alignment and light collection. For example, the reaction site and detector are aligned through the manufacturing process. One will appreciate from the description herein, that any of the components and systems may be integrated or modified in various manner. In another example, the ZMW substrate and detector array are on separate substrates that are brought together for the experiment, after which the ZMW substrate is replaced with another substrate for a second experiment. With this approach, the detector array may be re-used rather than being disposed with the ZMW substrate after an experiment. It may also be more cost effective as the yields from each of the processes are separated. In this manner, the ZMW array and detector array are in intimate contact during the experiment (as if they are part of an integrated device), but they can be separated after the measurement.

The size of the processing circuits in each of the analytical devices may be minimized to reduce costs. By developing a board in the receiver camera electronics (e.g. massively parallel DSP or microprocessor or a dedicated FPGA, CPLD or ASIC), overall operating costs (i.e. $/mega-base) may be minimized.

Figure 2:
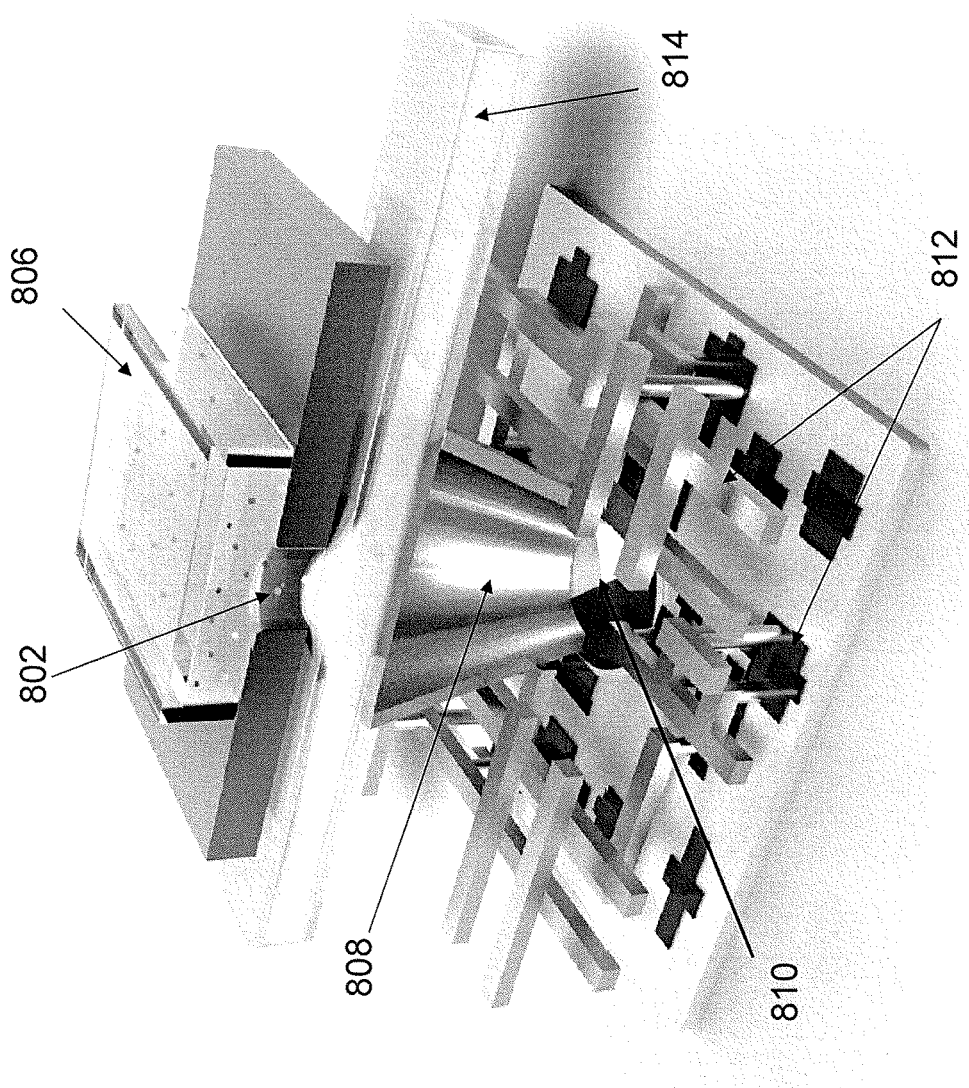
FIG. 2 is a schematic illustration of an integrated analytical device (optode) of the invention.

Another embodiment of an integrated analytical device of the invention (optode) is shown in FIG. 2. While FIG. 2 is shown in open form to illustrate the various components, it is to be understood that analytical device of FIG. 2 represents a structure that comprises all solid or liquid components and that there is no open space between the components.

The analytical device has a reaction cell 802 that is coupled with a reagent reservoir or fluid conduit 806 which delivers reactants to the reaction cell 802. The reaction cell can be a nanoscale well or zero mode waveguide. In some cases, the reaction cell will have a biomolecule such as a polymerase enzyme immobilized within it. The fluidic conduit can provide reagents across a number of reaction cells. Below the reaction cell is a waveguide for providing excitation illumination to the reagents within the reaction cell. While a waveguide is shown here, other optical elements such as those provided elsewhere herein can be used to provide light from under the reaction cell. The illumination light can be used to excite fluorescent emission from reagents with the reactor cell. The light emitted from the reaction cell is directed downward through a transmission layer, which acts to transmit the light from the reaction cell to the detector. In some cases, the transmission layer will have optical components to enhance the efficiency of the light transfer or modulate the light. In the analytical device of FIG. 2, an optical tunnel or conduit 808 is disposed in optical communication with the reaction cell 802, which is in turn in optical communication with sensing element(s) 810 in the detector. In some cases, the detector has multiple sensing elements, each for detecting light having a different color spectrum. For example, in the case of sequencing, the sensor for each reaction cell can have 4 elements, one for each of the four bases. In some cases the sensor elements provide color discrimination, in other cases, color filters are used to direct the appropriate color of light to the appropriate sensor element shown as a multicolor discriminating set of sensor elements in FIG. 2. The sensor elements are coupled to appropriate electronic components 812, such as busses and interconnects, that make up the overall sensor or camera. The electronic components can also include processing elements for processing the signal from the detectors.

III. Optode Arrays and Packaging

The integrated analytical devices of the invention are generally fabricated into arrays of devices, allowing for simultaneously observing thousands to millions of analytical reactions at one time. These arrays of optodes generally require the input of fluids to provide reagents and the conditions necessary for carrying out analytical reactions, the input of excitation light for the measurement of fluorescence, and connections for the output of signal data from the detectors. The invention provides devices, systems, and methods for packaging the optode arrays for these inputs and outputs.

Figure 3:
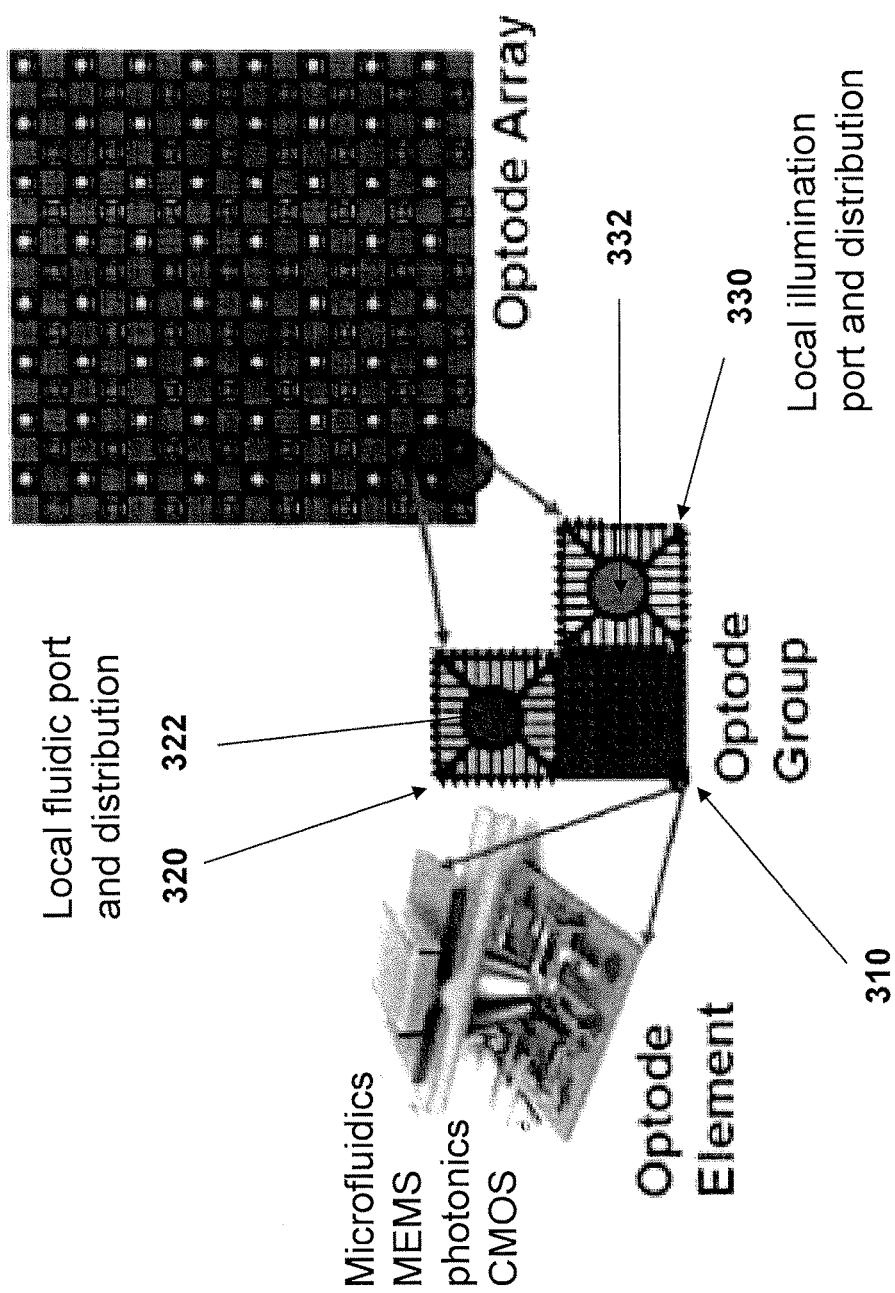
FIG. 3 is a schematic illustration of integration of an integrated analytical device (optode) into an optode array chip in accordance with the present invention.

FIG. 3 provides an embodiment for providing an array of optode elements into an optode array group and an optode array chip, which facilitate the input of light and fluid and the electronic output of data. The optode array chip can be introduced into an instrument or system that is configured with the required input and output connections. For example, in some cases the light and fluid can be introduced from above through input ports on the top of the chip, and electronic data can be extracted from below the chip from electronic contacts on the bottom of the chip. The optode array group comprises an optode array component 310, a fluidic input component 320, and an illumination input component 330. In the embodiment shown in FIG. 3, the fluidic input component 320 and illumination input component 330 are attached to the optode array component at the edges.

The exemplary optode array component 310 comprises an array of optode elements. The number of optodes in the array can be set by the characteristics of the analytical reaction to be measured. The number of optode elements in an optode array component can be from about 10 to about a million or more. In some cases the number of optode elements is from about 100 to about 100,000. As shown in FIG. 3, the fluidic conduit extends over a given optode to the optodes on other sides. As shown in the figure, the exemplary fluidic conduit extends across the optode element in one direction, but essentially not in the perpendicular direction. The fluidic conduits can be fashioned in some cases to extend over multiple optode elements in either or both directions. In some cases, the conduit can deliver fluid to all of the optodes on the optode array component. In some cases, one conduit can deliver fluid to a subset of the optode elements, while other conduits deliver fluid to other optode elements. In some cases, each conduit delivers fluid to a single optode element. Analogously, the waveguides shown for a single optode element in the figure generally extend across multiple optode elements in the array. The waveguides can be channel waveguides extending down a single row of optode elements providing illumination to the reaction cells in that row, or the waveguides can be channel waveguides wider than one row, illuminating more than one row. The waveguides can also be planar waveguides illuminating sections or illuminating all of the reaction cells in the optode array component.

The fluidic input component 320 has a fluid input port 322 for introduction of fluids to the optode array chip. In the embodiment shown in FIG. 3, the fluid input port is accessible from the top. The fluidic input port 322 has a number of fluidic conduits that extend from the input port to the optode array component. The fluidic conduits on the fluidic input port generally mate directly with the fluidic conduits on the optode array component, and both components are generally formed in the same set of process steps. The number of fluidic conduits may depend on the application. In some cases, one fluidic conduit will provide fluid for one row within the reaction cells in the optode array component.

The illumination input component 330 has an illumination input port 332 such as a light pipe for the input of illumination light onto the optode array chip. The illumination input port 332 is connected to a plurality of waveguides that extend from the illumination input port into the waveguides on the optode array. Briefly, waveguides may be provided within the substrate by including higher IR regions to convey light through a lower IR material substrate, where the lower IR material functions as a partial cladding for the waveguide. The waveguide meets the reaction cell with an absence of cladding, allowing evanescent illumination of the reaction cell from the waveguide.

The combination of an optode array component 310, a fluidic input component 320, and an illumination input component 330 as shown in FIG. 3 can be referred to as an optode array group. A plurality of optode array groups can be combined to form an optode array chip. The optode array chip can comprise from 1 to about 100, from about 100 to about 1,000, or more optode array groups. The optode array chip comprising multiple optode array groups can be fabricated using semiconductor and microfabrication processing techniques. For example, an optode array chip containing an array of optode array groups can be fabricated on a wafer, and the wafer can be diced into smaller optode array chips having the appropriate number of optode array groups for a particular application. The optode array chips thus produced will have the fluidic and illumination input ports, and will have electrical contacts extending from the detectors and other electronic elements on the chip for the transfer of data.

Figure 4:
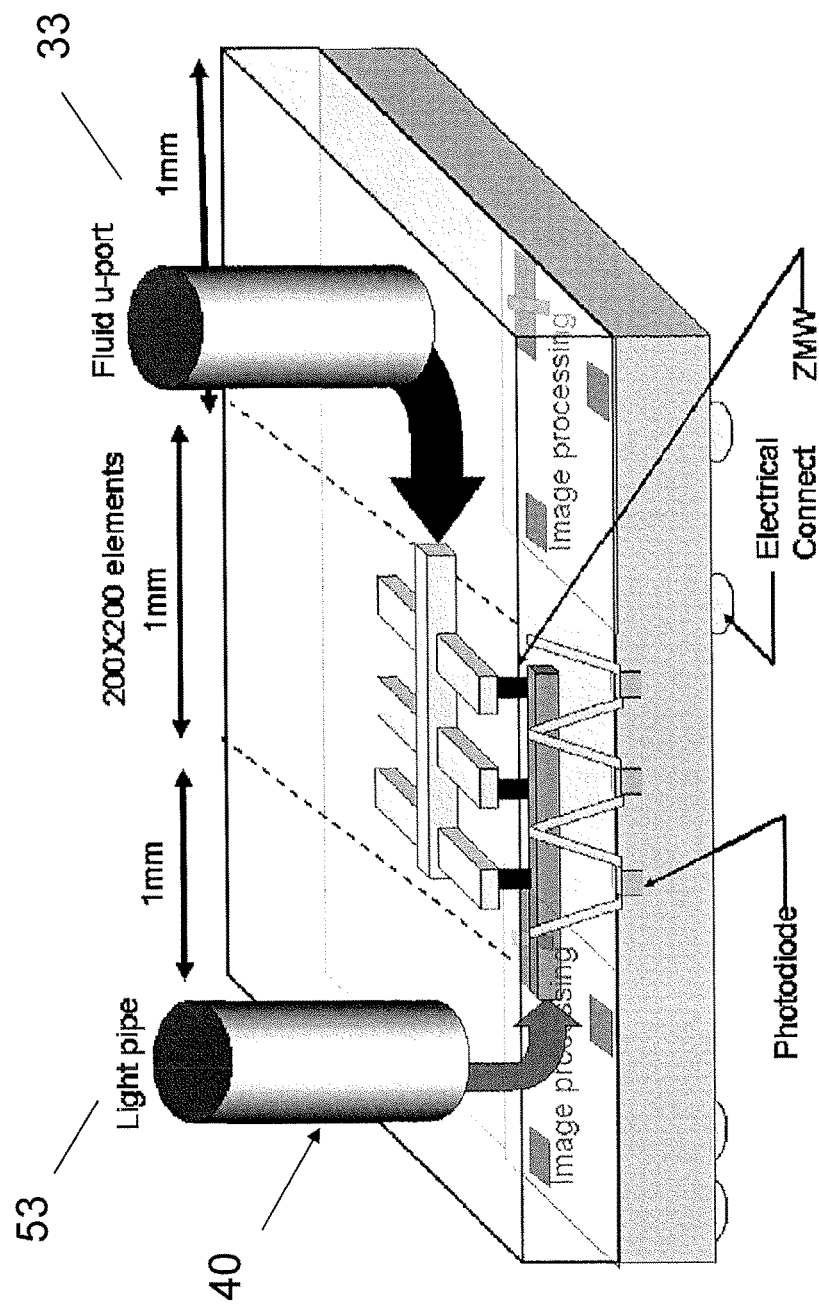
FIG. 4 is a schematic view of a topside connection of fluidic and illumination elements to an integrated analytical device.

FIG. 4 illustrates how an optode array component (middle) having, for example, 200 by 200 optode elements can be supplied with fluid and light from the side. Fluidic port 33c dispenses fluid into an array of fluidic channels that bring the fluid to the reaction cells or ZMWs. Light pipe 53 couples light into channels that transfer the illumination light into the reaction cells from below. Emitted light from the ZMWs is transmitted through a transparent transmission layer down to the detector, in this case a photodiode. The photodiodes detect optical signals and transmit data signals into image processing elements on the chip. Processed signal data is sent to computers for further processing through the electrical contacts on the bottom of the chip.

In one aspect, the invention comprises a device comprising an array of optode elements wherein each optode element has a reaction cell such as a ZMW or a nanoscale aperture within a cladding layer, the reaction cell configured to receive fluid that contains the reactive species to be analyzed. The analysis generally comprises at least one fluorescently labeled species, the fluorescence from which will provide information about the reaction. Above the reaction cell is a fluidic layer that is in fluid communication with the reaction cell. Below the aperture layer is a waveguide layer that provides illumination to the nanoscale well with evanescent irradiation. The waveguide layer can comprise channel waveguides and/or planar waveguides. Below the waveguide layer is a transmission layer that transmits light emitted from the fluorescent species in the reaction cell to the detector below. Below the transmission layer is a detector layer which receives and detects the emitted light transmitted through the transmission layer, wherein the emitted light is transmitted to the detector without being transmitted through air. In some cases, the detector layer has below it electrical contacts for transmitting data signals out of the chip into computer components for analysis and processing. In some cases processing elements are built into the chip to provide some processing of the signals before sending the data off of the chip.

The array of optode elements is generally provided in one integrated, solid package. In some cases, the portion of the array of optode elements that comprise the detector can be reversibly separated from the portion of the array comprising the reaction cell. This allows for the detector portion to be used over and over again with different arrays of reaction cells.

IV. Measurement Systems Comprising Optode Arrays

The optode array chips comprising optode arrays, inputs for light and fluid, and outputs for electronic transfer of data can be inserted into structures that provide for the analysis reaction. In some cases, the optode array chip can be sandwiched within an assembly that provides physical alignment of the input and output features, and can provide the force required for effective mating of the assembly components. One approach to an assembly is the use of a clamshell assembly. An exemplary system includes an array of analytical devices integrated into a system with a test socket. An exemplary system architecture makes use of automated testing equipment and chip-scale packaging techniques. In various embodiments, the test socket is an automated test equipment (ATE) socket (shown in FIG. 5A). In the exemplary system, the socket is connected to the processing system and other system components such as the electrical system.

In some aspects the invention provides an assembly having a sandwich structure comprising: a top piece comprising inputs for illumination light and fluid; an integrated analysis chip in the middle comprising: an aperture layer comprising a plurality of nanoscale apertures through a cladding layer in fluidic contact with the top of the chip, and a waveguide layer comprising a plurality of waveguides configured to provide illumination light to the nanoscale apertures from below, the waveguide layer having one or more illumination ports on the top surface for providing illumination light to the waveguides; a transmission layer comprising a transparent material for transmitting emitted light from the nanoscale apertures; a detector array layer below the transmission layer having detectors electrically connected to pins extending out the bottom of the chip; and a bottom piece having electrical contacts corresponding to the pins on the bottom of the chip; the assembly configured such that upon closure, the chip is aligned with the top and bottom pieces to allow input of the illumination light and fluid from the top piece and extraction of electrical signals from the bottom piece.

Figure 5A:
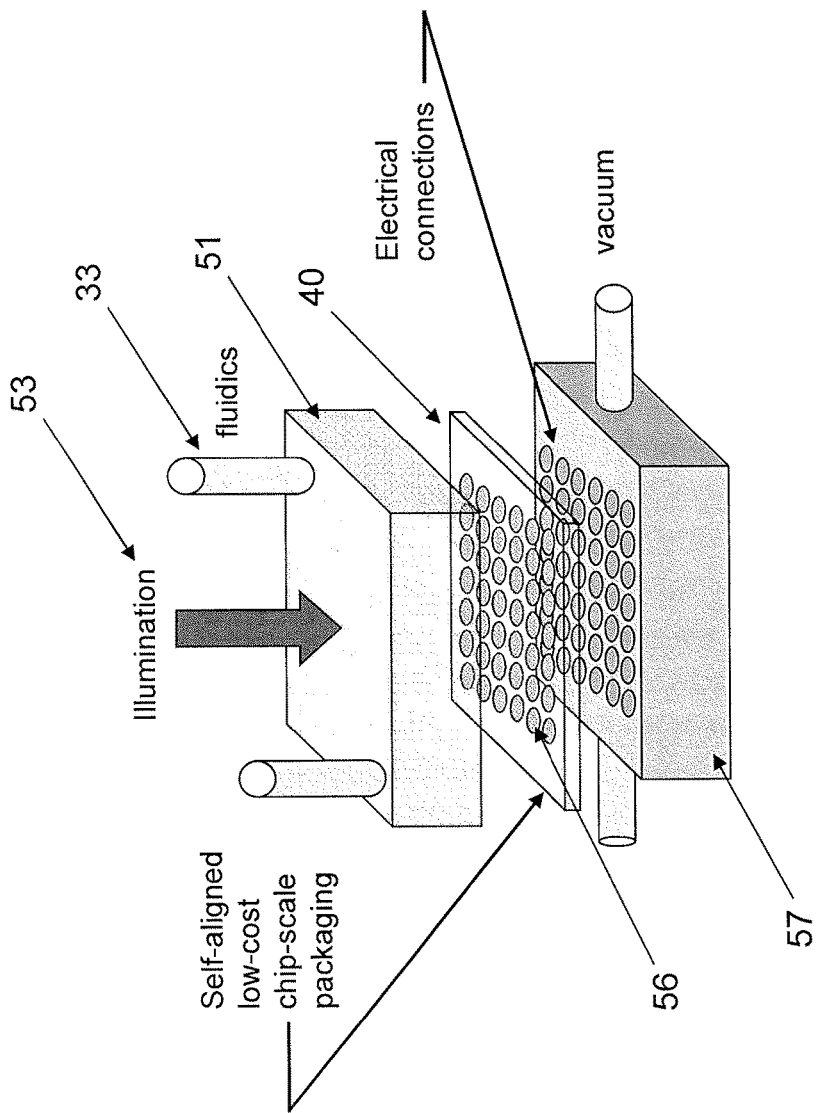
FIG. 5A is a schematic view a test socket and analytical system.
Figure 5B:
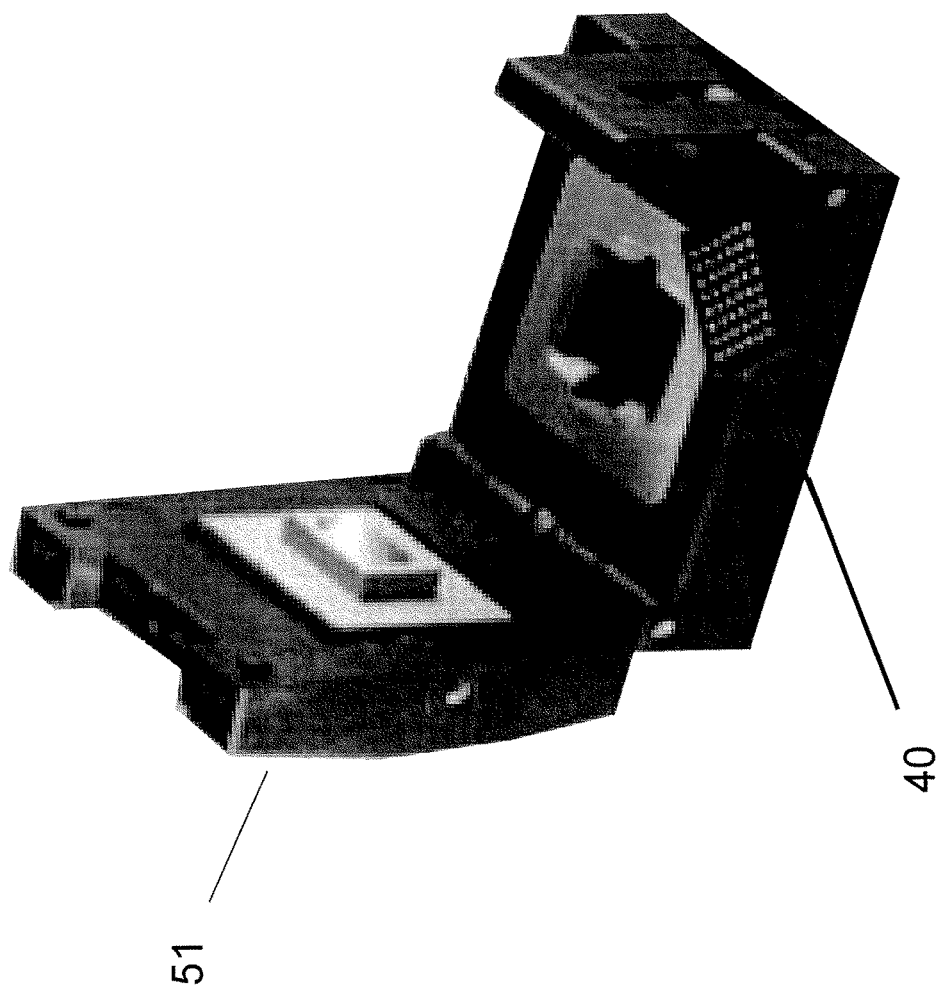
FIG. 5B is a perspective view of an exemplary test socket receiving an exemplary analytical optode chip.

An exemplary integrated device isolates the electrical components from the optical and fluid components, for example, having the optical and fluid delivery on one side and the electrical interconnects on the other side of the device. One embodiment of a system is shown in FIGS. 5 and 5A in which an optode array chip 40 comprising, for example, an array of optode array groups 56, is inserted into a socket comprising a top piece 51 which delivers illumination through an illumination system 53 and fluidics delivery system 33 to the optode array chip, and bottom piece 57 which has an array of electrical contacts which mate with the electrical contacts on optode array chip. In some embodiments the socket can use vacuum to pull the components of the system together to enhance fluidic, illumination, and electrical contacts.

The electrical connections are generally on the bottom surface of the integrated device and optical and fluidic connections on the top side of the device (shown in FIG. 5). The partition of the electrical and optical components in this exemplary manner provides for a two-sided socket that can supply all 110 connections within standard commercial tolerances. As an example, the clamshell socket used in the exemplary commercial ATE may be modified to be used with the analytical array 40. Such test sockets generally have over 50,000 insertion cycle reliability and provide adequate and uniform contact force. Moreover, because the components are integrated into a single device and the socket is self-seating, the optical components and detector are automatically aligned. The exemplary includes spring loaded durable contact pins and oxide scrubbing crowns to further promote auto alignment and reliable contact. Thus, the integrated device can be easily connected to the processing system and other system components by insertion into the socket. This provides higher reliability, lower cost, and generally easier use by the technician.

The reagent handling, sample handling, and illumination functions may be performed in a distributed manner on an area above a processing region of the integrated device and adjacent to the reactor cells. The illumination ports and fluidics ports may be positioned in alternating rows in a checkerboard pattern. These illumination and fluidic ports can service either a single adjacent optode array component 56 or in some cases can service four of the nearest neighboring optode array components. The distribution of illumination and fluids is more uniform, less complex, and performance is maintained to very high multiplex via array segment scalability. Each array segment illumination and fluidics can be individually controlled if desired. In various embodiments, fluidics and photonic connections to socket 51 are made on the top portion of device 40.

With the illustrated top-bottom connection set-up, a standard clamshell packaging technique (e.g. ATE socket) as described above can be used to connect the device to the overall system. As shown in FIG. 4, for example, the topside connections involve the alignment of multiple illumination light pipes 53 and microfluidic nozzles 33. For example, if a 2000×2000 cell array is needed and 100 array segments are placed in 200×200 multiplex on 5 micrometer centers, the adjacent 100 I/O and processing segments are 1 mm×1 mm in size. Therefore, 10×5 connections of both illumination and fluidics are needed but have achievable alignment at the pitches described. In a similar fashion, the data reduction performed in the processing regions reduces the number of electrical connections that need to be interfaced to the external circuitry. Standard electrical bump bonds can be used to connect with standard durable electrical sockets with achievable tolerances for high speed operation. The light pipe 53 in the system of FIG. 4 is configured to direct a light signal distributed over the device to a site of interest, in the exemplary case, a waveguide. The integrated waveguide then directs the light to respective reaction cells.

Referring to FIG. 5, a sample is provided to the top of the socket and introduced to a set of pipettes that are aligned with the fluidic ports on the optode array. Since the optodes are grouped into sub-arrays, the reduced number of fluidic ports allows for alignment to standard commercial tolerances (e.g. about 0.3 mm) and the reduced number of connections increases reliability. The failure of a single port does not make the entire experiment invalid and the remaining ports can collect data.

Figure 6:
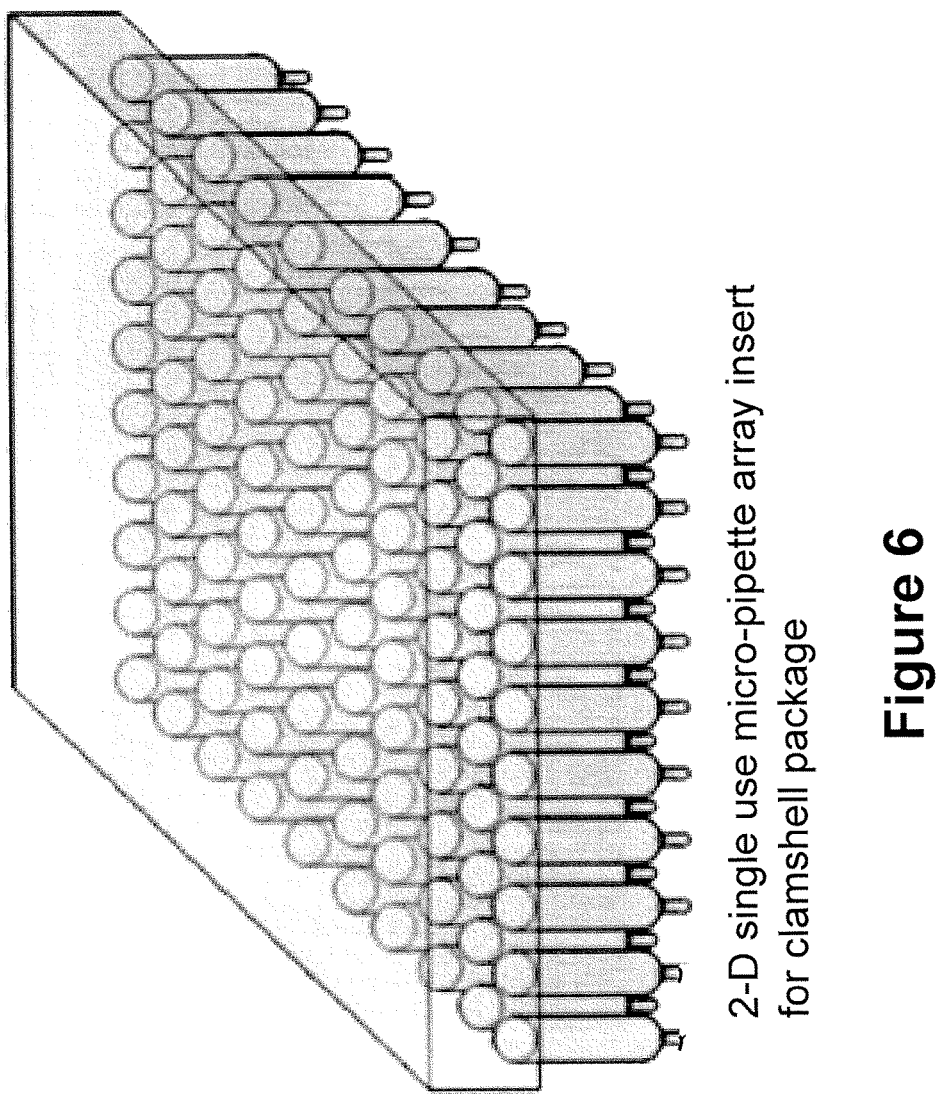
FIG. 6 is a schematic view of a micro-pipette array for delivering reagent to an optode chip array.
Figure 7:
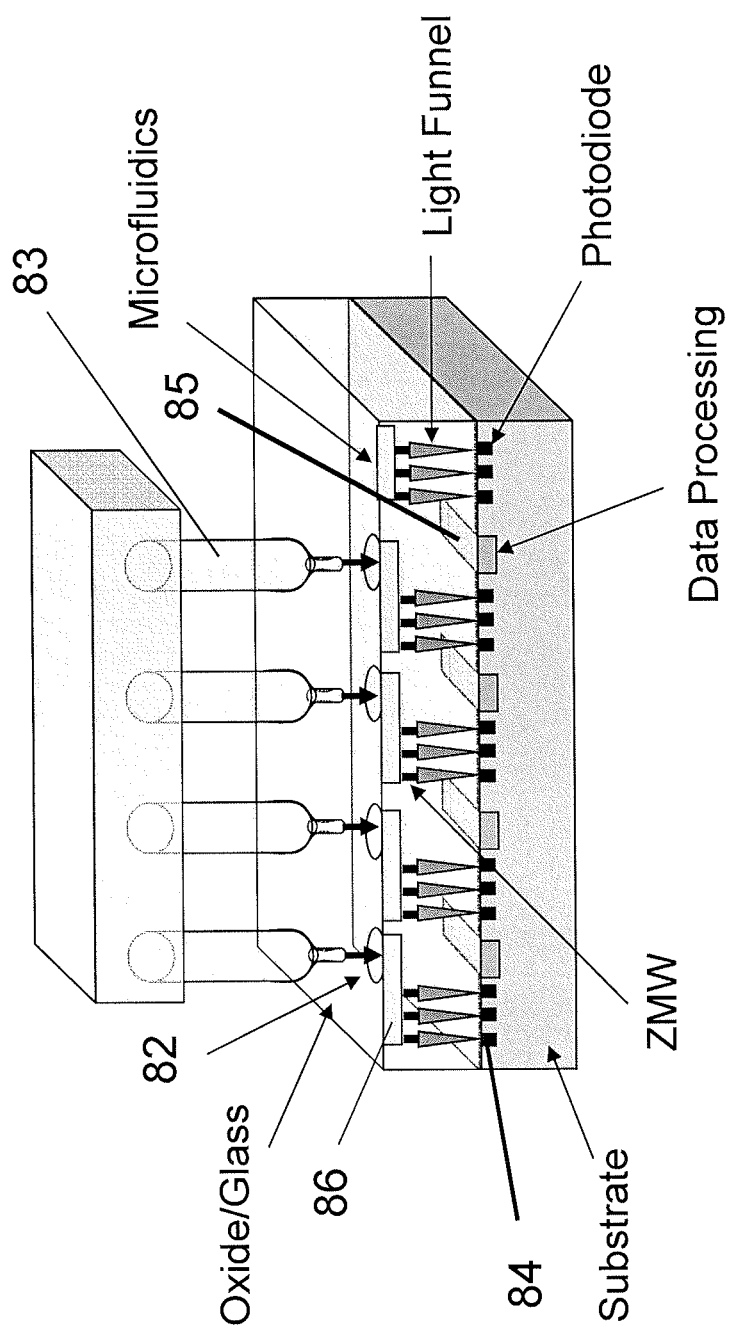
FIG. 7 is a cross-sectional view of the test socket and analytical system illustrating microfluidic connections.

The integrated system of the present invention is typically configured to introduce fluids and optical signals. To provide for a sterile environment to introduce sample and reagent, a low cost fluidic distribution device with single-use capability can be inserted into the socket with each experiment. This fluidic device can be molded with standard bio-compatible polymers similar to multiple micro-pipette systems sold by companies such as Biohit, Thermo and Eppendorf. An example of a disposable 2-D micro-pipette insert for the ATE clamshell socket lid is shown in FIG. 6. FIG. 7 shows a diagram of the introduction of fluids into the optode array chip with an array of micropipettes configured to mate with the fluidic input ports on an optode array chip. The micropipette array 83 mates with fluidic input ports 82 on the optode array chip. The fluid extends down conduits 86 into the optode elements. The ZMWs within the optode elements are illuminated, and emitted light is transmitted through light pipes to the detectors 84. The detectors send signals to data processing components within the chip.

The introduction of fluidics to optode groups may be done with homogenous material, or alternatively, each optode group could be operated with a different sample or reagent setup to perform highly multiplexed assay experiments. The temperature of each fluidic input can also be adjusted or maintained, for example, to provide variability in the assay.

Figure 8:
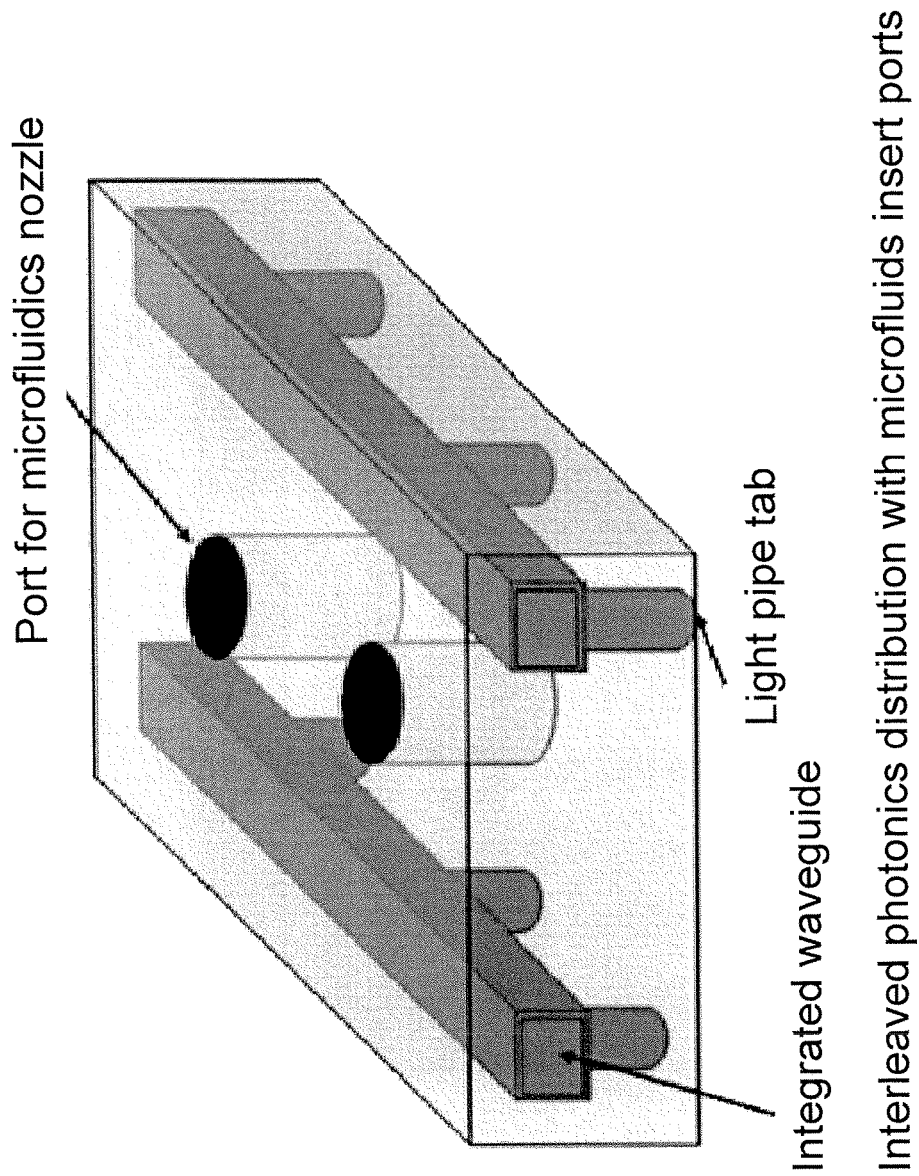
FIG. 8 is a schematic view of a top portion of the test socket illustrating distributed photonics and fluidics system.
Figure 9:
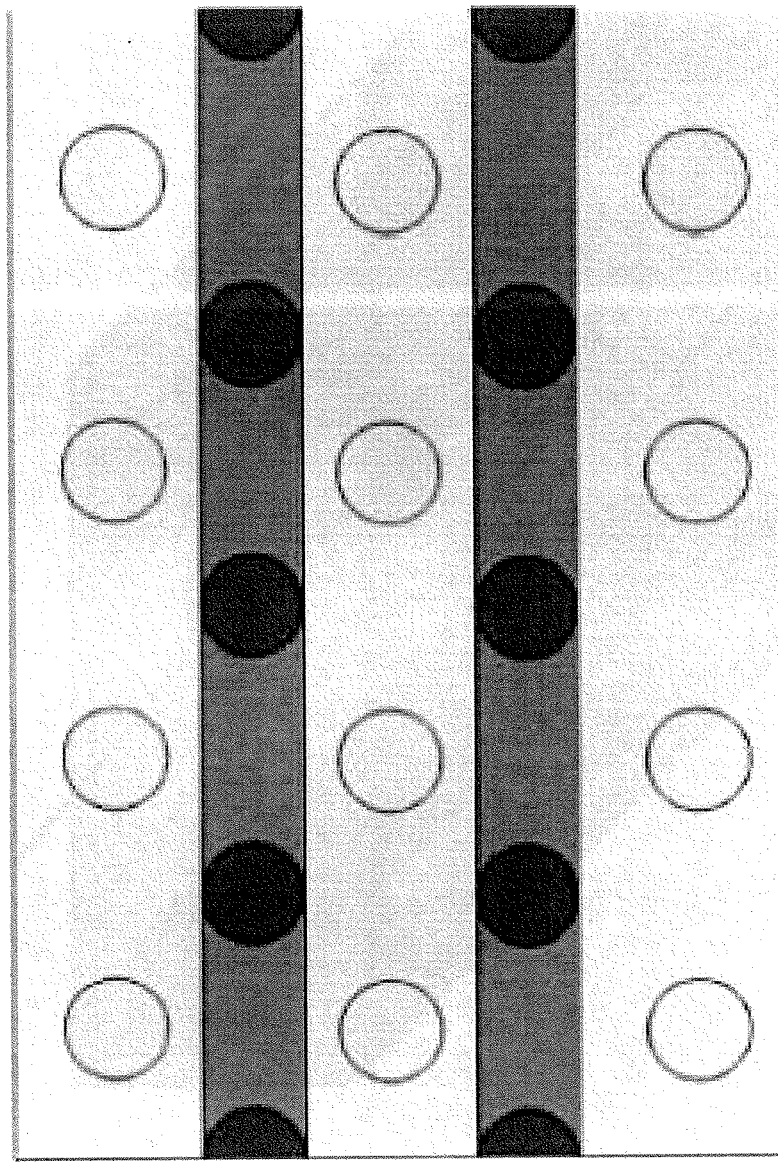
FIG. 9 is a top view of a test socket of FIG. 8.

In various embodiments, the introduction of the photonic illumination signal is accomplished with discrete light ports at the top part of the clamshell socket within commercial tolerances (e.g. between about 0.3 mm to about 0.6 mm). By distributing the light energy in the durable socket to local optode regions, careful design and exotic materials can be used to minimize losses, enable polychromatic excitation and reduce heat load on the active single use device. For example, a lithium niobate waveguide structure can be designed with very low insertion and propagation losses to the optode group. Lower quality distribution networks on the disposable chip are enabled as the transmission distance and branching are significantly reduced. The photonic distribution network can be developed to be interleaved with the microfluidic distribution insert as shown in FIG. 8 and FIG. 9.

Turning to FIGS. 10A, 10B, and 10C, an array with distributed functions is shown. FIGS. 10A, 10B, and 10C represent layers within an optode array chip illustrating the various functions performed in different portions of the chip. The exemplary optode array chip includes a plurality of individualized analytical devices for carrying out a reaction. FIG. 10B shows the topside of the optode array chip having reactor array components 71, illumination input components 72, and fluidic input components 73. FIG. 10A shows the layer in which the optode array components have an array of detectors 70. As illustrated, the detectors are connected to processing components 75. These processing components process the signal from the detectors before sending the signal on for further processing and analysis. FIG. 10C shows the base of the optode array chip. The base has an array of electrical connections. In the embodiment shown, the portions of the chip under the optode array components have contacts for the input of power. The portions of the chip under the fluidic input and illumination input components have electrical contacts for the output of signal from the signal processing elements. The exemplary optode array chip is configured for efficient processing. Some of the functions, such as detection, are carried out within each optode. Other functions are handled by groups of optodes or across the distributed system. For example, the fluidics system extends across the rows and columns of optodes.

The illustrated array is manufactured using techniques similar to silicon wafer preparation and testing techniques. The array is built up from a substrate with any of the above mentioned analytical elements. The array does not require regular spacing. One will further appreciate that the system architecture can be easily set up and scaled. Each "unit" may be an integrated, local system with a number of optical, detection, and processing elements. The outputs of each of the reactor cell detectors (containing the preprocessed pixel data) is connected to a processing circuit where many functions of various utilities can be performed including, but not limited to, data reduction, digitization, buffer storage, bus arbitration, and the like.

Referring to FIG. 10B, the reagent handling and illumination can be performed in a distributed manner using the area above the processing region and adjacent to each of the respective reactor cells. A checkerboard pattern of alternating rows of illumination ports and fluidics ports is provided. These fluidic and illumination ports can be provided as described above as arrays of optode array groups. These ports can service either the single adjacent reactor array or a plurality of arrays. In various embodiments, each node or set of ports services the neighboring arrays (e.g. arrays on each of the four sides). In contrast to conventional devices, the distribution of illumination and fluids is more uniform and less complex and performance is maintained to very high multiplex via array segment scalability. One will appreciate that each array segment illumination and fluidics can be individually controlled if desired.

Referring to FIG. 10C, the readout of array segments can be performed via local through-hole vias to substrate connections. The packaging and testing of the system can be done with industry accepted and verified processes. To complement the fluidic and illumination connections on the topside of the wafer, a number of electrical connections representing the I/O of the array segments may be made on the bottom of the wafer as discussed above. These connections can be segmented by power and signal groups. Thus, the connections are positioned at the top and bottom of the array chip.

A standard clamshell packaging technique (e.g. ATE socket) as described above can be used to connect the chip device to the overall system. As shown in FIG. 4, for example, the topside connections involve the alignment of multiple illumination light pipes 53 and microfluidic nozzles 33. For example, if a 2000×2000 cell array is needed and 100 array segments are placed in 200×200 multiplex on 5 micrometer centers, the adjacent 100 I/O and processing segments are about 1 mm×1 mm in size. Therefore, 10×5 connections of both illumination and fluidics are needed but have achievable alignment at the pitches described. In a similar fashion, the data reduction performed in the processing regions reduces the number of electrical connections that need to be interfaced to the external circuitry. Standard electrical bump bonds can be used to connect with standard durable electrical sockets with achievable tolerances for high speed operation.

In some embodiments, a plurality of devices are formed in a substrate (e.g. wafer) cut from a sheet material. The wafer can comprise, for example, silicon or fused silica. The exemplary device includes a real-time sensing structure integrated with the chemical reaction cells and provides for the decoupling of the reactor location with the optical elements. The detector elements are grouped around distributed processing cells thereby enabling significant performance advantages with high parallelism. In addition, this architecture reduces the distribution path for fluidics, signal, and stimulus by arranging cells into groups of manageable I/O "pads" corresponding to optode groups.

Figure 11:
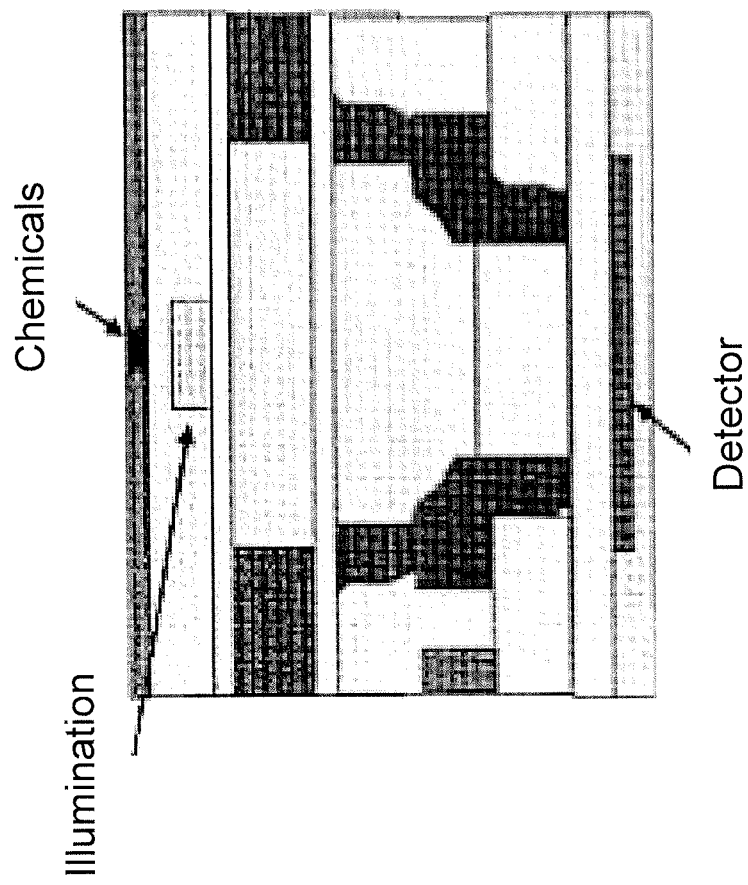
FIG. 11 is a schematic view of an analytical device having directional components defining an optical guide path, the device being formed from layers on a substrate.

The implementation of integrated sensing elements with the cell arrays/reactors provides many benefits including higher speed operation and the ability to extract tagged signals from reduced emissions with synchronized light. FIG. 11 shows another embodiment of an integrated analytical device cell with a fully contained light source, cell reactor element, and detector. By eliminating common and redundant illumination and detection paths, the fidelity of the sensed signal is maintained.

While there are many benefits of a distributed architecture, the distribution branching network required for a high resolution array presents some challenges and limitations. For example, the losses associated with a waveguide operating with many branches and taps will introduce a light intensity gradient across the device. One method of overcoming this problem is with cross-hatched, alternating waveguides. In some cases, the device uses monochromatic illumination and detection techniques to avoid or mitigate such problems.

Figure 12:
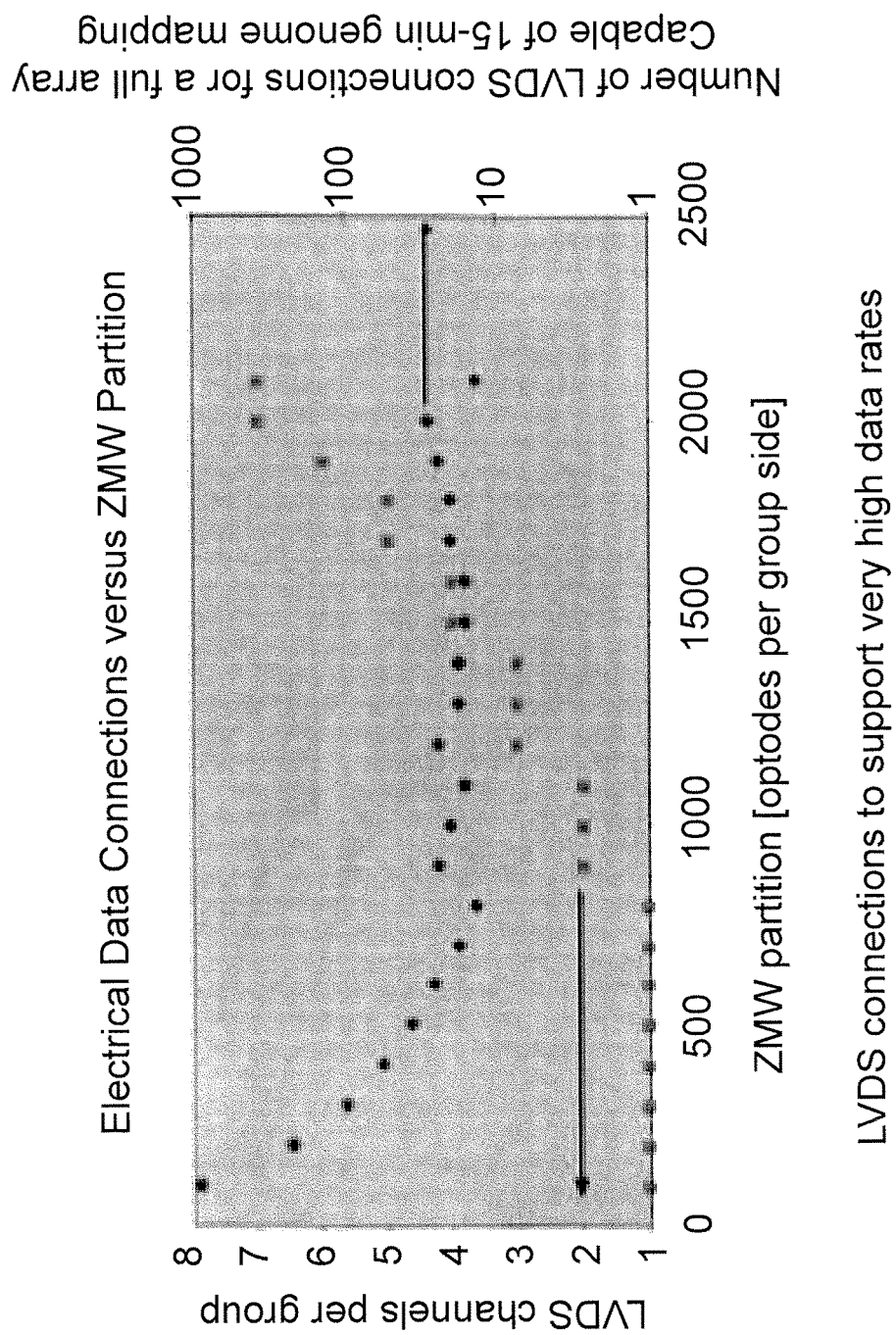
FIG. 12 is an exemplary plot of interleaved electrical data connections versus single molecule waveguides.

In an exemplary system, the development of low cost packaging for analytical arrays is enabled with the use of chip scale packaging techniques. For example, the use of through-hole vias with distributed processing and data collation circuitry enables the multiplexing of many analytical signals onto a greatly reduced number of I/O lines. By example, a collection of 256×256 elements each operating at 25 incorporations per second and providing 5 bytes per event requires an electrical bandwidth of about 65 mega-bits per second. This bandwidth can be provided at only about 10% of the maximum data rate of standard LVDS signaling (ANSI-644) which only needs two connections. For a device capable of mapping an entire genome in 15 minutes, for example, as few as 14 LVDS electrical connections are required as is shown in FIG. 12.

One will appreciate from the description herein that exemplary integrated device provides a high degree of scalability. The integrated devices may be extended to a scalable array segment at very high resolution. In this high resolution array, the performance across the array (periphery versus center) is made more uniform with the herein-described system architecture. One will appreciate that the size and arrangement of the reactor arrays and optodes is relatively flexible. The partition of the reactor array sections and the adjacent distribution and processing regions can be sized across a relatively wide range and each section can be spaced with respect to each other at varying distances to support the overall function required.

Although in various respects the analytical device is described as being fabricated in a monolithic fashion, such that all integrated elements are fabricated from the outset into the same structure, one will appreciate from the description herein that other manufacturing techniques may be utilized. In some cases, different components are fabricated separately, followed by integration of the separate parts into a single integrated device structure. For example, the sensor elements, optionally including one or more optical elements, may be fabricated in a discrete component part. Likewise, the reaction cells may be fabricated in a discrete component part optionally along with one or more optical components. These two separate parts can then be mated together and coupled into a single integrated device structure where the sensor elements in the first component part are appropriately aligned with the reaction cells in the second component part. In various embodiments, the analytical device employs modular assembly techniques. In this manner, various components can be joined, separated, and reassembled as needed. For example, the reaction cell array and waveguide and sensor may be assembled during an experiment and then separated so the cell array and waveguide can be replaced for set-up of the next experiment.

V. Excitation and Optical Components

Figure 13:
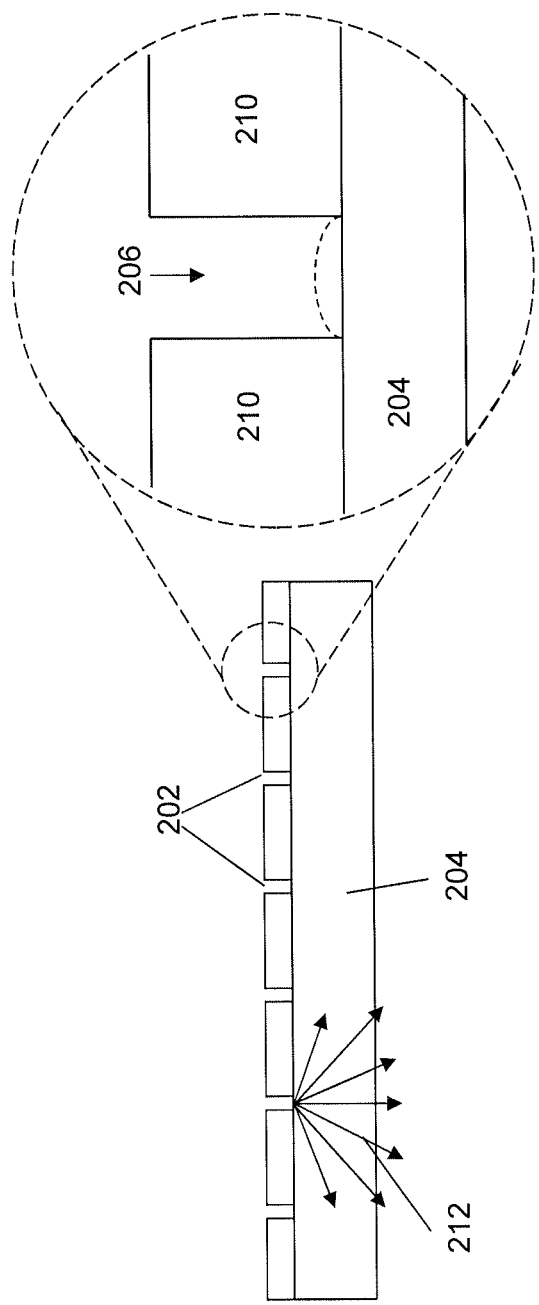
FIG. 13 is a schematic view of an array of reaction cells and the optical emission profiles emanating from those reaction cells.

FIG. 13 illustrates the general nature of optical signals from a reaction cell in various aspects of the present invention. As shown, the reaction cell or region comprises a very low volume reaction region such as a zero mode waveguide (ZMWs), e.g., ZMWs 202, disposed upon a substrate 204. As shown in the exploded view, a ZMW comprises an unfilled core 206 or aperture disposed through a cladding layer 210 that typically comprises a metal film layer. As described in, e.g., U.S. Pat. Nos. 6,917,726 and 7,486,865, the entire contents of which are incorporated herein for all purposes, the exemplary zero mode waveguide structure is of sufficiently small dimensions that light that is at greater than a cut-off frequency that enters into the waveguide core 208 is not propagated through the core but exhibits evanescent decay through the core. This allows for efficient illumination of just the volume of the ZMW at the opening (schematically illustrated by the dashed line within core 206) and collection of any optical emissions that occur within the same volume. The result is to permit excitation of and collection of fluorescent emission from individual molecules disposed at the opening of the core, e.g., on a transparent base layer. Light signals from the reaction cell, or ZMW 202 as shown, are emitted in a Lambertian distribution, as shown by arrows 212. Efficient capture of signals exhibiting this profile may necessitate either directional optics to re-direct the signals toward a detector or provision of a detector that matches the hemispherical surface of this signal profile.

In various embodiments, the analytical device of the invention makes use of various excitation techniques. In an exemplary embodiment shown in FIG. 14, the analytical device makes use of a top-side flood illumination method. The fluidic channels and ZMWs are optically shielded from topside illumination and a path to direct the light to the active area of the ZMWs is provided. The top half of the exemplary optode integration socket (e.g. an ATE socket) is transparent to the flood illumination while shielding the microfluidic insert. The socket may be made of a waveguiding material to assist with the flood illumination of the part. For example, the socket may include a structure or materials selected to guide the flood illumination along a predetermined path.

Figure 14:
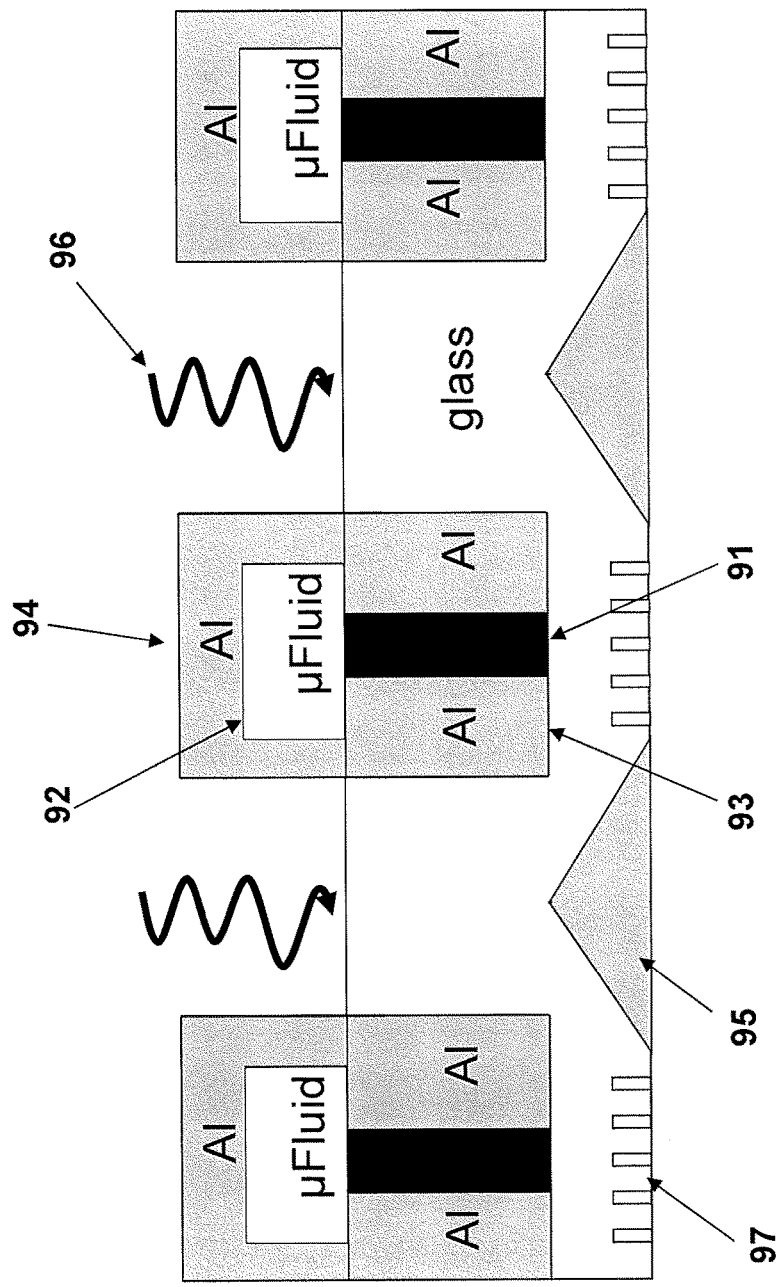
FIG. 14 is a schematic view of an array of reaction cells in a transparent substrate, illustrating an embodiment for providing illumination light to the reaction cells.

In FIG. 14, the optode array chip comprises an array of ZMWs 91 formed within a transparent substrate such as glass. Surrounding the ZMWs and extending into the top surface of the glass substrate are regions of opaque cladding material comprising, for example, a metal such as aluminum or other suitable metals, a metal oxide, or a composite of metal and metal oxide. Illumination light 96 introduced from above the chip in flood fashion passes down through the glass and is directed upward to the bottom of the ZMWs by optical elements 95, which can comprise mirrors or dielectric stacks. The light can stimulate emission from sample within the ZMW, the emitted light from which is transmitted down to optical detectors 97. Fluid is transported to the ZMWs by fluid conduits 92. The tops of the ZMWs are covered with an optically opaque covering 94 which prevents the illumination light from entering the ZMW from above. The opaque covering 94 can comprise a metal such as aluminum.

In some aspects, the invention comprises a device for measuring analytical reactions comprising a transparent substrate including a plurality of rows of nanoscale apertures extending through an opaque cladding to the top of the transparent substrate. The rows of nanoscale apertures are separated by regions of the transparent substrate open to illumination from above. The device has a plurality of fluidic conduits, each on top of and in fluidic contact with a row of nanoscale apertures. For these exemplary devices, each fluidic conduit is coated with an opaque material that prevents the illumination light from entering the nanoscale aperture from above. In addition, the device has a series of features below the nanoscale apertures configured to direct illumination light from above the transparent substrate up into the nanoscale apertures from below. In some embodiments the device also has built-in optical detectors, with at least one detector per nanoscale aperture. In some cases, the device has multiple detectors for each nanoscale well, for example, four detectors, each sensitive to a different color to allow for four color nucleic acid sequencing.

Various aspects of the invention are directed to waveguide architectures excited by laser beams that impinge on the device chip from below. The beams may be subjected to refractive redirection within the chip. Final shaping may be performed with optical elements such as micromirrors (though the wavevector, k, does not change direction) and other devices as will be appreciated from the description herein.

FIGS. 15, 16, 17, 18, and 19 illustrate various other techniques for light-based excitation in accordance with the invention. In contrast to conventional devices making use of bottom-side illumination, the exemplary devices provide increased flexibility in the method and direction of illumination. The increased flexibility can be important in the exemplary case where much of the chip surface area is occluded by microfluidics and electronics and not available for photonic injection.

Figure 15:
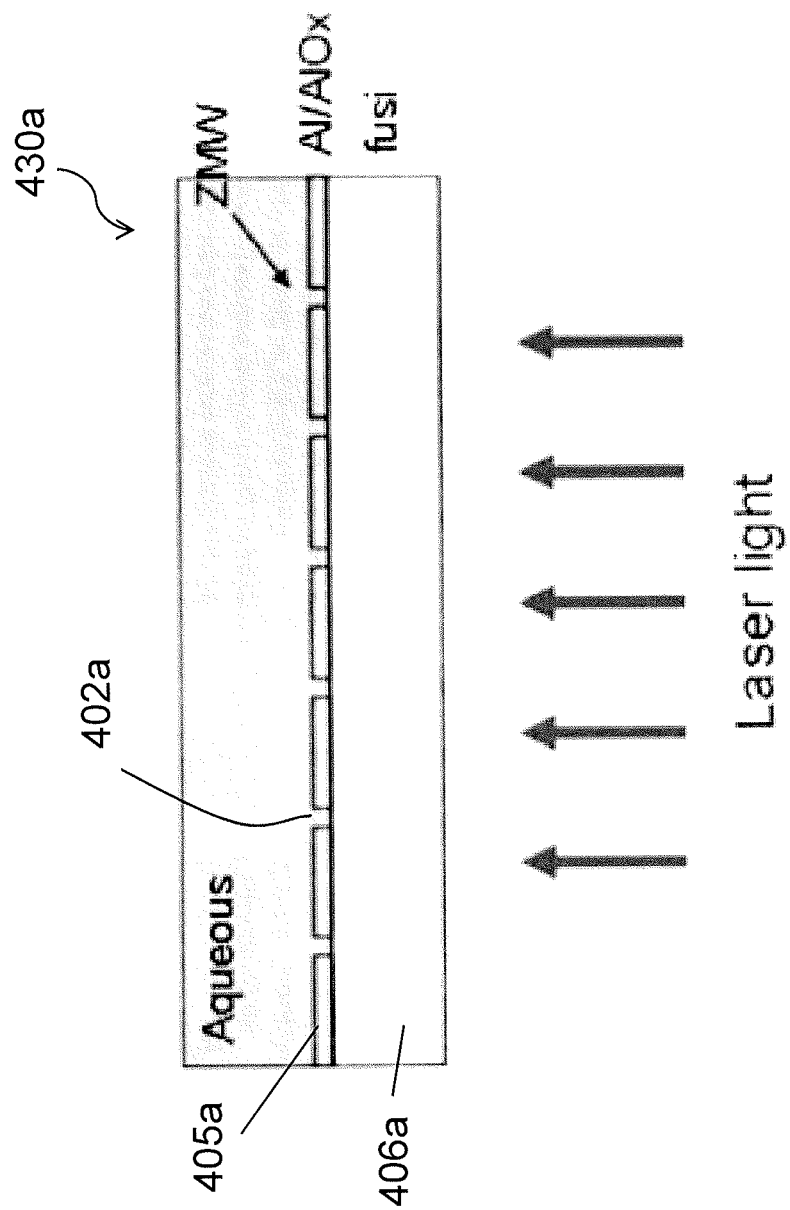
FIG. 15-FIG. 19 are several views of various devices and waveguide structures configured for laser beam excitation in accordance with the invention.
Figure 16:
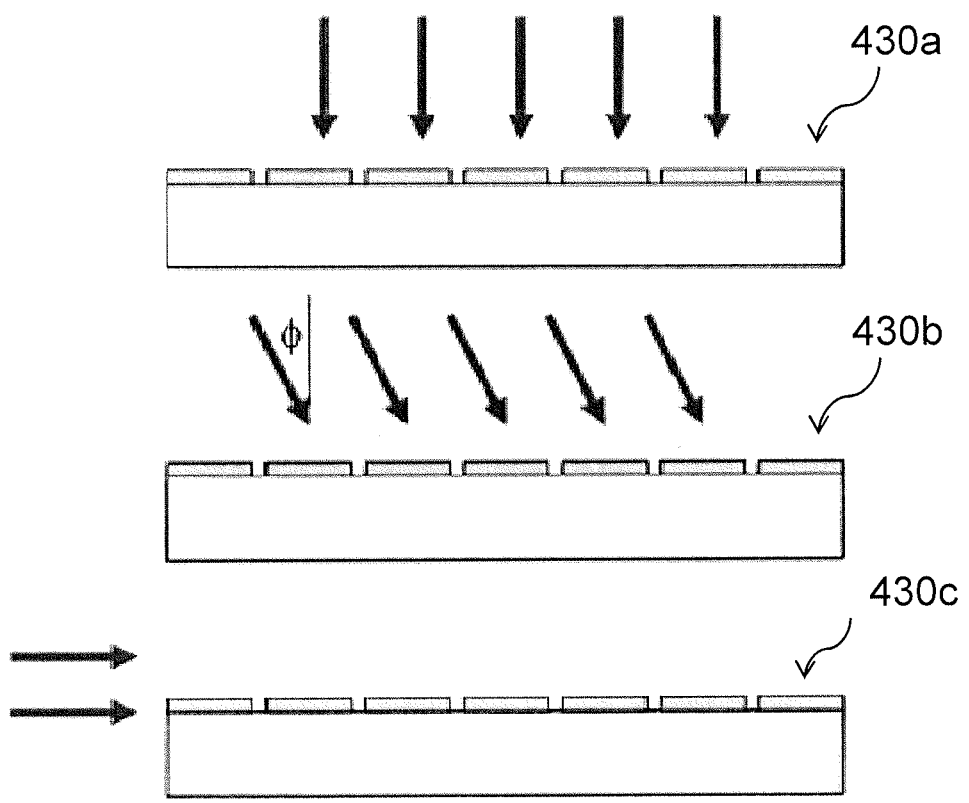
Figure 17:
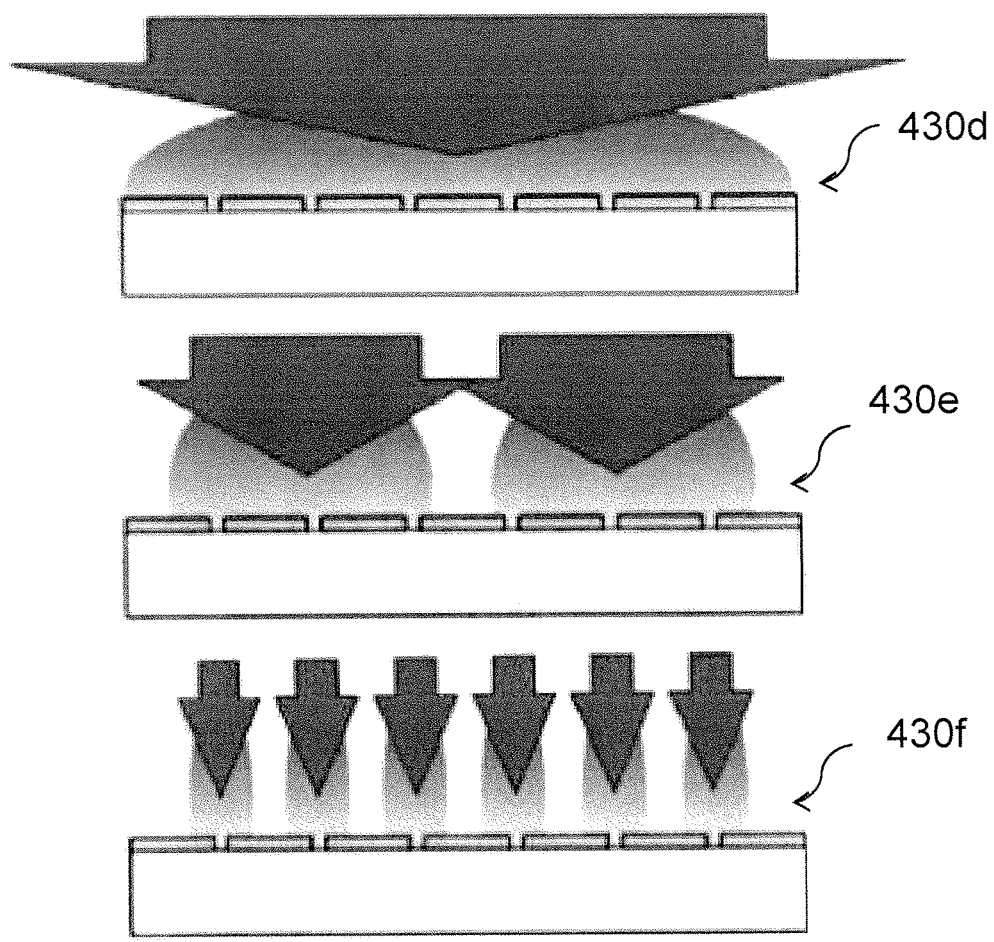

The illustrated device 430a of FIGS. 15, 16, and 17 includes a substrate 406a upon which a cladding layer 405a is deposited. A plurality of reaction cells, in the exemplary case zero mode waveguides (ZMW) 402a, are defined within spaces in layer 405a. In the exemplary embodiment, the substrate is fused silicon. Suitable materials for the cladding and ZMWs include, but are not limited to, metals and alloys, metal oxides, and composites of metals and metal oxides. In an exemplary embodiment, the ZMWs are formed of aluminum and aluminum oxide. An aqueous sample is positioned above layer 405a such that particles of interest can move into the ZMWs.

The exemplary device utilizes modified laser-based excitation strategies. In various respects, devices 430b, 430c, 430d, 430e, and 430f are configured similarly to device 430a except that the devices are illuminated with differing illumination techniques. FIG. 16 illustrates illumination from different angles and directions. FIG. 17 illustrates illumination with focused light and flood light.

With reference to FIG. 16, the illumination light may be directed into the device, and in particular the reaction cells, from directions other than from below the device (oriented with the ZMW facing up). In various embodiments, the illumination comes from above at an angle Φ relative to the top surface of the device. In another instance, excitation is provided from the side of the device. Referring to FIG. 17, the excitation is optionally provided in flood fashion (i.e. a uniform plane wave across the entire ZMW array) or as an array of two, three or more beamlets, up to the number of active ZMWs, or even more than the number of ZMWs. The illustrated device of FIG. 17 is configured similar to the device of FIG. 14 described above.

The above illumination strategies, however, may not perform well in certain sequencing systems without modification. As discussed in U.S. Pat. Nos. 7,056,661; 7,332,284; and 5,821,058, the entire contents of which are incorporated herein for all purposes by this reference, taking advantage of the photonic restriction of ZMWs generally calls for the light to hit the respective ZMW from the bottom (substrate) side, not the top (aqueous) side. As will be discussed below, therefore, a number of devices and configurations may be employed to improve system performance with such illumination strategies.

Figure 18:
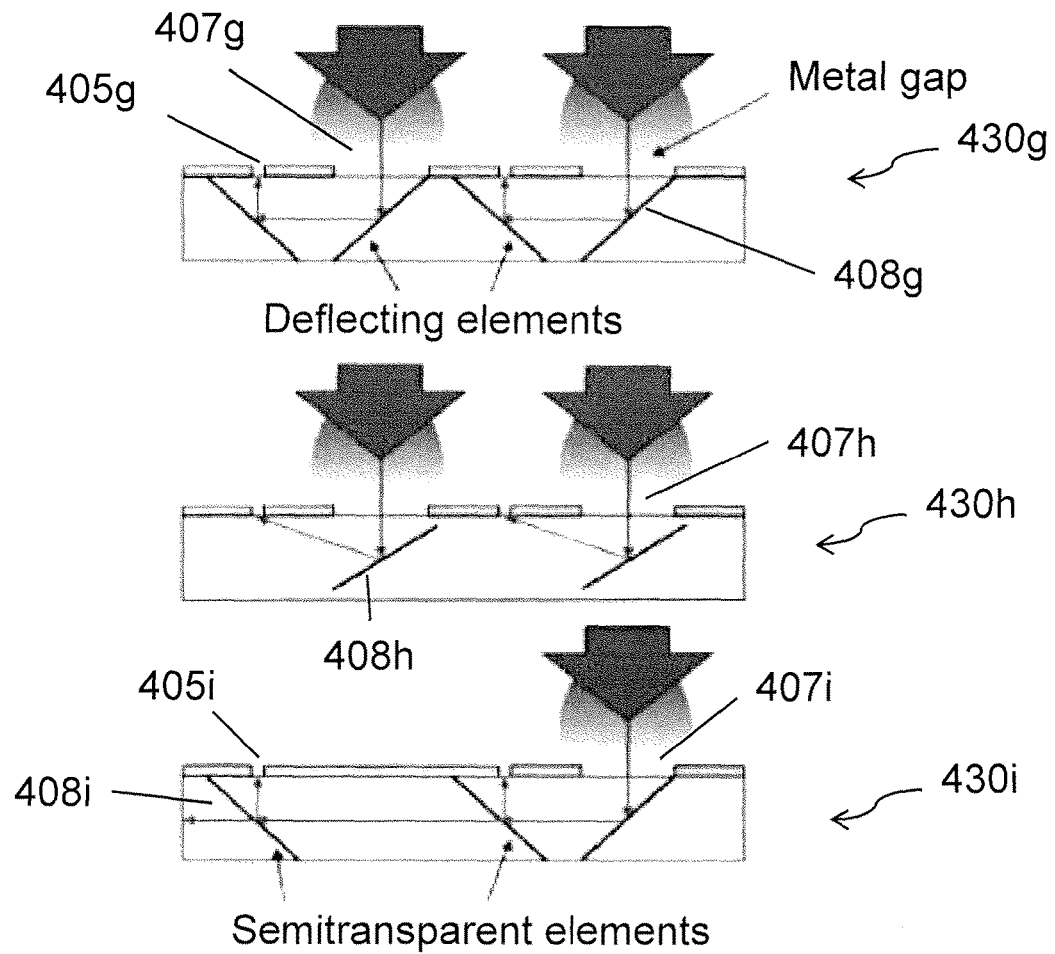

FIG. 18 illustrates a device that optionally includes relatively large diameter light pipes that extend through the metal layer and/or other configurations for allowing the light to pass through the ZMW layer to the substrate below. In the exemplary embodiment, the metal ZMW layer includes gaps 407g, 407h, and 407i that allow light to pass through and deflecting elements 408g, 408h, and 408i for redirecting the passing light to the underside of the sequencing layer. Alternatively, the device may include raised pedestals on the substrate with tops at various angles to effect the desired routing of the excitation light. Other methods for redirecting the beams/beamlets may include embedding devices in the metal ZMW layer or in the substrate.

The gaps or light pipes 407 may be dimensioned to correspond to the ZMWs. In various embodiments, the gaps or structure for allowing the light to pass through the top surface have a size equal to or greater than the size of the ZMWs, preferably twice the size of the ZMWs, and more preferably up to ten times or more times the size of the ZMWs. The optional deflecting elements include, but are not limited to, metal or semiconductor mirrors, dichroics, prisms, bragg scatterers, acousto-optic devices, and electro-optic devices. The light may be deflected to impinge on the bottom of the ZMW at a normal incidence angle or at another angle. Further, single light pipes may feed light to one or more ZMWs using semitransparent reflective elements.

Figure 19:
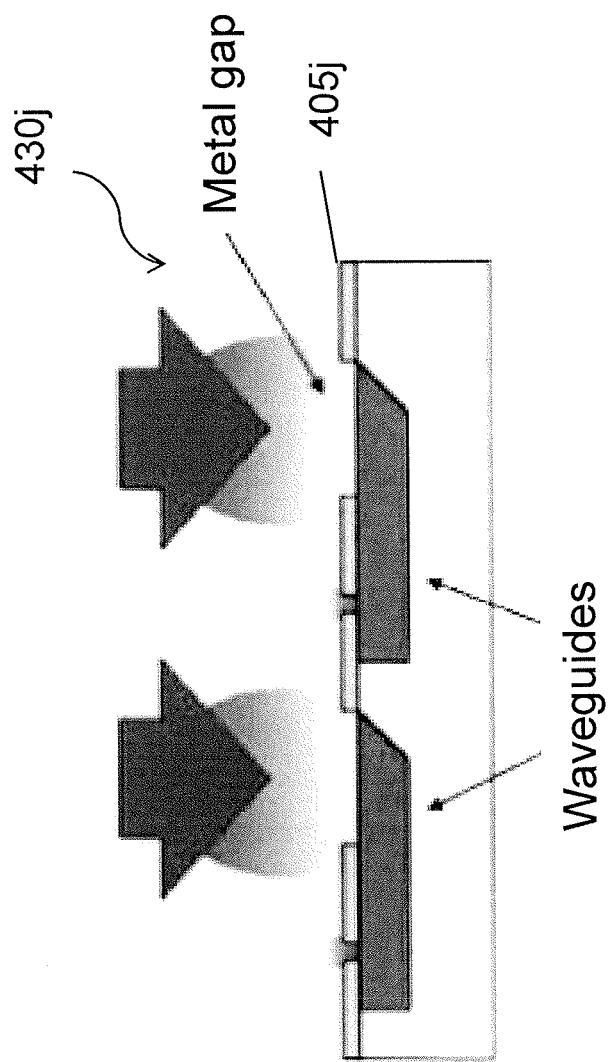

One will appreciate that other devices and configurations may be used to allow light to pass through the sequencing layer and redirected to an underside. In various embodiments, the device includes a waveguide assembly for receiving optical illumination and redirecting the illumination to one or more reaction cells in the sequencing layer. Referring to FIG. 19, for example, light is directed through gaps in the sequencing layer into waveguides extending below the sequencing layer. The exemplary waveguides are channel waveguides configured to funnel the illumination along a predetermined path below the sequencing layer. The light is optionally funneled through the waveguides to one or more respective reaction cells from below for excitation in an otherwise similar manner as described above.

Figure 20:
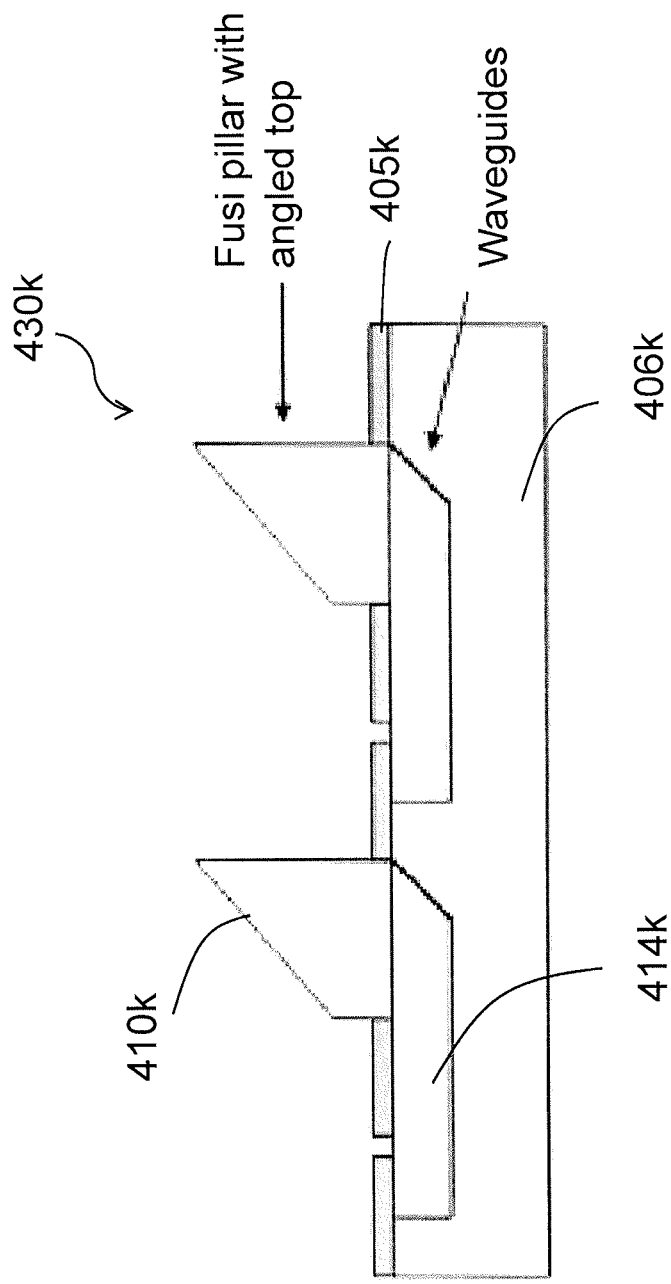
FIG. 20 is a cross-sectional view of an analytical device in accordance with the invention, illustrating optical shielding pillars for shielding the zero mode waveguides.
Figure 21:
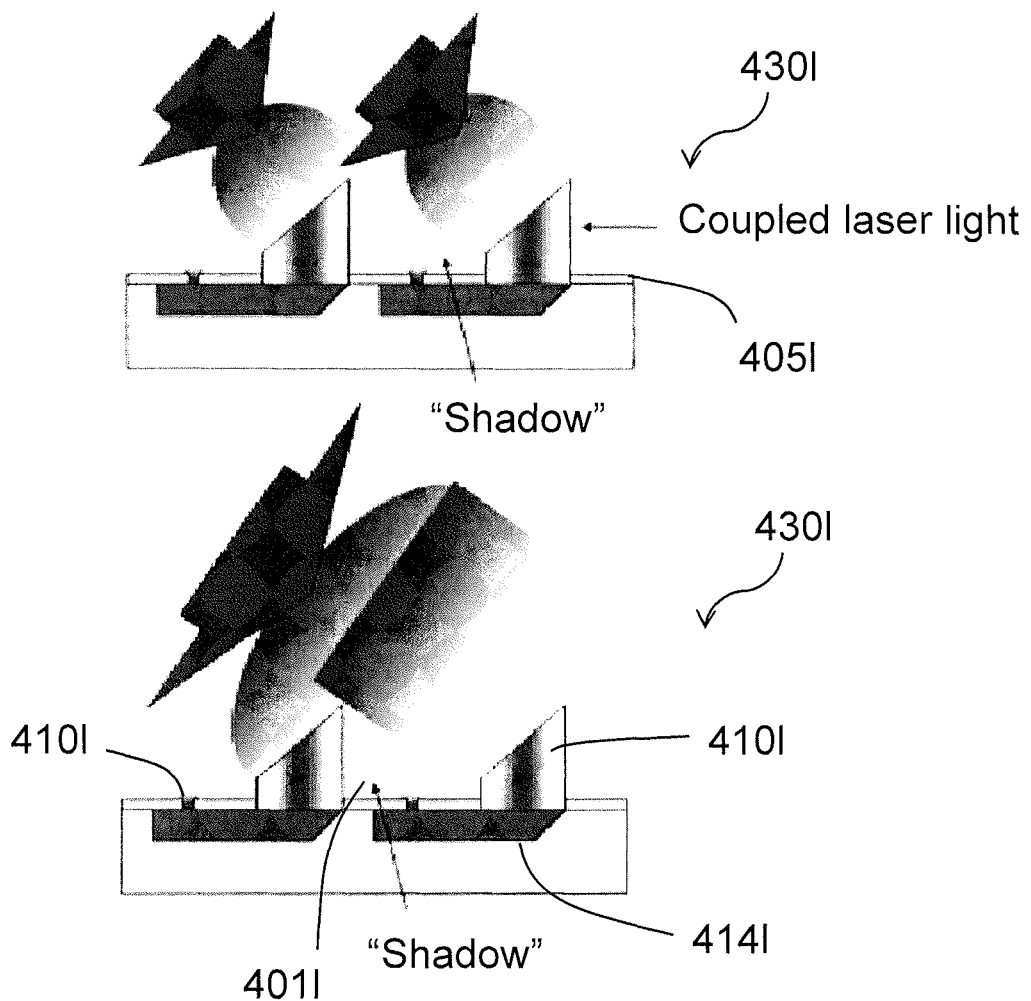
FIG. 21-FIG. 23 are several views of various device and waveguide structures configured for laser beam excitation in accordance with the invention.

Referring to FIGS. 20 and 21, light is optionally collected by pillars 410k, 410l extending upward from the substrate to a point above the sequencing layer (e.g. metal ZMW layer) 405k, 405l. The pillars may have a flat top or angled top. The top of the pillars include an illumination inlet port for receiving illumination. The exemplary top has an angle selected based on the angle of incidence of the excitation light so that the light is efficiently coupled into the pillar 410l as shown in FIG. 21. The received light then undergoes total internal reflection (TIRF) such that the pillar directs the light to a channel waveguide 414l. The waveguide then routes the light to an underside of one or more respective reaction cells. The optical pillars may extend above the sequencing layer to provide a degree of shielding of the surface. As shown, for example, in FIG. 21, the ZMWs and reaction cells 402l may be positioned in the laser "shadow" 401l of the pillar thereby more efficiently coupling the light into the waveguides and minimizing undesirable exposure of surface-bound moieties to the laser light. In various embodiments, the device includes an optically opaque cladding layer on top for shielding.

Figure 22:
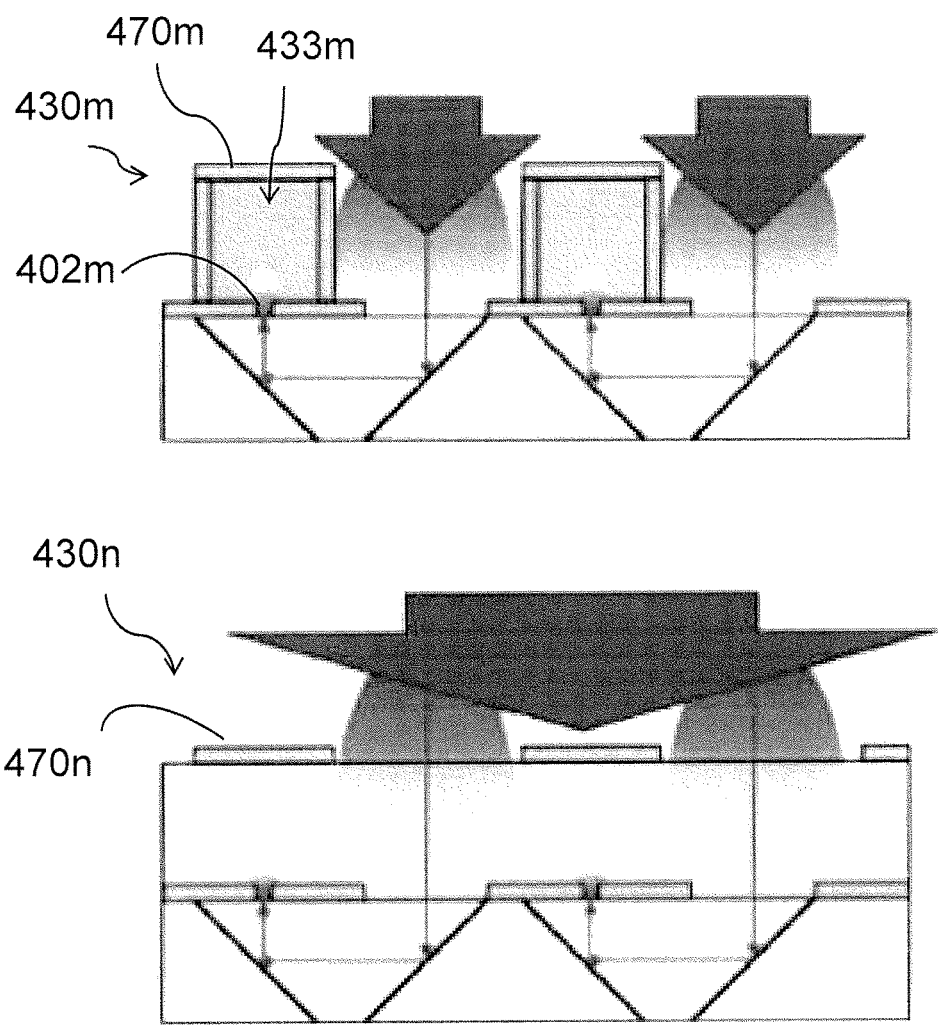

Referring to FIG. 22, ZMWs 402m, 402n and microfluidics 433m, 433n are optionally shielded from light from above with optically opaque walls 470m, 470n. In the exemplary device, the ZMWs or clusters of ZMWs are contained in separate microfluidic channels 433m, 433n having optically opaque walls configured to block incident light and shield the channel contents. The walls of the exemplary channels isolate the fluid and/or illumination housed therein. The shielding may be accomplished using various physical structures and devices. For example, the channel wall may include a thin metal coating or the device may include a dielectric stack that is reflective to the light. In another example where ZMWs and light pipes are in the same fluidic volume, an array of apertures above the light pipe array may serve to minimize the non-useful light contamination in the reagent volume.

Figure 23:
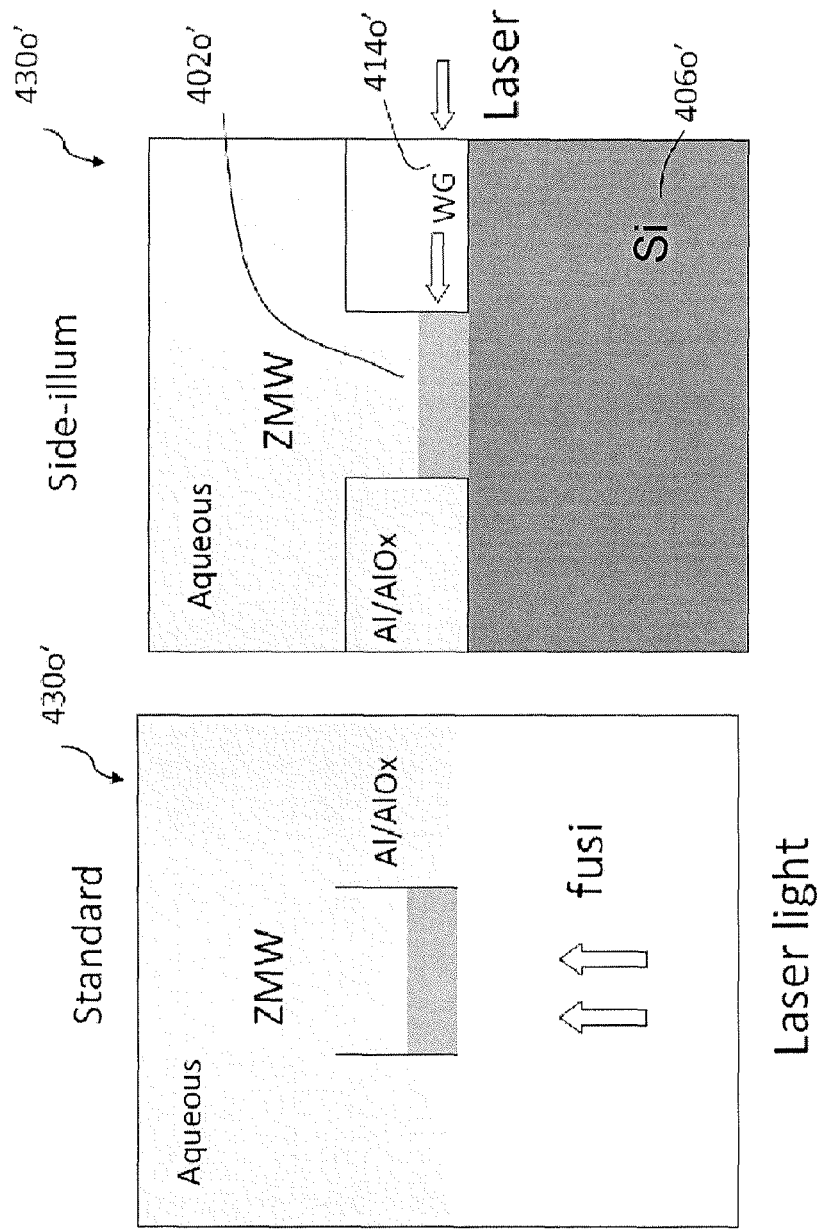

One of skill in the art will appreciate from the description herein that the ZMW illumination does not need to be directed from the bottom. Illumination may also occur from other directions such as the side. As shown in FIG. 23, an exemplary device includes a waveguide sandwiched between the metal sequencing layer that forms the ZMW 402o' and a semiconductor layer (e.g. silicon) 406o'. The semiconductor layer may include optoelectronic materials. In contrast to device 430o, exemplary device 403o' includes a waveguide 414o' that receives illumination from an edge (side) of device and directs the light to ZMW 402o'. The excitation light may be applied to sample in the ZMW from the side or bottom via the waveguide. The exemplary device provides a compact design for efficient illumination of a sample with increased illumination flexibility.

Various embodiments of the invention are directed to providing a compact device with efficient illumination. As described above, various aspects of the invention are directed to a compact, scalable system with reaction cells, sensing elements, and other functions integrated into a unified device.

Some of the description above relates to integrated sequencing sensors utilizing illumination confinement to small molecular volumes. Such techniques require compact and efficient illumination methods to operate at high resolution for low cost sequencing. One limitation of conventional devices is the undesirable rejection of source illumination. Another limitation is the difficulty of efficient routing of source illumination to the sequencing site. Both limitations may be eased with the use of through-wafer infrared illumination as discussed below.

Figure 24:
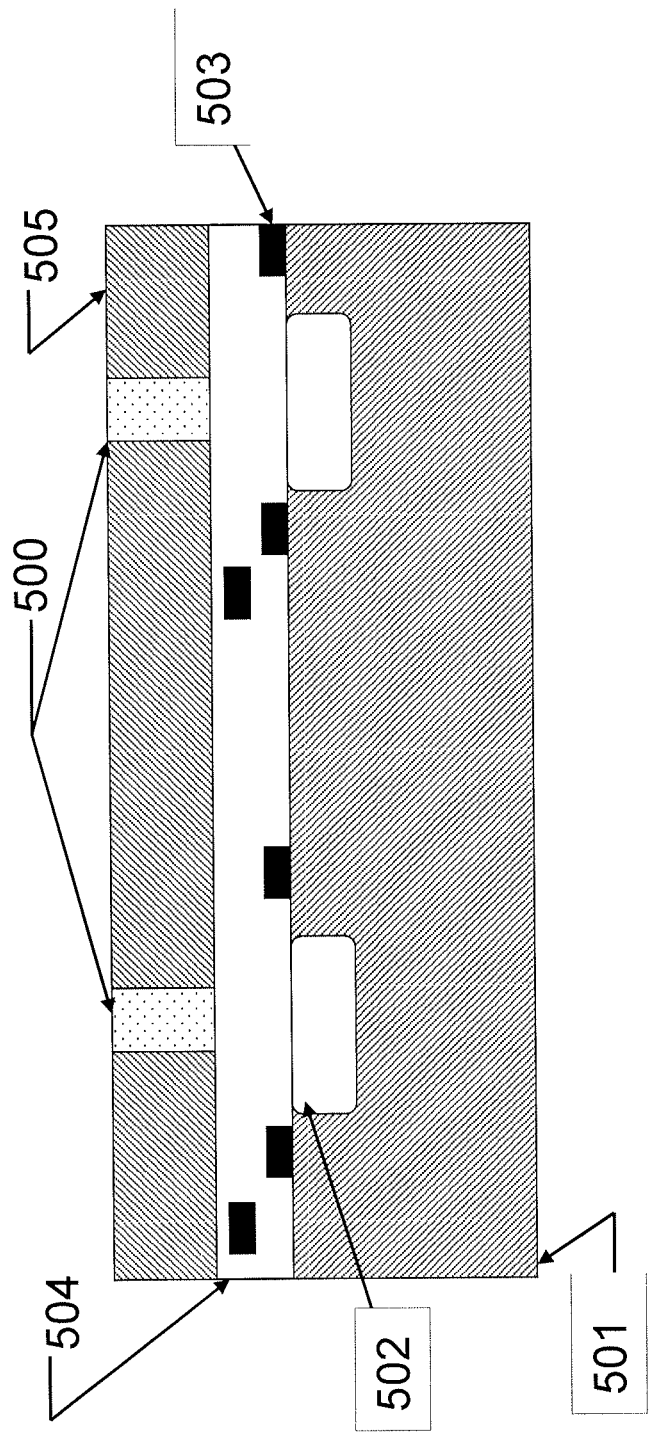
FIG. 24-FIG. 26 are several views of various integrated devices and patterned waveguide structures in accordance with the invention.
Figure 25:
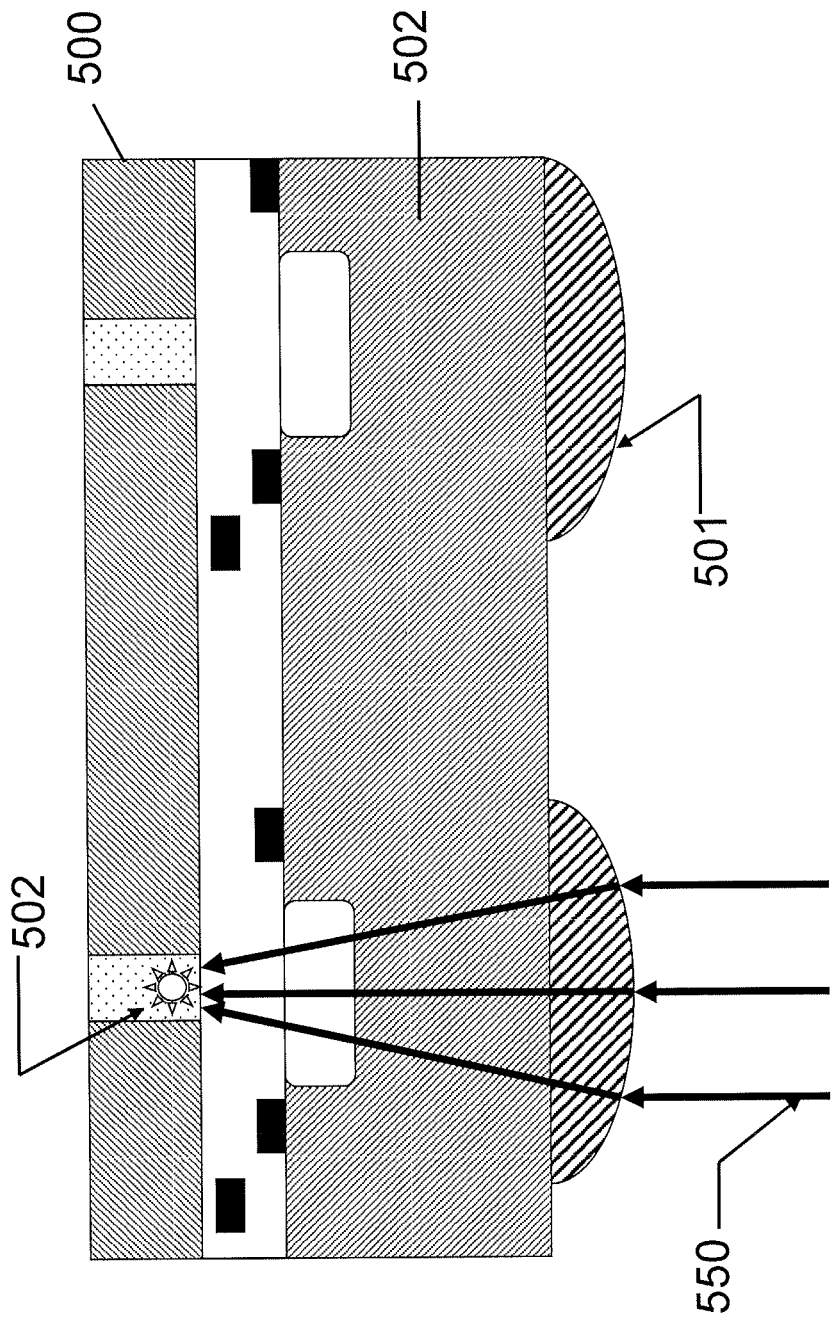
Figure 26:
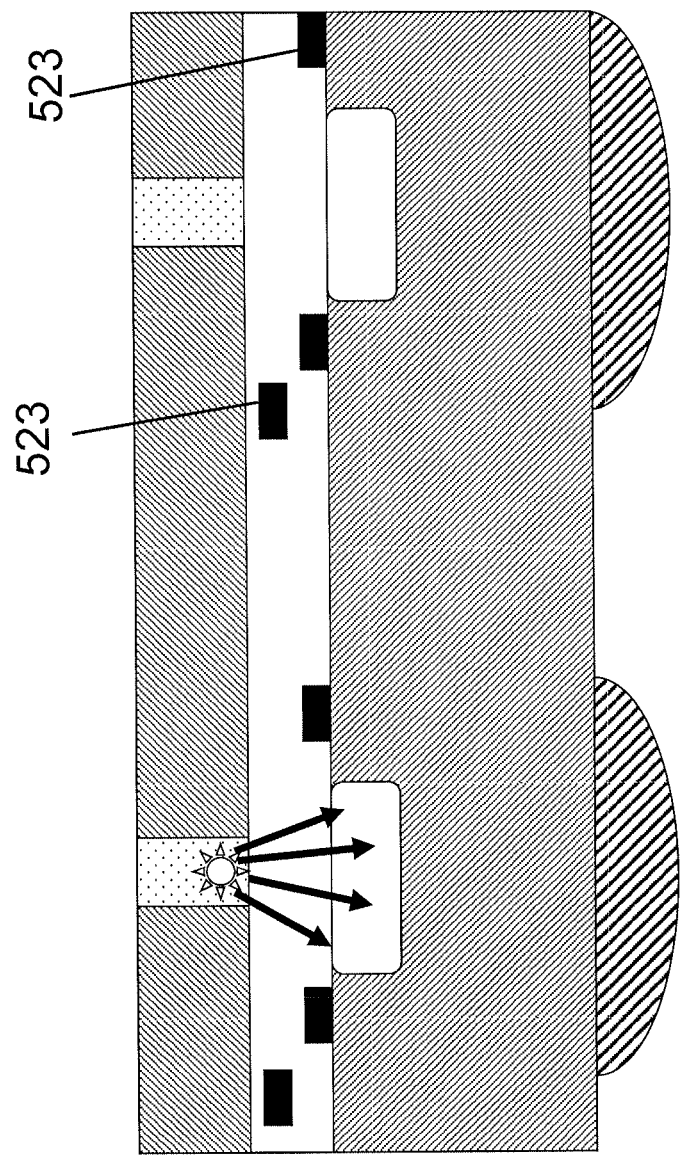

Turning to FIGS. 24, 25, and 26, another exemplary device configured for efficient illumination in a compact architecture is shown. The exemplary optode device is configured for introducing an excitation signal from below the device, and in particular, the detection layer. FIG. 24 is a cross section of the exemplary integrated device. The device includes a substrate 501 with patterned photodetectors 502. The substrates and photodetectors can be a single device or an array of one, two, or more dimensions of arbitrary resolution. These photodetectors are arranged with conductive readout busses 503, which typically are opaque to radiation. Metal conductors are arranged in an insulating layer 504. In various embodiments, the insulating layer is made from an oxide dielectric and transmissive to optical radiation frequencies. The exemplary integrated device includes a sequencing layer which is made from very small volume optical cavities 500 arranged over the photodetectors 502. These volumes 500 are made from a top layer 505. In an exemplary embodiment, the cavities 500 define reaction cells for capturing a set of reactants. The exemplary sensor elements are positioned essentially below corresponding reaction cells and in optical communication with the reaction cells. In various embodiments, the top layer is essentially optically opaque and biocompatible with any required surface treatments to facilitate the sequencing chemistries.

In contrast to conventional devices, the exemplary device has at least partially overlapping illumination and detection pathways and is configured for receiving illumination from the bottom of the device through the detection layer. As shown in FIG. 25, the exemplary device is configured such that the illumination is directed from below the device through a sensor element 502 on the way to the reaction cell 500. As shown in FIG. 26, at least some of the emitted light is directed in generally the opposite direction to the sensor element 502 where it is absorbed.

The top surface of the device includes an optically opaque layer such as a cladding layer. The sequencing layer is optionally provided with a transparent substrate and a plurality of nanoscale apertures extending therethrough. Each aperture is separated by regions of transparent substrate. A layer 501 is provided below the sequencing layer. The exemplary layer 501 includes electrical vias and fluidic conduits, generally designated 523. A detection layer is provided below layer 501. A plurality of sensor elements 502 are disposed in the detection layer. A waveguide may be optionally integrated into the device to direct illumination to the reaction cells.

The exemplary device is configured for use with upconverting dyes. Generally, upconverting dyes absorb wavelengths longer than their emission wavelength. Through multiple photon absorption, they generate higher energy output photons. U.S. Pat. No. 7,056,661, previously incorporated herein, discloses an exemplary polymerase provided with a donor fluorophore that is excited at a first wavelength and emits at a second wavelength while the nucleotide to be added is labeled with a fluorophore that is excited at the second wavelength but emits at a third wavelength.

In general, the reactants include a dye or similar material that receives illumination of a first energy level and emits illumination at a higher second energy level in response. In various embodiments, the set of reactants delivered to the reaction cell includes an upconverting phosphor for receiving two or more photons of a first energy level and emitting fewer photons of a second energy level in response, the second energy level being greater than the first energy level. In various embodiments, the phosphor dye receives two or more photons and emits a higher level signal in response. In various embodiments, the dye receives one or more photons and combines the photons into a few number of photons having a longer wavelength (higher energy level).

In operation, the illumination light 550 is directed to the reaction cell 500 along an illumination (transmission) pathway under sufficient conditions to cause the phosphor to emit a detection signal. The exemplary transmission optical path is shown in FIG. 25. The exemplary return optical path for the dye emission is shown in FIG. 26. The emitted rays are absorbed by the upconverting dye 502'.

The exemplary device receives a dye having an emission wavelength selected near a detection edge of the sensor. In general, the dye receives illumination at a first energy level and emits a detection signal at a second, higher energy level. Whereas the sensor element is transmissive at the first energy level, the emitted detection signal is at a sufficient energy level such that it is absorbed by the sensor element. In this manner, illumination may be directed into the device from below the chip and through the sensor element. This technique also provides a compact design by combining the transmission and detection into integrated pathways.

The exemplary device is designed, in part, based on the general principle of selecting the dye wavelength near the detection edge of the photodetector and substrate. In other words, the stimulus wavelength is transmissive to the detector layers while the emitted wavelengths are absorbed by the detector layer. This can be accomplished by adjusting at least one of the illumination wavelength, detector, and dye based on the others. One will appreciate that this provides a method to advantageously illuminate the sequencing layers through the detector layer and utilize an identical (but opposite direction) path for emission and detection. By utilizing a common path, a simpler device can be produced at lower cost and decreased space requirements (e.g. vertical profile).

FIGS. 25 and 26 illustrate various other components for routing illumination in the exemplary device. In various embodiments, focusing elements aligned during manufacture are used to increase efficiency. In FIG. 26, an optional microlens 501' is patterned on the back surface of a wafer 501 and directs light rays 550 towards the sequencing layer 500.

As will be appreciated from the description herein, the above technique can also be used to route illumination away from the opaque conducting layers and other components, for example, to increase efficiency or introduce light scattering sites. As shown in FIG. 25, for example, a focusing element directs the illumination through the sensor element into the reaction cell and away from the cladding material. In various embodiments, the focusing element is patterned in the conducting layer with index gradients (e.g. nitride or air gap) or using metal or other reflective guiding devices. In various embodiments, back surface illumination is achieved with hybrid assemblies and/or techniques described herein. For example, back surface illumination may be achieved with self-aligned optical assemblies described above.

Figure 27:
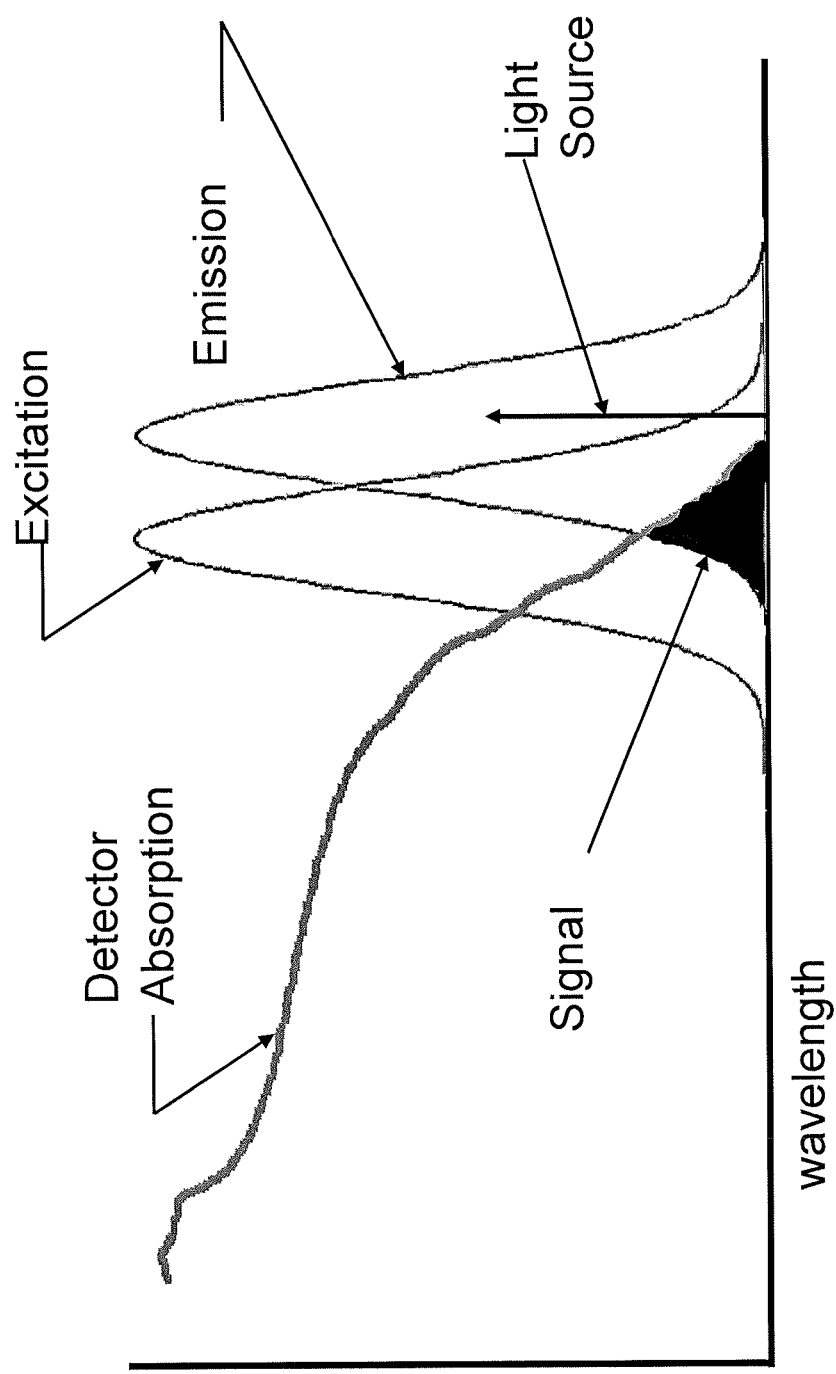
FIG. 27 is a plot diagram of illustrating detector layer filtering using the downconverting tail technique in accordance with the invention.

With reference to FIG. 27, one will appreciate that the above techniques can be used with a downconverting tail technique, in which the longer wavelength tail of the dye absorption is used with the short wavelength tail of the emission distribution to enable detector layer filtering.

Figure 28:
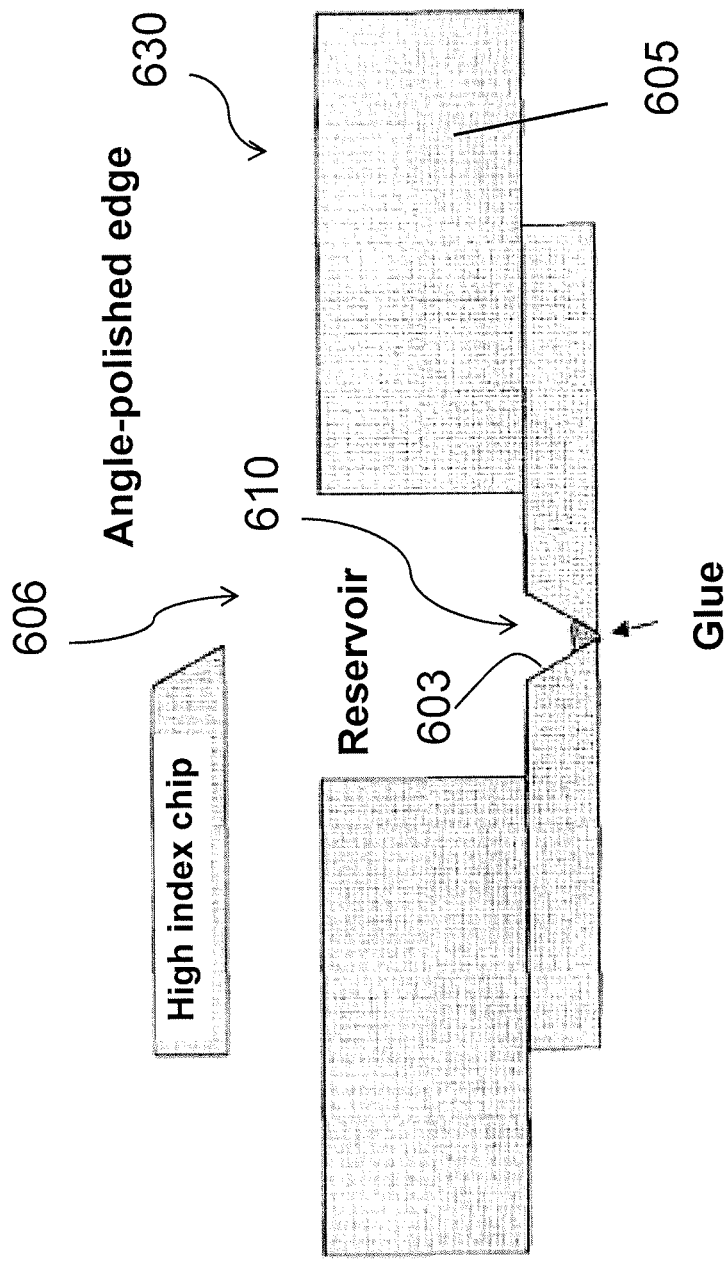
FIG. 28 is a cross-sectional view of an analytical device in accordance with the invention, illustrating use of notches and wedges for directing illumination light.

Various other optical components may also be provided on or integrated into the analytical device for routing and adjusting the illumination signal. FIG. 28 illustrates an exemplary device 630 that makes use of total internal reflection (TIRF) techniques. Conventional TIRF methods generally require either a prism for coupling high-angle radiation to a substrate or through-the-lens coupling of marginal rays above the critical angle of total internal reflection. Both conventional methods may have drawbacks. For prism TIRF, much of the emitted radiation is lost because the emission is biased in a direction away from the objective lens. In through-the-lens TIRF, high angles are not generally achievable in high index materials. Therefore, a method of doing through-the-lens TIRF with high angles of incidence as described herein is thus desirable.

In the exemplary device of FIG. 28, a substrate 605 is modified with notches 601 with angled sidewalls 603 to redirect light that is incident near the zero angle to very high angles of incidence, irrespective of the index of the substrate. In various embodiments, the angle of incidence is below the critical angle for TIRF and the notches redirect the light at an angle above the critical angle. In various embodiments, the angle of incidence is below the critical angle for directly illuminating the sample and the notches redirect the light at a sufficient angle for illumination.

The notches need only be wide enough to allow the beam to be directed toward the region of interest while allowing sufficient optical resolution of the ROI from region 606 (also referred to "bank-shot region"). The quality of the surface generally must be sufficient to get an appreciable amount of energy at large incident angles. Although described as notches, one will appreciate that other guiding mechanisms may be used in accordance with the invention.

Figure 29:
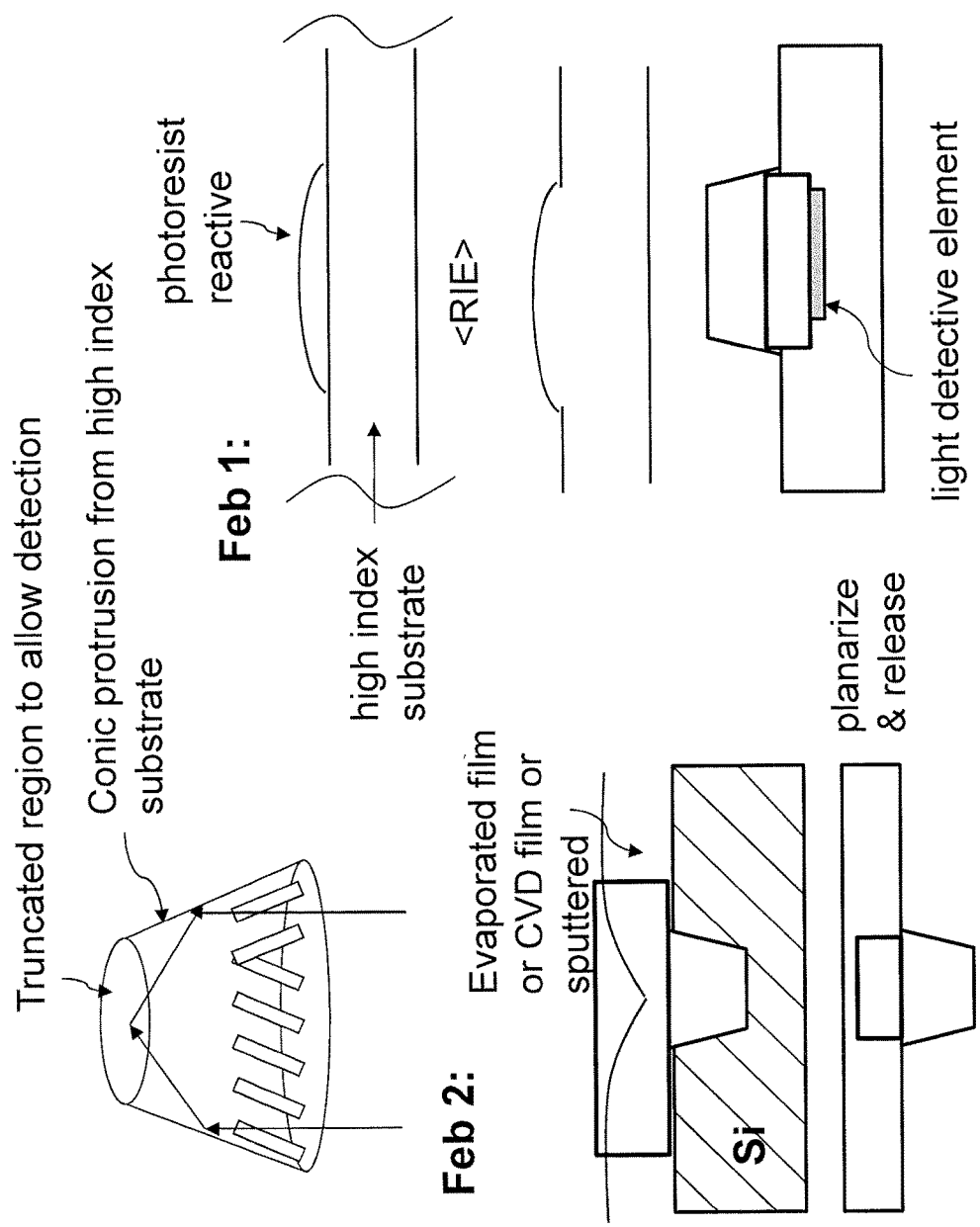
FIG. 29 is several views of methods of making analytical devices, illustrating various techniques and configurations for directing illumination light.

FIG. 29 illustrates other optical components for adjusting, manipulating, and controlling the direction of the excitation light in accordance with various aspects of the invention. The exemplary devices are made using a variety of techniques which include grinding the material with v-shaped cutting edges, photolithography with variable depth pattern transfer, wet etching with undercut, and other methods. In another embodiment of the invention, a notch in a transparent substrate is formed by polishing the edge of a flat plate of glass at an angle, then affixing two such slides to a reservoir so that the acute angles formed at the edge are in close proximity or in contact. An hermetic seal is then achieved by placing a small quantity of curable sealant in the cleft formed between the two plates, which will then form a seal by capillary action across the entire length of the joint. One will appreciate that other modifications will be within the scope of the invention. For example, the angle of the bank shot surface, the width, the presence or absence of a partner surface, and other modifications may be made.

In another aspect of the invention shown in FIG. 29, an exemplary device is formed of a high index of refraction base substrate. In operation, illumination light is directed into the substrate to cause dark-field illumination or total internal reflection illumination (TIRF) of the top surface. The top surface includes zero mode waveguides (ZMWs) fabricated from a lower index of refraction material. The illumination creates the same observation volume confinement created in regular ZMWs, but the transparent nature of the top surface layer reduces scattering of the incident light. Suitable materials for the substrate include, but are not limited to, lithium niobate, zirconia, diamond, and other high index mediums capable of being machined.

In the exemplary device, wedges with angled sidewalls are ground into the substrate to promote total internal reflection (TIRF). The wedges are machined in the substrate and include conical features on the surface configured to generate a focusing effect around the zone in which TIRF is to be created. This allows more efficient use of the incident radiation. This may also reduce background light from auto-fluorescence and stray laser light. These conical features and wedges can be fabricated by surface micromachining, thin film evaporation, and the like.

In various embodiments, a small light-blocking element is included with the device for blocking direct light path to the zone of detection and preventing light from being refracted into the liquid medium containing the analyte, thus reducing background radiation. In various embodiments, the light reflecting surfaces are slightly concave (i.e. deviating from a true conical shape) thereby allowing additional focusing so a single point can be either transmitted directly to a detection system or reflected off the conical or nearly conical surfaces to be directed towards the detector. In this way the numerical aperture of collection may be greatly increased. This may have importance in fluorescence emission systems near high index media due to the directional nonuniformity of emission.

As will be appreciated from the description herein, because the devices of the invention are generally amenable to fabrication using standard monolithic semiconductor fabrication techniques, fabrication of the devices can also incorporate many of the functional components that are employed for the illumination and detection elements, e.g., the electrical interconnects and busses used for a CMOS sensor array as well as the optical components (e.g. optical tunnels, lenses, mirrors, etc.) and even the reaction cells themselves (e.g., metal clad ZMWs). In addition, other functional elements may be integrated using the same or similar processes, including, for example, microfluidic elements that may be integrated into the overall device structure, and illumination components such as for delivery of excitation illumination to the reaction cells.

As referred to above, in some cases, illumination optics are included within the integrated device structure. These optics may include actual illumination sources, e.g., LEDs, solid state laser components, or the like. They may also include optical conduits for transmission of excitation illumination from either an internal or external light source to the reaction cell. Examples of optical conduits include waveguides integrated into the substrate adjacent to the reaction cell. Examples of such illumination conduits have been previously described in, e.g., published U.S. Patent Application No. 2008-0128627, the full disclosure of which is incorporated herein by reference in its entirety for all purposes.

Similar fabrication processes may be employed to provide higher index of refraction (IR) material tunnels from the reaction cell to the sensor element, or devices that include a hybrid of a high IR tunnel component and a reflective (e.g. metal) optical tunnel. In an exemplary embodiment, one or more intermediate layers are provided with regions of higher index of refraction. These regions are of sufficiently high IR relative to the surrounding substrate material so that they funnel light to the detector and/or reaction cell by virtue of maintaining total internal reflection within the higher IR region. By way of example, if the high IR region possesses an IR of e.g., 2.04, such as is the case for a silicon nitride plug, that is disposed through and interfaced with an intermediate layer having an IR of 1.64, e.g., as in silicon dioxide, it would result in total internal reflection of any light impinging that interface at less than 30 degrees. As will be apparent from the description herein, a variety of methods are available for providing high IR regions precisely located within the substrate layer and other layers may be used including, but not limited to, etching followed by nitride deposition (e.g., liquid phase chemical vapor deposition (LPCVD)). Other index shifting materials may be included in the fabrication of the device, including, for example, doped silica materials, e.g., nanocrystal doped components or materials (e.g., U.S. Patent Application No. 2007-0034833, the full disclosure of which is incorporated herein by reference in its entirety for all purposes), and/or air or other gas-filled gaps or spaces to provide index mismatch to guide optical signals. In various embodiments, the device includes optical tunnels with confined cavities. The optical cavities may be useful in a variety of ways depending upon the nature of the application and architecture of the device. For example, such cavities may provide additional signal funneling to a detector or sensor element. Alternatively, the cavities may be configured as an illumination conduit for delivery of illumination radiation to a reaction cell.

In various embodiments, the illumination source is remote and directed into the device with various optics. In various embodiments, the illumination source is reversibly optically coupled to the illumination ports. By "reversibly optically coupled" it is meant that one element, which is functionally coupled to another element, may be removed. In other words, the coupling is not permanent. As used herein, for example, the illumination source may be connected and disconnected from the illumination port using quick disconnect ports and the like.

VI. Detector Components

As noted previously, in some applications, it may be desirable to distinguish different signal components, e.g., to identify that both a reaction has occurred and to identify the participants in that reaction. By way of example, in the case of nucleic acid sequencing, one can provide different nucleotides with different optical labeling groups thereby allowing not only detection of a polymerization reaction but also identifying the particular type of nucleotide that was incorporated in that polymerization reaction. Accordingly, it would be desirable to include the ability to distinguish different signal components within the devices and/or systems of the invention.

In some optical systems, the ability to distinguish different signal components is achieved through the use of, e.g., different filtered optical trains, or the inclusion of dispersive optical elements to differentially direct different spectral components of a signal to different detectors or different regions on a given detector array. In various embodiments, the system is configured for detection and differentiation based on other detection techniques. Various aspects of the detection devices and methods are similar to those described in U.S. Patent Publication Nos. 2007/0036511 filed Aug. 11, 2005, 2007/0036511 filed Aug. 11, 2005, 2008/0080059 filed Sep. 27, 2007, 2008/0128627 filed Aug. 31, 2007, 2008/0283772 filed May 9, 2008, 2008/0277595 filed Sep. 14, 2007, and 2010/0065726 filed Sep. 15, 2009, and U.S. Pat. Nos. 7,626,704, 7,692,783, 7,715,001, and 7,630,073, the entire content of which applications and patents are incorporated herein for all purposes by this reference.

In the context of integrated devices, the available space for use in differential direction of signal components is generally reduced. Similarly, where a single sensor element is assigned to a reaction cell, one may be unable to direct different components to different detectors.

The integrated device may include directional components and/or filter components that selectively direct different spectral components of a signal to different adjacent pixels or sensors within the device. By way of example, a given reaction cell and its associated optical train may include multiple individual sensor elements associated with it, e.g., pixels. Included within the optical train would be a directional component that would direct spectrally distinguishable signal components to different sensor elements or collections of sensor elements. Examples of such components include prisms, gratings or other dispersive elements that can redirect and separate signal components. The use of such components in optical systems is described in, e.g., published U.S. Patent Application No. 2008-0226307, the full disclosure of which is incorporated herein by reference in its entirety for all purposes.

As noted previously, although generally illustrated in terms of individual or a few reaction cells and associated integrated optical components and sensors, it will be appreciated that the illustrations and descriptions provided herein apply to much larger arrays of such reaction cells. In particular, such devices may generally have integrated into a single device more than about 1000 discrete reaction cells, and associated optics and sensors. In various embodiments, the integrated device includes a number of reaction cells in a range selected from between about 1000 and about 1 million, between about 2000 and about 1 million, between about 1000 and about 100,000, between about 100,000 and about 1 million, between about 1 million and about 10 million, and more than 10 million. It may be desirable to select the number of reaction cells based on the desired application. For example, the device may include between about 1000 and about 100,000 cells for clinical testing, between about 100,000 and about 1,000,000 for a diagnostic laboratory, or more than about 1,000,000 for high throughput research.

In accordance with the invention, each reaction cell may have an individual sensor element or pixel associated with it, or it may have multiple sensor elements or pixels associated with it (particularly where spectral separation, direction and separate detection are warranted). Likewise, each reaction cell may preferably have its own dedicated integrated optical components associated with it. In some cases, integrated optical components may be shared among multiple reaction cells, e.g., to apply standard filtering, to apply illumination to multiple cells, or the like, and will typically be in addition to one or more dedicated optical components.

In accordance with the present invention, in addition to integration of the sensor and reaction cell elements within a single analytical device, one or more optical components may be included within the device. Examples of integrated optical elements include, but are not limited to, directional optical elements, i.e., optical elements that alter the direction of optical signals to direct those signals at or to a sensor element or another optical element. Such elements include, e.g., mirrors, prisms, gratings, lenses, and the like. By way of example, in certain cases, parabolic reflector elements or micro-mirrors are integrated into the device to more efficiently direct optical signals in a given direction (See, e.g., U.S. patent application Ser. No. 12/567,526, filed Sep. 25, 2009, incorporated herein by reference in its entirety for all purposes). Other optical elements include spectral elements, e.g., elements that alter the spectral characteristics of the optical signals including directing spectral components of a signal or set of signals in differing directions, separating a signal into different spectral components, or the like. These elements include, for example, dichroics, filters, gratings or prisms that separate a given signal into spectral constituents.

In various embodiments, such optical components include contained optical enclosures that efficiently collect photon signals emanating from the reaction region and that are incident over a wide emission angular distribution, and direction of those signals to an assigned sensor element or elements. Such self-contained enclosures typically provide trapping within the chamber of substantial amounts of the photons emitted from the reaction region, elimination of cross talk between reaction cells or regions that would otherwise result from scattered signal entering adjacent sensor elements, reduction in leakage current since the sensing elements can be made extremely small, reducing scattering paths and scattering elements within each optical chamber, and reducing auto-fluorescence due to the substantially reduced optical path mass and eliminated free-space interfaces.

In addition to such directional optical elements, or as an alternative to such elements, multiple sensor elements may be provided with filtering optics that allow only a single signal type to reach that particular sensor element. Each sensor is differently filtered to allow it to detect a particular signal component, to permit multicolor distinction. In particular, each of a plurality of sensor elements within a given reaction cell's dedicated optical train is provided with a filter that narrowly passes one component of the overall signal from the reaction cell. For example, the signal associated with a given nucleotide incorporation event would be passed by a filter on a first pixel element, but rejected by the filter on three other adjacent pixel elements. Each of the different filter layers on each sensor would be selected for the given signal components for a given application. Further, each reaction cell could have one, two, three, four, or more pixel elements dedicated to receiving the signals from that reaction cell. In some cases, 5, 10, 20, 50 or even 100 pixels or more could be devoted to a given reaction cell.

Deposition of a variable filter layer, i.e., providing different filters on different pixels or collections of pixels, may generally be accomplished during the fabrication process for the overall integrated devices or the underlying sensor elements using conventional CMOS fabrication processes.

Likewise, dichroic filters are equally amenable to fabrication/patterning onto the sensor elements to reject any potential excitation illumination.

Alternatively, or in addition to selective direction/filtering of the output signals from a reaction cell, distinguishing signal components may also be accomplished by detecting an output signal in response to a specific excitation event. In particular, if a signal is received in response to an excitation radiation that is specific for a given signal generator, e.g., fluorescent label, one can assume that the label is present. By modulating or interleaving the excitation illumination across the excitation spectra for multiple fluorophores having differing excitation spectra (or different excitation/emission profiles), one can identify when any of a set of fluorophores is present in the reaction cell. By correlating an emitted signal with a given excitation event, one can identify the fluorophore emitting the signal. Examples of this process are described in published U.S. Patent Publication No. 2009/0181396, the full disclosure of which is incorporated herein by reference in its entirety for all purposes. As will be appreciated, the timing of illumination, the frame rate of the detector, and the decay times for the fluorophores may be matched to provide optimal detectability of each different signal event, without different events bleeding over into each other, while also permitting sufficient sampling during a given frame capture event for the detector so individual events are not missed.

Figure 30A:
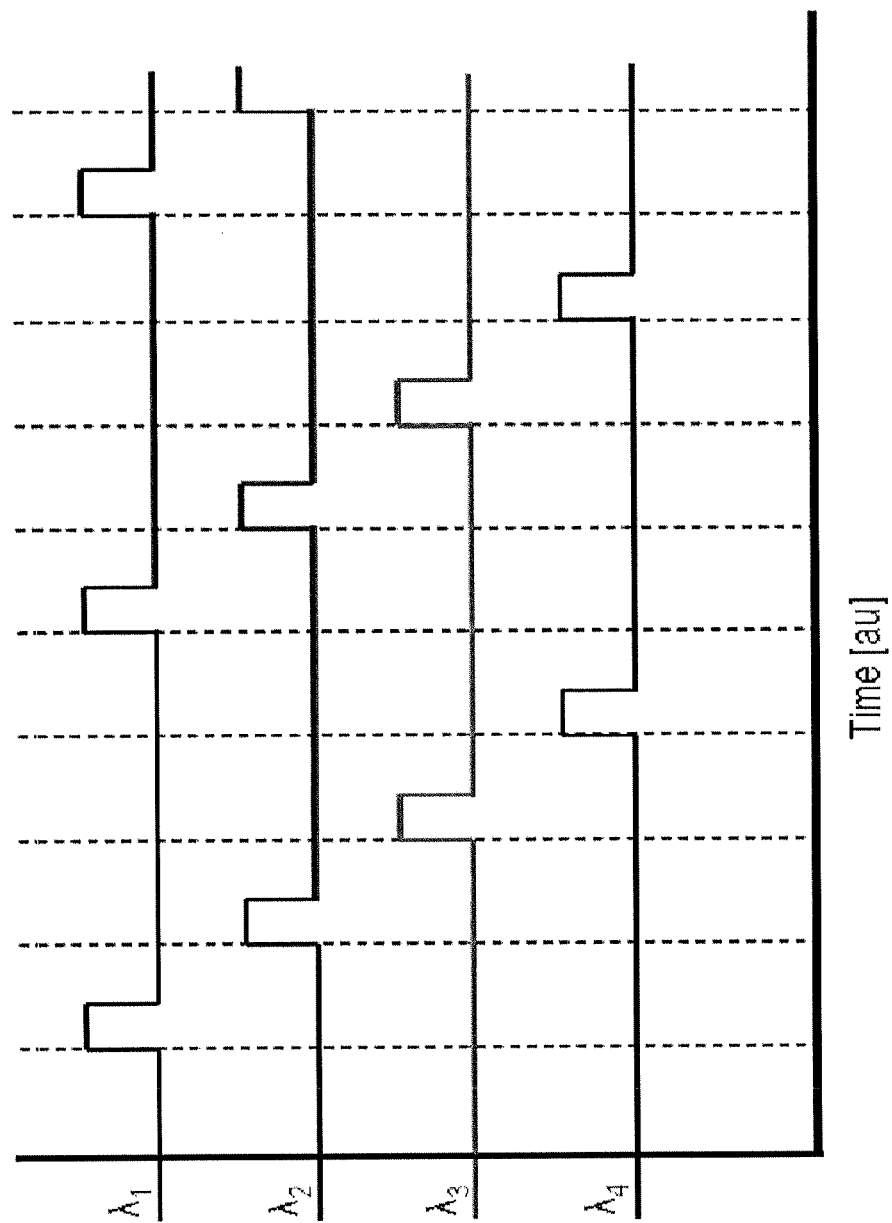
FIG. 30A-FIG. 30C show exemplary plots of interleaved excitation illumination and signal data using a system similar to that of FIG. 3.
Figure 30B:
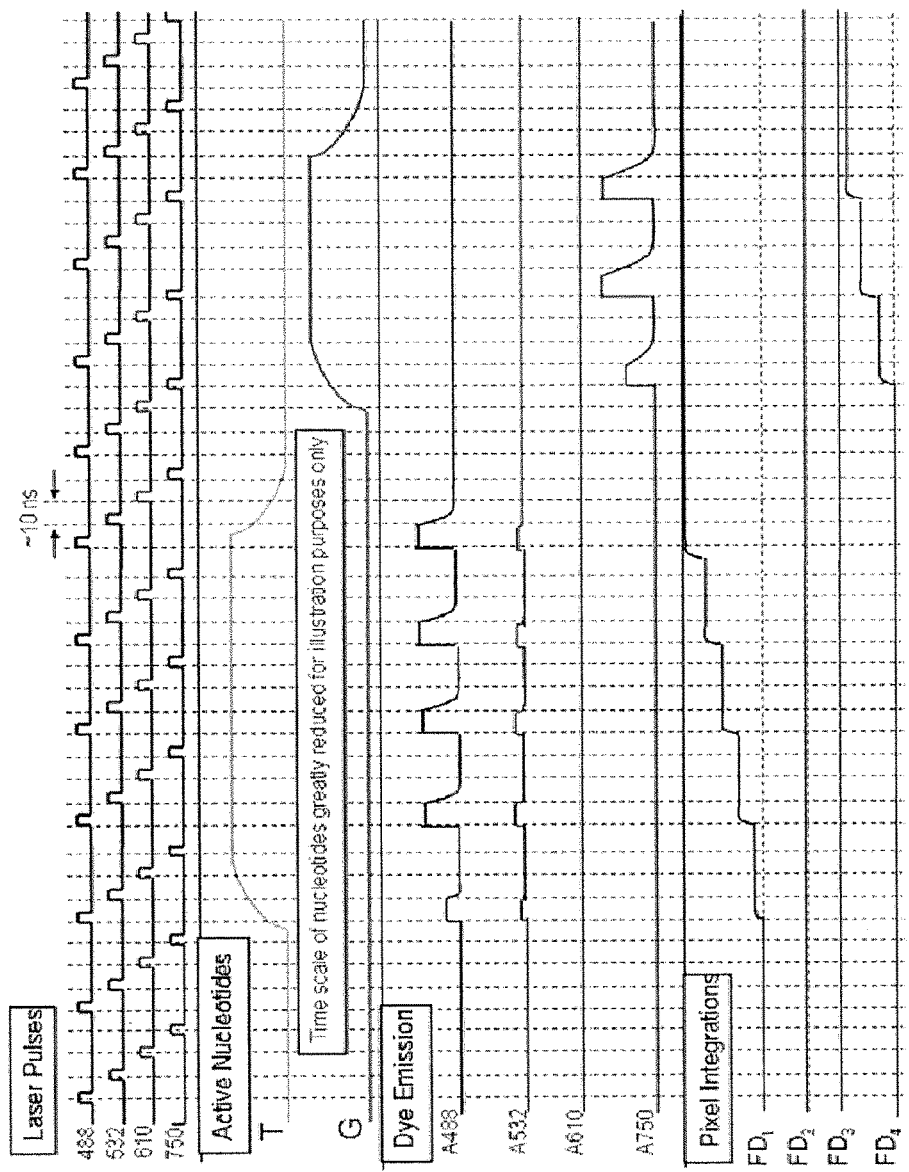
Figure 30C:
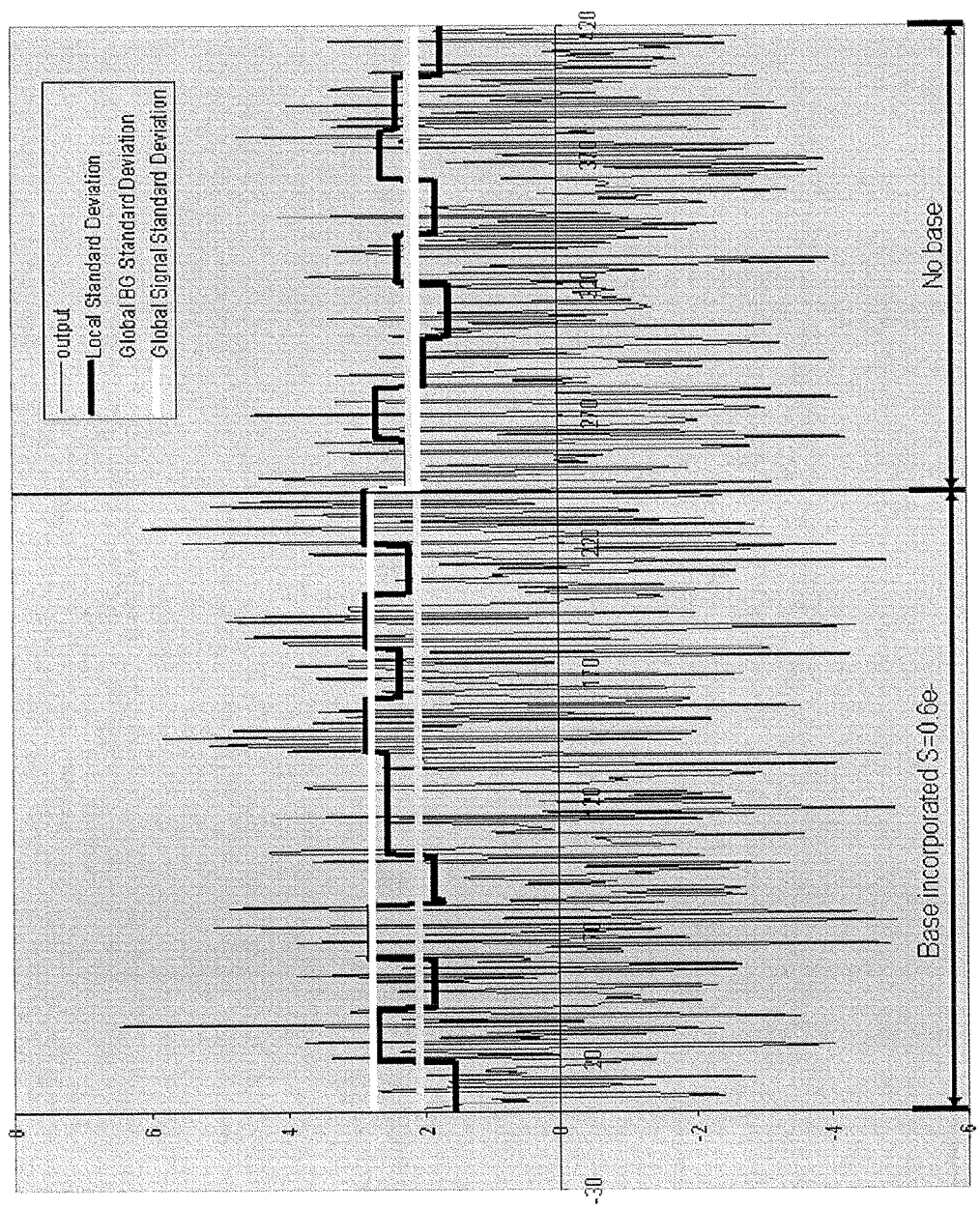

In an exemplary process, a given application that includes multiple different labeled species, e.g., different labeled nucleotides, includes labels that differ in their excitation spectra. Illuminating a reaction mixture iteratively with the different wavelength excitation sources provides temporal separation between excitation of the different labels. By correlating an emitted signal with one of the different excitation wavelengths, one can interpret the signal as emanating from a given label. In operation, one can cycle through the various different excitation sources at high frequencies, and detect the correlated emissions at equivalently high frequencies. This is illustrated in FIGS. 30A, 30B, and 30C. As shown in FIG. 30A, different excitation sources are pulsed in an interleaved fashion. Exemplary timescales of such pulses are illustrated in FIG. 30B, along with the corresponding expected residence times of detectable species, and the expected signals that would emanate from those species. Also shown is the pixel integration over a given frame that includes multiple cycles through the various excitation pulses.

FIG. 30C shows simulated integration and detection of a signal from a labeled reactant (left half of plot), and the absence of a labeled reactant (right half of plot), even in the presence of high noise levels (pulse extraction with a signal of 0.5 electron/sample and 6 samples per frame and a 1 electron background).

In accordance with the invention, an integrated smart pixel can be employed in efficient detection and distinction of the various signal elements that would derive from the foregoing. A schematic of the pixel design is provided in FIG. 31. As shown, the pixel including a photodiode 1102 includes four integrated storage elements 1104, each of which may be electronically gated by the activation of a separate excitation source. In such cases, a modulated controller element would be coupled to both the detector and the excitation illumination sources to synchronize the illumination and storage events. As a result, each storage element will be correlated to a given excitation event and consequent emission event, such that detected signals for each different type of excitation event are relegated to a different storage element.

In addition to being correlated to discrete excitation events, additional correlations may be pre-programmed into such systems. For example, any delay between an excitation event and an emission profile, e.g., for a given type of labeling group, may be preprogrammed into the pixel so as to take such delays into account in the detection event. Likewise, all storage elements could be switched off during intermediate stages of the excitation process, to avoid any noise contributions, slower decay rates of some signals, etc. As shown, and as will be appreciated, conventional logic elements, amplifiers, etc. are also included.

Figure 31:
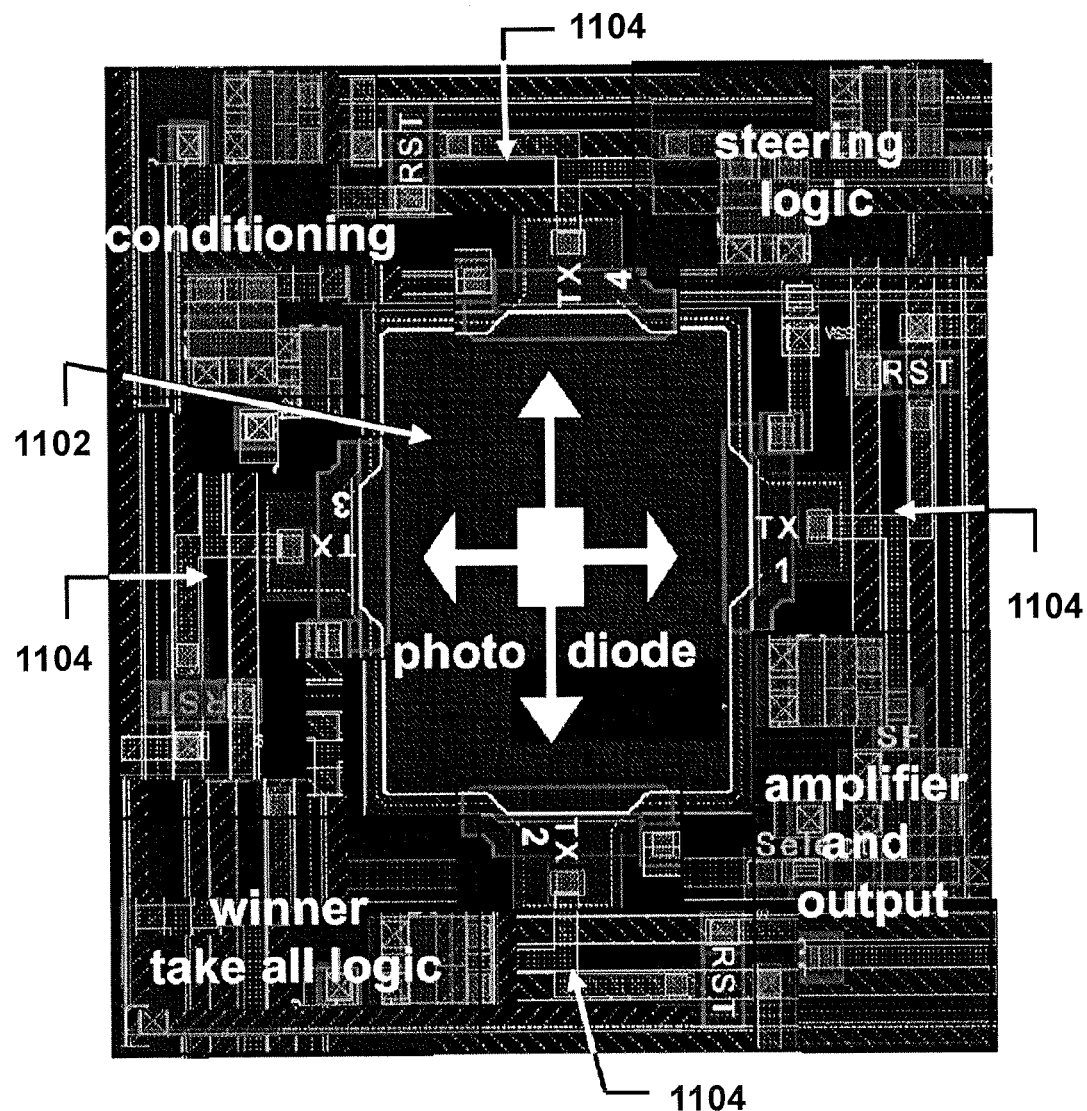
FIG. 31 is a schematic view of a pixel design in accordance with the invention.

The exemplary pixel detector of FIG. 31 contains steering logic and multiple integrating nodes. The nodes can be run simultaneously or switched during optical integration periods. The photodiode 1102 is connected to a plurality of integrating and processing nodes 1104. These nodes are generally connected to the photodetector via transfer gates (TXn). In depletion mode, these channels are non-conducting (i.e. open) when a low voltage is applied to the gates. When a high voltage (e.g. several kT above the transistor threshold voltage) is applied, however, a conducting path is made between the nodes and the photodetector. In various embodiments, each integrating node is independently reset to clear the previous charge from its circuits prior to transfer operations. Although the exemplary photodetector uses CMOS, NMOS or PMOS technology, any MISFET, BJT or other switching circuit elements can be substituted without altering the basic disclosed operation.

The use of multiple integrating nodes on a common photodetector can be used to separate photocharge events of many causes. In various embodiments, the detector is configured as a vertical detector whereby the depth of absorption of photons in the detector is related to its energy level. Having multiple collection nodes at different depths in the detector provides a method to determine the color of the incident illumination by comparing the relative strengths and absorption depth of the signals. In this case, generally all the transfer gates are active simultaneously and the optical integration time can be controlled by the transfer gate active duration time. Based on the previous events, each integration time can be different to essentially equalize or extend the operating dynamic range.

In various embodiments, the arrival time or resonant phase of a photon to a regular or synchronized event can be used to classify the species of the signal. If each signal is responsive to different input stimulus, the stimulus can be applied in a regular and sequential fashion. By synchronizing the stimulus with an unique integrating node, the species can be determined. If a lag in response to a frequency modulation of the stimulus (chirped, swept, constant) exists, this phase margin can be detected by appropriately delaying the transfer gate to each integrating node with the in-phase signal from the stimulus. In each of these cases, the relative response from each integrating node can be used to positively identify and classify the species.

One will appreciate that this architecture can also be used to determine high speed events (sub-frame rate) by storing multiple sub-frame samples that could have temporal overlap. In various embodiments, the detector includes local storage within pixels to achieve high speed burst collection.

VII. Overall Analytical System Architecture

A large number of optical analyses, including those described herein, utilize a common overall analysis system architecture. In various embodiments, the present invention is directed to a scalable system architecture utilizing a plurality of analytical assemblies (optodes). The exemplary system further includes a sample delivery assembly and a processing system.

In various embodiments, the analytical device is an integrated, portable device configured for local data stream processing. In one example, a single-use analytical system includes 60,000 individual analytical device elements grouped in an area less than about 1 mm². Sample can be prepared off the device and introduced into the device via microfluidics channels, e.g., fluid delivery system 33 In various embodiments, the analytical array includes local, integrated components including, but not limited to at least one of a fluidics system, a power source, an illumination system, a detector, a processing circuit, a controller, steering logic, and electrical connections. The exemplary device includes a portable, on-chip, battery-powered light source (i.e. LED or laser) and a single FPGA can process the data stream (e.g. 65,000 samples at an average of 25 bases per second). The detection methods described herein can be adjusted to maintain a bandwidth where a single LVDS channel would interface to the FPGA and a standard PC interface can be provided from the FPGA output to the external analysis equipment.

Although the analytical devices of the present invention typically include multiple elements for an analytical system integrated into a single device architecture, it will be appreciated that in many cases, the integrated analytical devices may still employ a companion instrument system to provide additional functionality for the analysis of interest. In particular, as noted previously, in some cases the illumination of optical analyses will utilize an illumination source that is separate from the integrated device structure. For example, lasers, LEDs or other conventionally employed illumination sources may be provided within a larger instrument that is mated with the integrated device. Likewise, power supplies for the integrated device, where needed, may also be provided within an instrument architecture. In addition, any environmental controls, fluidics, fluidic control components (whether electrokinetic, pressure based, or control of integrated pumping and valving mechanisms, or other) may be provided within the instrument architecture. As will be appreciated from the description herein, any number of these components may be integrated into the system or connected remotely. For example, the illumination components can be integrated into the system with a system platform and connected to the analytical device array with a test socket as described above. In another example, the illumination components are provided in a separate illumination instrument and connected to the system in conventional manner.

Where such other functionalities are provided within an instrument architecture, such an architecture may include one or more interfaces for delivering the particular functionality to the integrated device. For example, optical interfaces may include fiber optic connections, optical trains or other optical interfaces to provide illumination to complementary connections on the integrated device, which then communicate that illumination to the reaction cells or otherwise, as necessary.

Electrical and data connections may also provide the requisite power and data communication between the sensor components of the device and a processor that may be integrated into the instrument architecture, or that may be exported or communicated to an associated computer that is external to the instrument itself.

Fluidic interfaces are also optionally provided within the system architecture for easy delivery of reaction components to the reaction cells. In various embodiments, the fluidic interface comprises fluid connectors that permit the sealed connection of fluid reservoirs in an instrument with complementary connections on the analytical device, including, for example, fluidic manifolds with controllable valving and pumping mechanisms. In various embodiments, the fluid connectors are provided on a test socket into which the analytical device array is seated.

Other interfaces include, for example, control interfaces with the device for controlling movement of fluids around an integrated device. Such interfaces may include electrical interfaces, e.g., to drive electrokinetic transport or to power integrated pumping and valving mechanisms, or pneumatic or hydraulic interfaces, to perform similar controls.

One of skill will appreciate from the description herein that the system and method of the present invention generally increases flexibility, promotes scalability, and reduces costs. The system architecture of the invention enables many concurrent sequencing applications. By developing systems with common design elements, great economy of scale may be achieved and result in overall reductions in part costs, field service and development time and resources. Bundling parts across these applications may provide enhanced buying power and better ability to manage yield and overall quality.

One will appreciate from the description herein that any of the elements described above can be modified and/or used with any of the other elements, in any combination, in the system in accordance with the present invention.

VIII. Other Excitation Techniques

Various aspects of the invention are directed to a system whereby the reactants in the waveguides are excited by means other than direct impingement with a laser and the like. Turning to FIGS. 32-41, a system including devices for illumination with surface plasmons will now be described. There is increasing interest in the use of plasmons to excite fluorophores and other materials at least because the use of plasmons may have advantages in imaging small volumes like zero mode waveguides.

Conventional techniques for creating plasmons and using plasmons on a small scale (e.g. to excite fluorophores) are described in Radiative Decay Engineering Surface Plasmon Coupled Directional Emission, Analytical Biochemistry 324 (2004), pages 153-169; Unidirectional Ultracompact Optical Nanoantennas, Nano Letters, 2009 Vol 9 #6 2343-2349; Focusing Surface Plasmons with a Plasmonic Lens, Nano Letters 2005 Vol 5 #9 1726-1729; Plasmonic Lens Made from Multiple Concentric Metallic Rings under Radially Polarized Illumination, Nano Letters 2009 Vol 9 #12 4320-4325; and Squeezing Visible Light Waves Into A 3 Nm Thick And 55 Nm Long Plasmon Cavity, Physics Rev. Letters 2006 #96 097401-1.

Plasmons are quanta of vibrational energy formed when radiation is incident on a metal surface. The term "surface plasmon polariton" (SPP) is used to describe optically-induced electron oscillations. Waveguides can be fabricated to utilize resonant plasmonic energy with relatively long coherence to transmit optical energy or information over a distance. See Nanohole Chains for Directional and Localized Plasmon Excitation, Nano Letters 2010, 10 285-290; A Plasmonic Dimple Lens for Nanoscale Focusing of Light, Nano Letters 2009 V9 NIO 3447-3452. Alternatively, plasmonic antennas can be used to enhance the detection and emission of plasmons at wavelengths below the photonic stimulation radiation wavelength to enhance operation of zero mode waveguides in very small volume interrogation. See Unidirectional Ultracompact Optical Nanoantennas, Nano Letters 2009 9 6 2343-2349; Manipulating Nanoscale Light Yields with the Asymmetric Bowtie Nano-colorsorter, Nano Letters 2009 9 12 4505-4509. Direct coupling of light waves into sub-wavelength apertures can create SPPs with high efficiency (e.g. up to 28%). See Coupling Efficiency Of Light To Surface Plasmon Polariton For Single Subwavelength Holes In A Gold Film, Optics Express 2008, 16, 5, 3420.

The exemplary analytical devices and zero mode waveguides making use of SPP techniques yield several advantages. By directing optical energy to an area proximal to the zero mode waveguide where a plasmonic generator is located, excitation of fluorophores located near the source may be enhanced. The Plasmonic resonators of the invention may also be used to localize energy to a smaller volume than that performed by the evanescent decay of photonic electromagnetic (EM) waves. By shielding the optical signal path from incident photonic energy, one may eliminate the need for optical source filtering and the broader band auto-fluorescent background signal that is generally associated as a byproduct of the source brightness. Because the strength of plasmons decreases significantly in proportion to distance, SPP techniques may also reduce background noise in comparison to photonic illumination techniques.

Figure 32:
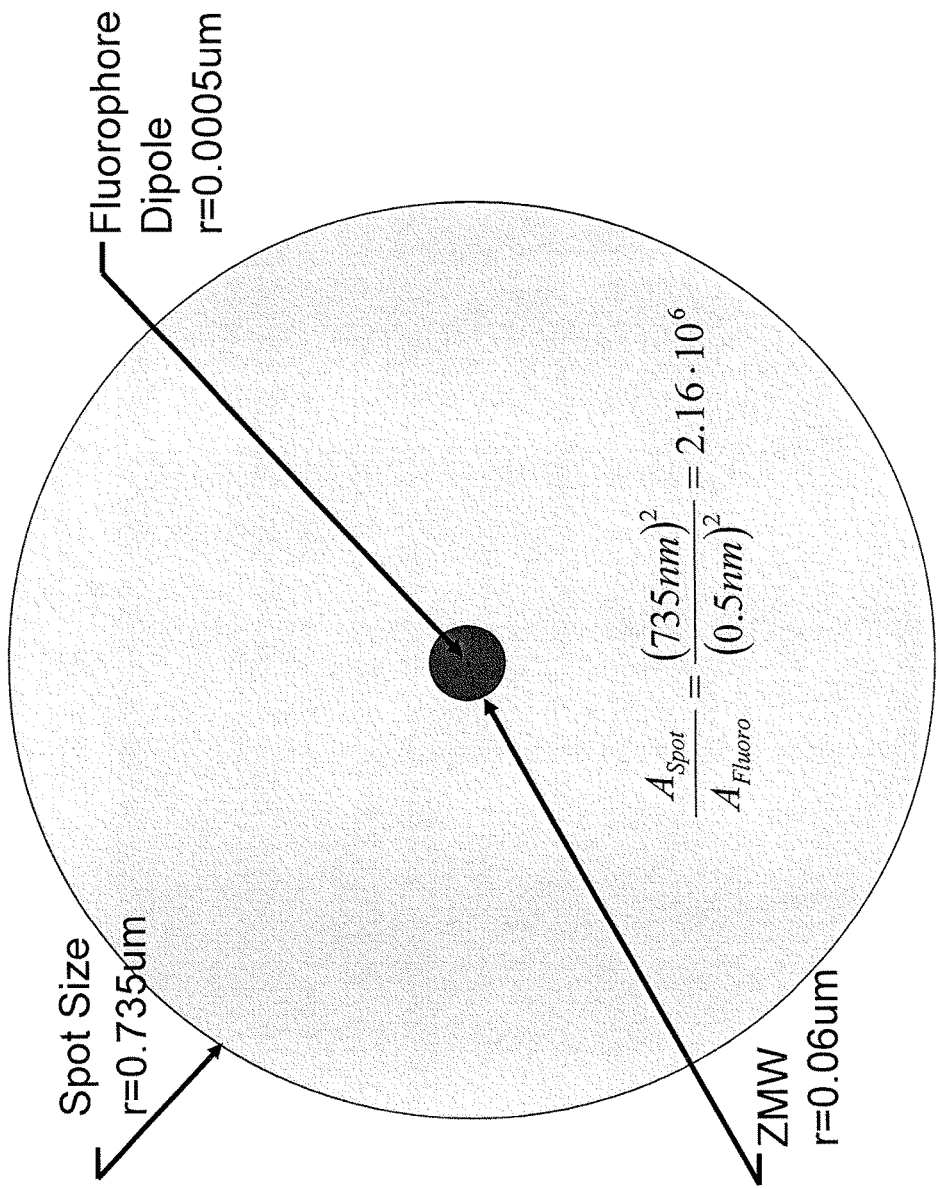
FIG. 32 is a schematic illustration of one embodiment for exciting a fluorophore.

One approach to exciting the fluorophore is shown in FIG. 32. A spot of light is directed towards the ZMW and limited by diffraction limits at the incident light wavelength.

$$d = \frac{\lambda}{2n \cdot \sin(\alpha)}$$

This approach may have drawbacks, however. The diameter of the exemplary ZMW is much smaller than the diameter of the first minimum of the Airy disk from the spot illuminant. In addition, the absorption of photonic energy by a fluorophore dye is limited to a cross-section approximately equivalent to the dipole length (approximately 1 mm). Therefore, the area ratio between the incident spot size and the fluorophore dipole is over 2 million to one. Additionally, evanescent decay of the incident light into the ZMW further reduces energy transfer efficiency.

To overcome the efficiency loss, very high illumination levels are used to excite the fluorophore. This may require significant filtering of the reflected incident light from the camera, and the high intensity causes significant auto-fluorescence in the optical components must be further reduced.

An alternative approach is to confine the optical energy to a smaller spot located at the dipole of the illuminant. As demonstrated in the equation below, an incident photon wave can be approximated from the Maxwell's equations by considering only the high frequency response (assuming the magnetic response induced currents are not appreciable).

$$-\nabla^2 E = \frac{n^2 \omega^2}{c^2} E$$

where the field is represented by a set of plane waves (x,y,z).

$$k_i = \frac{2\pi n}{\lambda_o}$$

shows that the vector is constrained by the index of refraction in the optical materials and limits the traditional spot size to approximately (1.22*λ)/NA.

Surface plasmons may provide a method to achieve higher effective indices to create modes at optical frequencies with indexes that are orders of magnitude higher than for optical materials. The plasmon frequency is determined by the relative dispersion of the wave vector at the metal-dielectric interface. Metals have a large dispersion compared to the relatively constant permittivity in the dielectric. Using the Drude model:

$$\varepsilon_m = 1 - \frac{\omega_p^2}{\omega^2}$$

where $\omega_p$ is the plasma frequency.

Thus, it is shown that the increase in dispersion happens at higher wave vectors than from the optical field alone. Free space optical fields generally cannot generate plasmons without added momentum.

Surface plasmon modes generally tend to be quite lossy and most of the loss is in the absorption in the metal. Plasmon decay lengths are typically less than 10 micrometers but can be enhanced by directing the majority of the energy into the dielectric layer of a device (e.g. a metal-insulator-metal device with 100s of micrometer). The Quality Factor of an exemplary metal-insulator-metal (MIM) device is generally proportional to the metal used and the input frequency (generally about 2 eV-about 3 eV).

Figure 33:
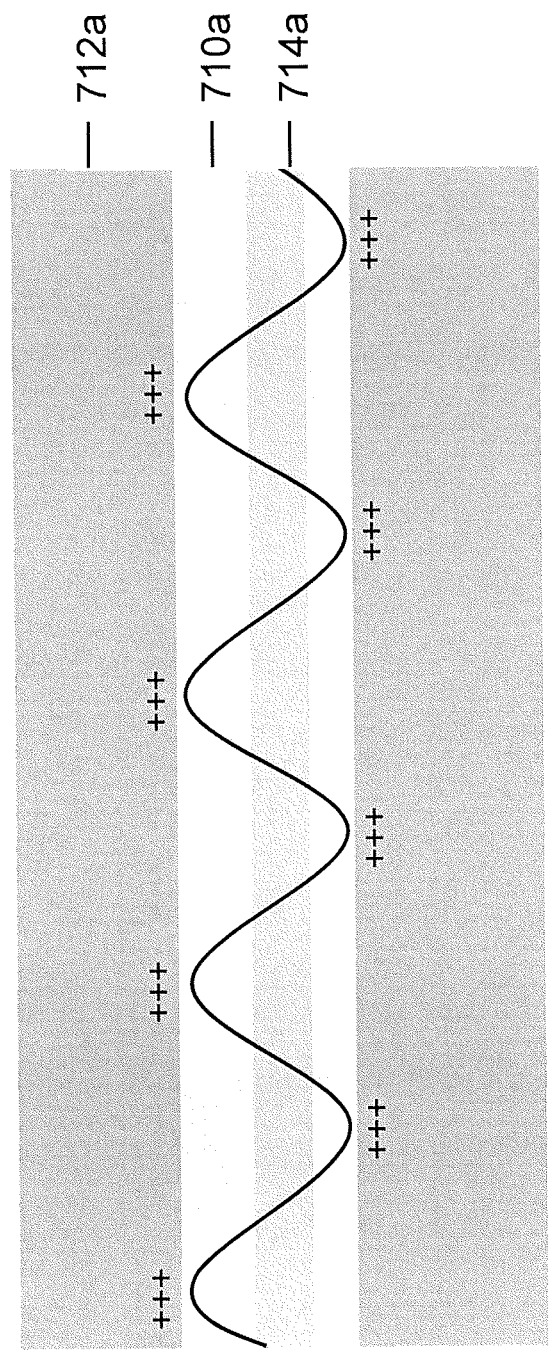
FIG. 33 is a schematic view of a MJM structure in accordance with the invention.
Figure 38:
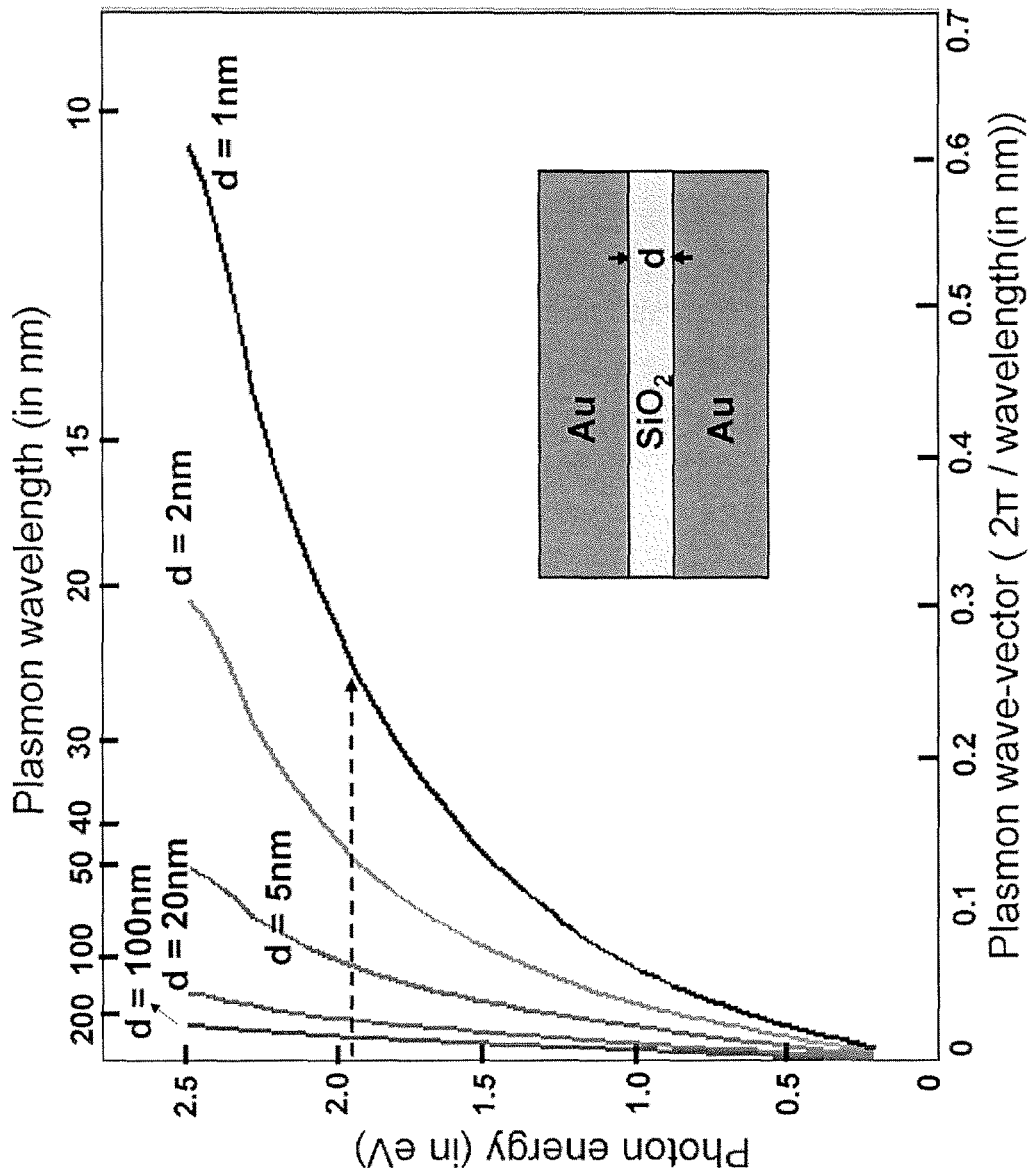
FIG. 38 is a plot diagram of surface plasmon wavelengths based on incident photon energy for varying insulator thicknesses.

A simplified MIM structure is shown in FIG. 33. The exemplary MIM structure is developed with plasmonic confinement at optical frequencies using standard commercial foundry design rules. For example, the design rule for gate oxide thickness at the 65 nm design node is about 1.1 micrometer. Oxide thicknesses greater than this can be used to tune the system to the plasmon wavelength required (as shown in FIG. 38). A tradeoff in propagation length and plasmon energy is made with the dielectric thickness, but with the small dimensions of the ZMW, even 1-micrometer-thick-slabs producing less than about 10 nm wavelengths have propagation constants in excess of about 400 nm.

Light with a sufficient and correct incident angle and polarization is generally required to generate efficient SPPs and limit skin depth absorption. With an angle of less than 30% for aluminum, for example, greater than about 40% coupling efficiency may be possible. Thus, this form of directed energy can form a focus to the scale of the dipole with quanta energy equivalent to the incident photons and with much higher efficiency than the 2,000,000:1 efficiency through direct spot beam illumination.

By carefully tuning the plasmonic structures to the zero mode waveguide dimensions and the incident illumination, the energy transfer efficiency may also be optimized. One will appreciate that the wavelength of the SPP can be tuned based on the waveguide dimensions and the incident optical illumination wavelength. This decouples the ZMW dimensions from the optical excitation wavelength to allow for greater design flexibility. One will further appreciate, therefore, that the ZMW can be tuned to maximize performance to the chemical kinetics and emitted light profile requirements. Conventional photonic illumination techniques require sizing the ZMW based on the photonic wavelength. For example, a ZMW with a diameter much less than 100 nano-inches could be used to increase SPP absorption by the fluorophore as well as increase the density of and array of ZMW elements.

In various embodiments, the method in accordance with the present invention includes illuminating the fluorophore in a ZMW well with plasmons. In various embodiments, the plasmons are generated within a propagation length (e.g. about 500 nm) from a photonic source that is shielded from the detector optical path. The device of the invention also inherently insulates the excitation with SPPs from the incident photonic signal in the waveguide thus reducing noise.

Figure 34:
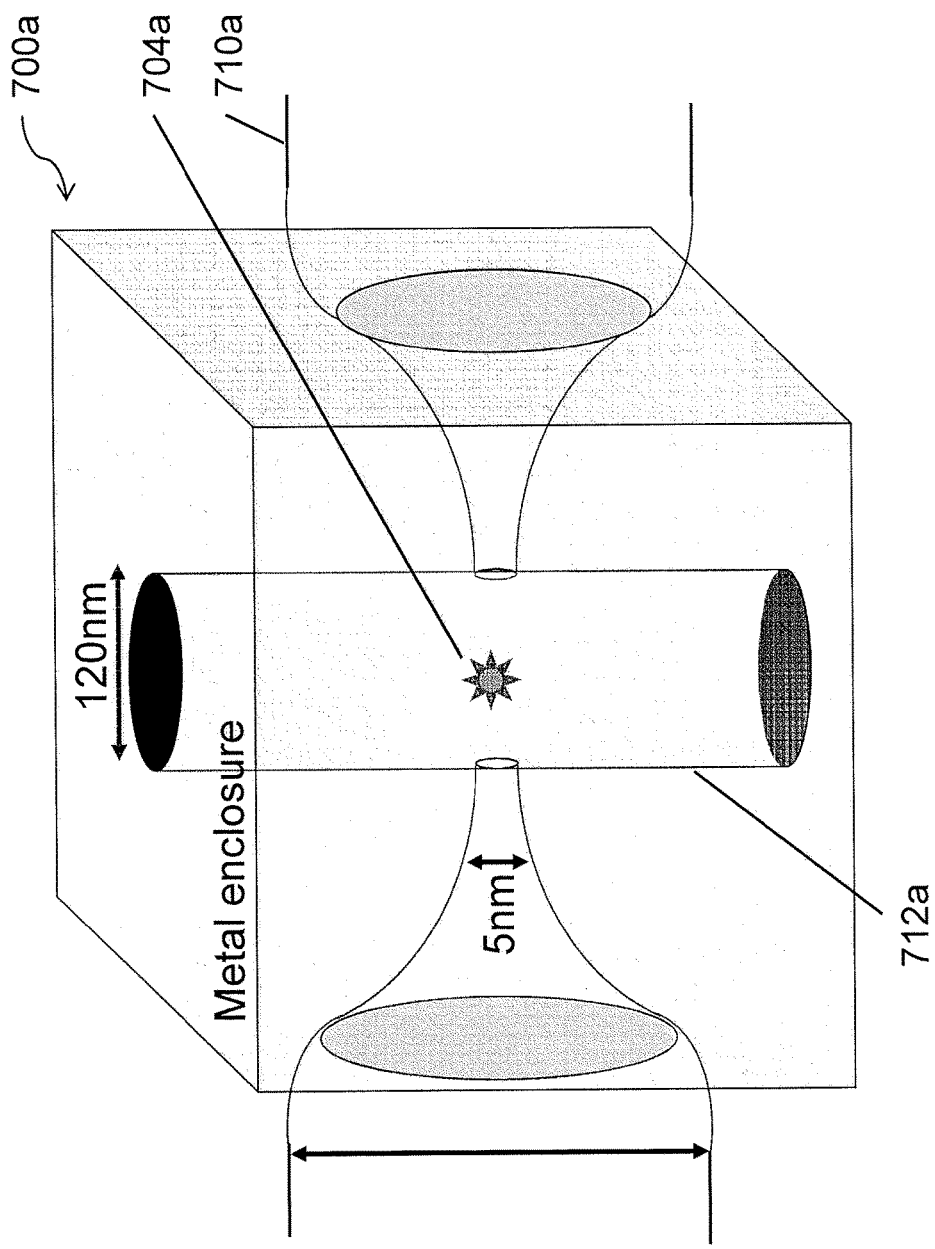
FIG. 34 is a schematic view of a waveguide assembly in accordance with the invention for exciting a material with SPPs.

FIG. 34 shows an exemplary system for illuminating a reactant in a reaction cell using SPPs. The exemplary system, generally designated 700a, includes a planar waveguide 710a for receiving light from a light source and one or more apertures within the planar waveguide. The exemplary waveguide is configured as a funnel with a narrow conduit portion having a diameter of about 5 nm. The planar waveguide is disposed within a metal enclosure for generating SPPs in response to optical energy from the waveguide.

The apertures are formed to define reaction cells 702a for housing a set of reactants. In an exemplary embodiment, the reactants include one or more reactants labeled with a fluorophore 704a. In general, the plasmonic energy may be absorbed by a fluorophore, quantum dot, or any other tag material to signal the presence of a reagent molecule. This signaling material may emit an energy that is distinct from the incident plasmonic field.

Turning to FIGS. 35-41, an exemplary device 700 with a layered structure and a plurality of reaction cells is shown. The exemplary device includes a metal layer 712 configured to generate SPPs based on plasmon modes in response to optical energy. A dielectric slab 714 extends between top and bottom portions of the metal layer. Waveguide 710 is disposed between the metal layer and dielectric slab. The waveguide is configured to receive optical energy and transmit the optical energy to the metal layer similar to the waveguides discussed above. The device further includes reaction cell 702 disposed between adjacent ends of the dielectric slab 714 and metal layer 712.

The exemplary device is generally separated into various regions configured for adjusting the introduced light, generating SPPs in response to the light, and applying the SPPs to the reaction cell. Moving from the center of the device outward, the device includes a first region having reaction cell 702 configured to receive a fluorophore and/or other reactants. A second region laterally adjacent the first region includes a metal-insulator-metal (MIM) structure for providing plasmonic energy to the reaction cell. The MIM structure is formed of slab 714 sandwiched between metal layer 712. Waveguide 710 includes a thin conduit portion 710a extending between a portion of a top surface of slab 714 and a bottom surface of metal 712. A third region includes a MIM structure and a waveguide transition portion 710b. The waveguide transition portion is dimensioned and configured for funneling optical light to the MIM structure. A fourth region extends along an outer portion of the device and includes an optical waveguide inlet 711 for receiving and introducing optical energy into the waveguide. The exemplary inlet is positioned along a side edge of the device.

Figure 40:
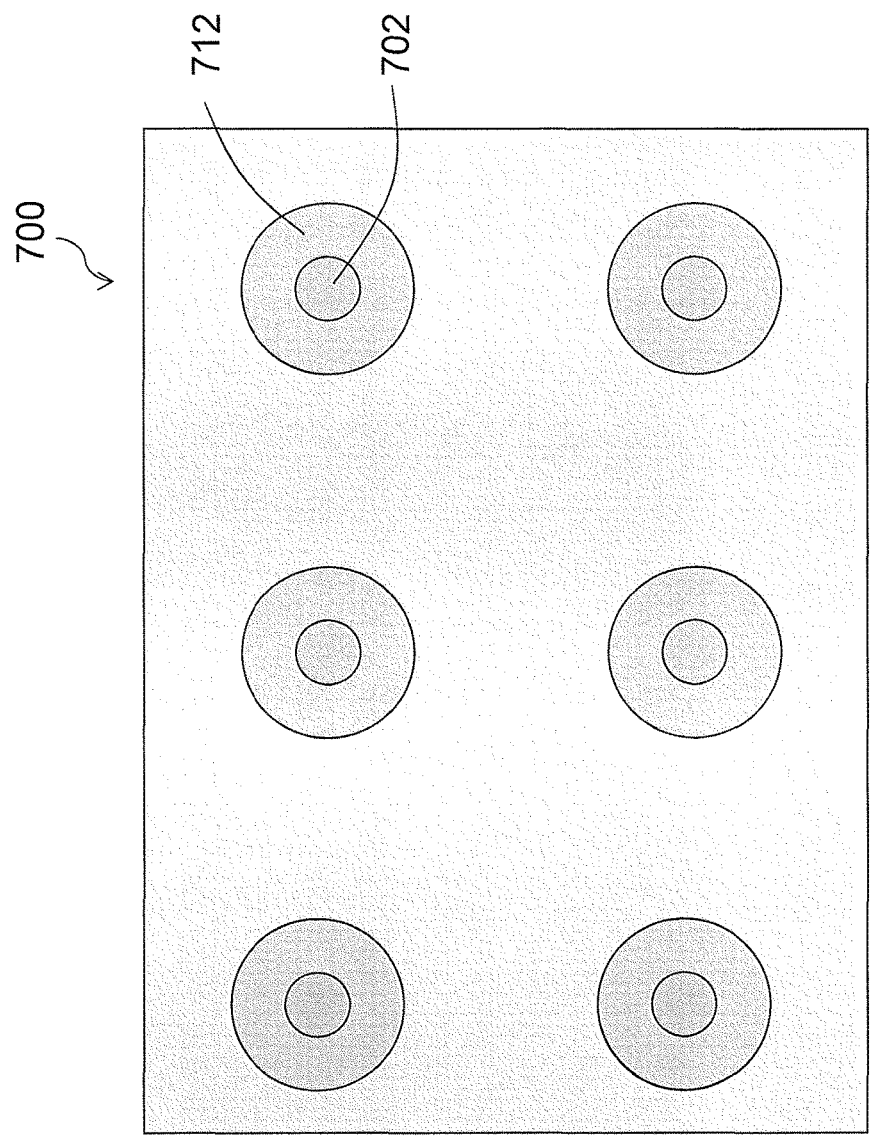

In the exemplary device, the waveguide is a planar waveguide, and in particular a tapered lateral illumination conduit aligned with the reaction cell. The illumination conduit comprises a circular taper forming a disk of plasmonic energy. As shown in FIG. 40, in various embodiments the system includes MIM layers with a plurality of apertures extending therethrough to define reaction cells. In various embodiments, the MIM structure and waveguide are essentially concentric rings and the reaction cell is positioned in a center of the ring. The waveguide extends around at least a portion of a circumference of the reaction cell. Although the exemplary waveguide extends entirely around the reaction cell, one will appreciate that that the waveguide can extend around only a portion of the reaction cell. For example, the waveguide structure may be configured as an antenna or projection with the reaction cell positioned at one end.

Figure 35:
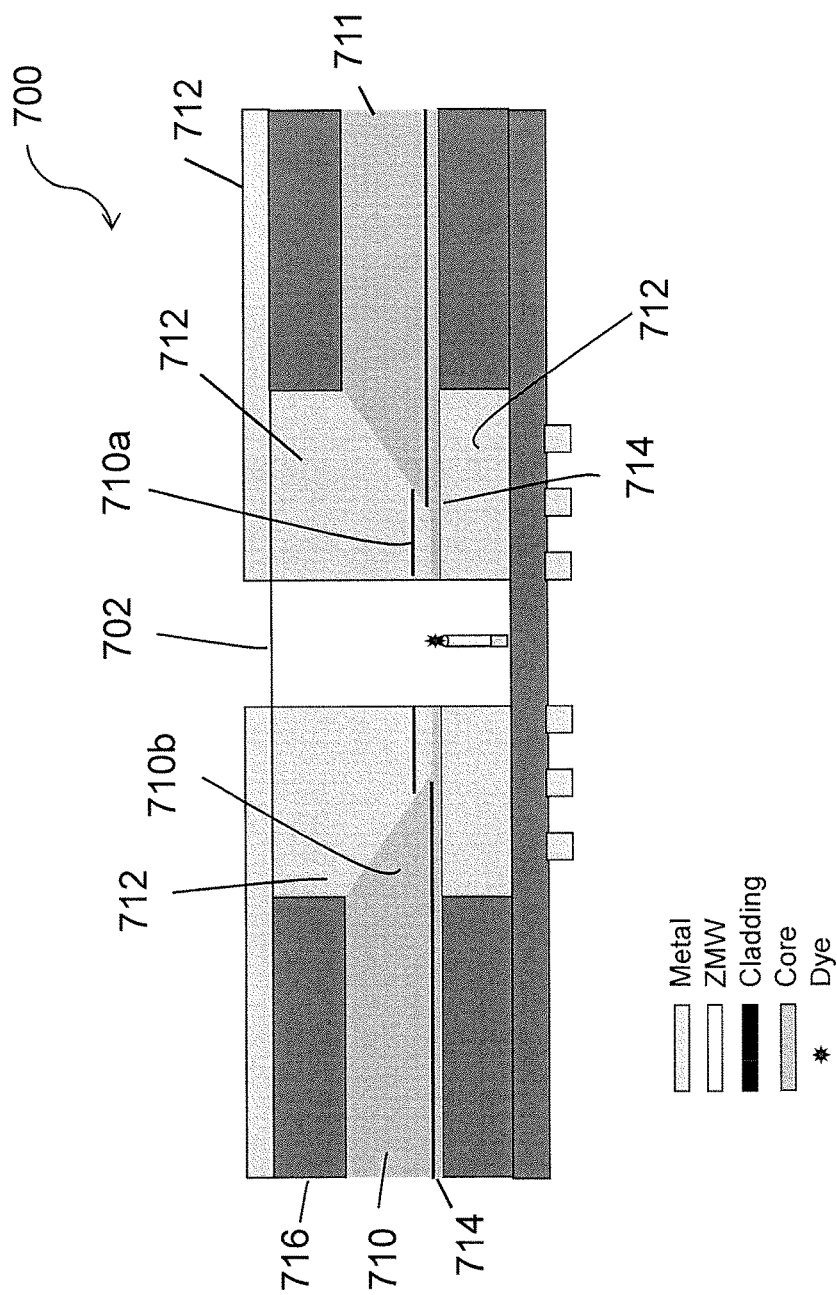
FIG. 35-FIG. 37 are several views of analytical devices configured for excitation with surface plasmon polaritons.
Figure 36:
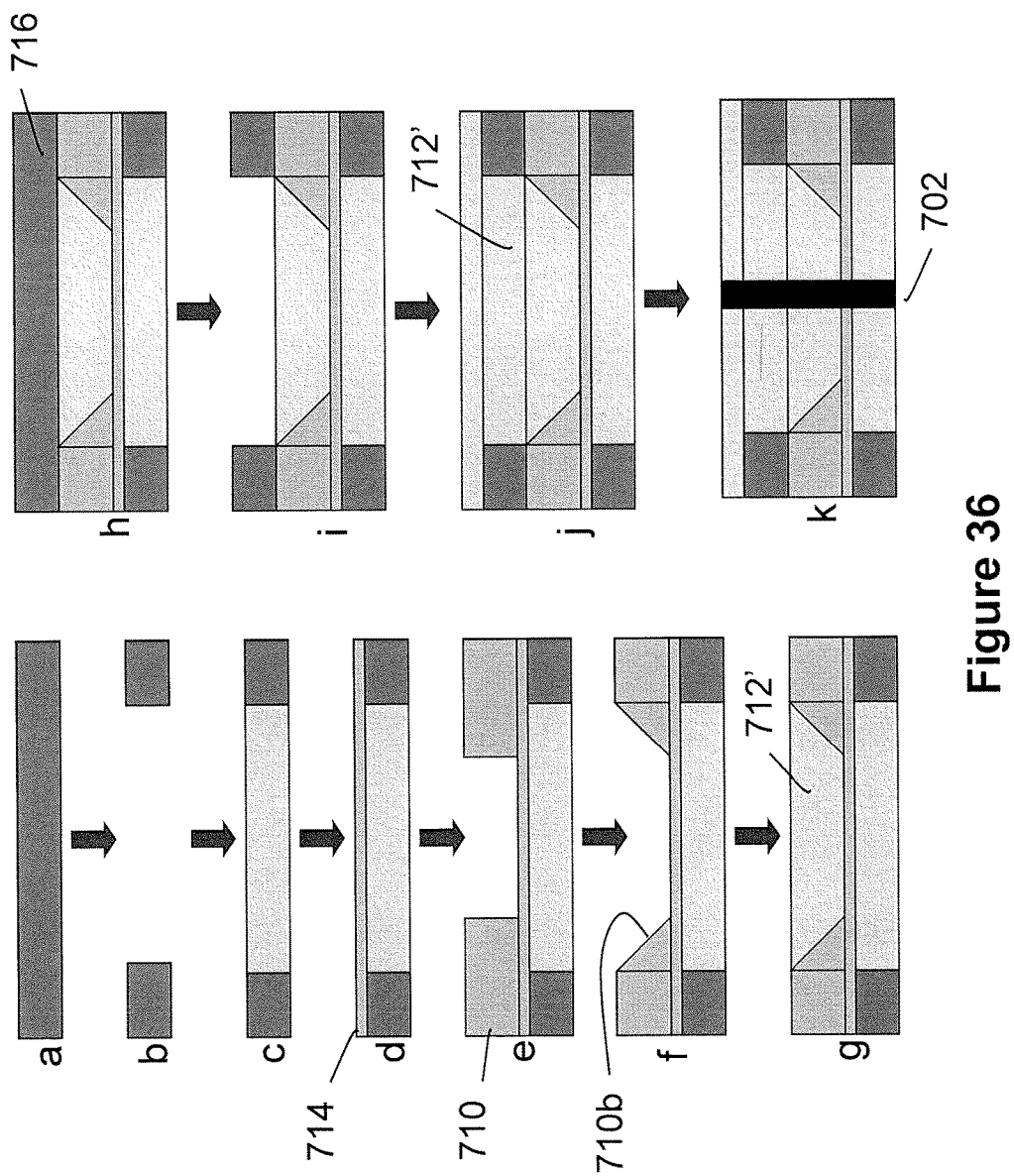
Figure 37:
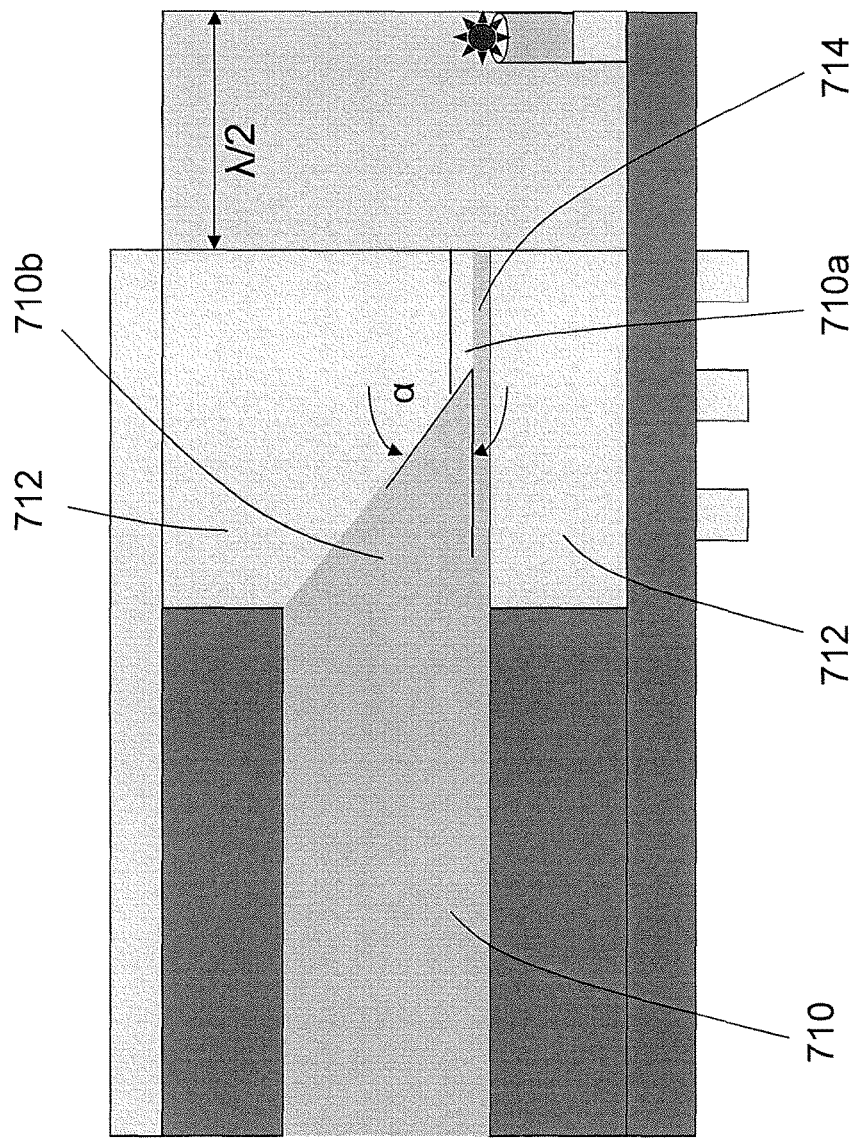
Figure 39:
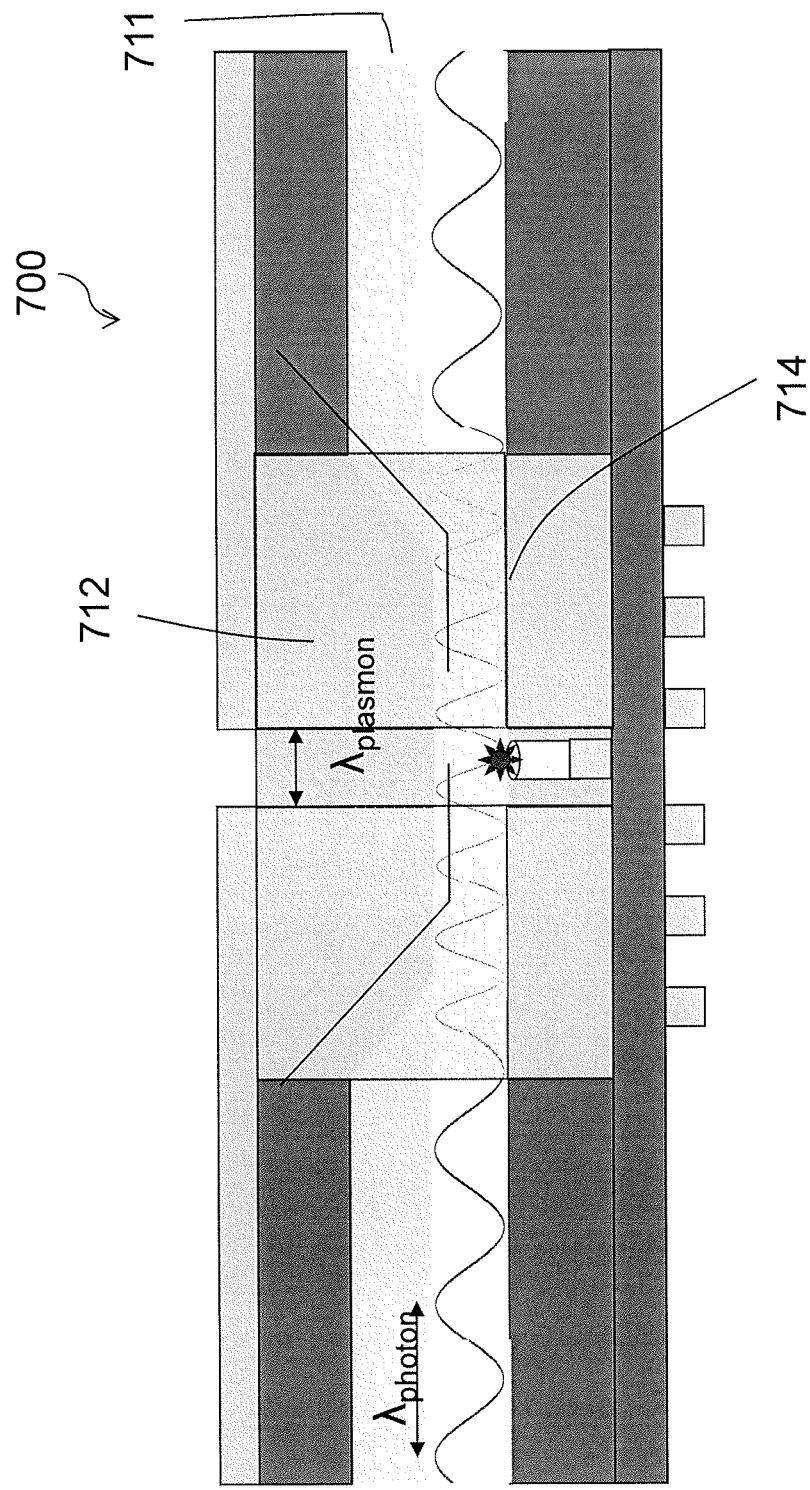
FIG. 39-FIG. 41 are several views analytical devices configured for excitation with surface plasmon polaritons.

Referring to FIGS. 35, 37, and 39, exemplary transition portion 710b is tapered with a decreasing thickness. The transition includes a smooth and linear shape to funnel the optical energy into the conduit 710a and MIM with minimal losses. A dimension and shape of the taper may be selected to achieve a desired resulting plasmonic wavelength in the metal layer based on a wavelength of the introduced optical energy as will be appreciated by one of skill in the art from the description herein. The exemplary transition portion is dimensioned and configured to decrease dispersion of the photonic wave vector at the metal-dielectric interface. In an exemplary embodiment, the waveguide taper 710b is fabricated with a single angled surface to be more compatible with standard semiconductor processes as shown in FIG. 36.

The exemplary dielectric slab 714 is an electrical insulator configured for plasmonic confinement of the waveguide 710. The dielectric slab may extend along all or only a portion of the waveguide. The device optionally includes a cladding layer 716 in the fourth region for isolating the waveguide from the metal layer and confining optical energy in the waveguide. The cladding layer extends along the waveguide inlet toward to the transition portion. A top portion of the waveguide transition portion is open to the metal layer such that as the optical energy moves into the transition portion some of the energy is transferred to the metal layer to cause the metal to resonate and generate SPPs.

One will appreciate from the description herein that the interface between the waveguide and metal layer may be modified depending on the application and desired result. The waveguide may be physically separated from the metal layer with shielding and the like. As shown in FIG. 33, for example, the optical wave may be confined within a portion of the MIM structure by a high refractive index boundary. One will appreciate that other structures and configurations may be used to confine and direct the optical energy and plasmons in the device.

Figure 41:
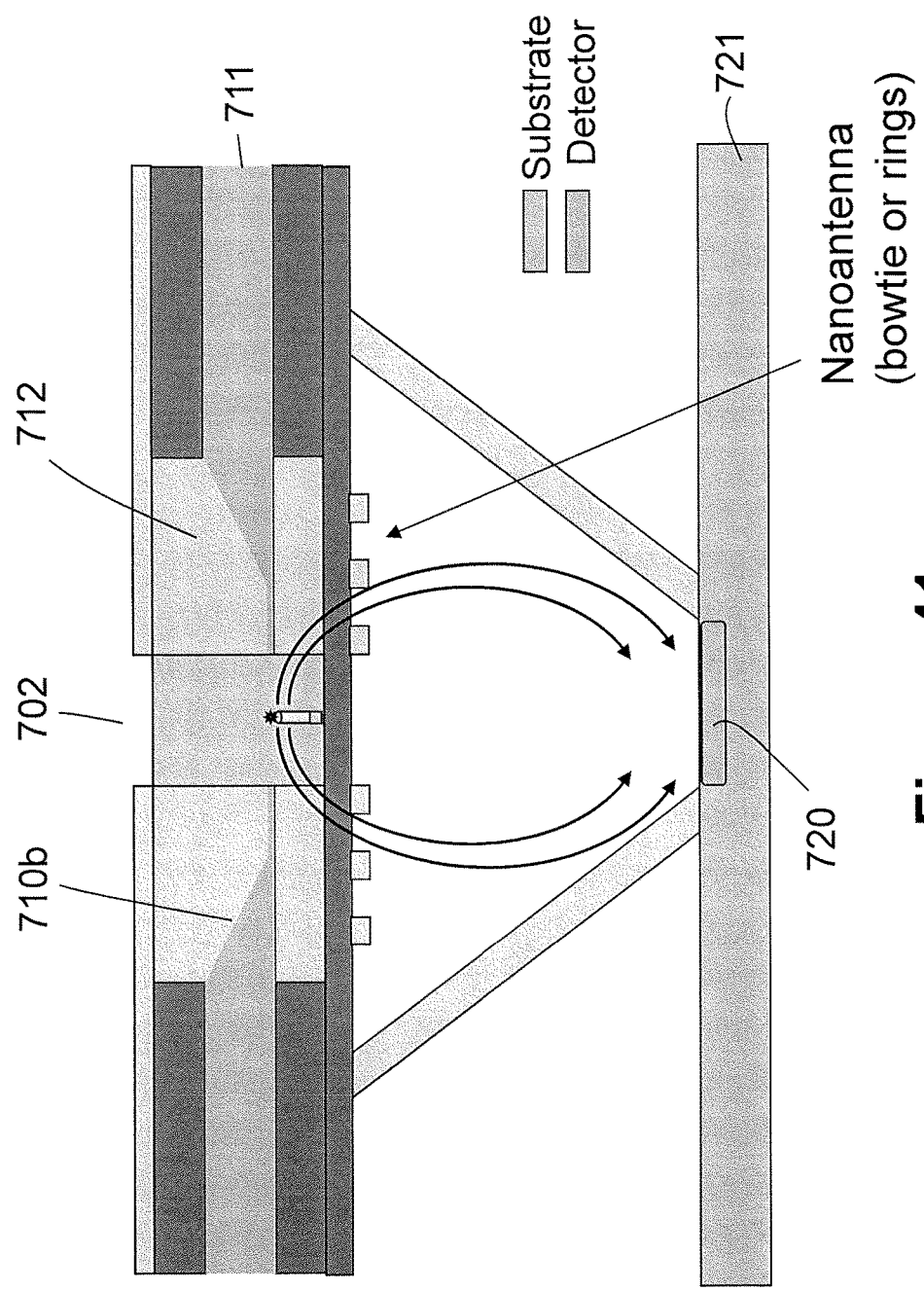

Referring to FIGS. 39, 40, and 41, the device includes a sensor element 720 disposed in a substrate 721 below slab 714 and metal layer 712. The sensor element is in optical communication with the reaction cell along a detection pathway as shown in FIG. 41. In the illustrated embodiment, the sensor element is positioned essentially below the reaction cell and an optical tunnel is provided to focus an emitted signal from the reaction cell to the sensor element.

As noted above, the use of SPPs for excitation allows for shielding the reaction cell and detection pathway from optical energy. In various embodiments, the device includes an optically opaque top layer for shielding the reaction cell and the detection pathway.

In various embodiments, the introduced optical energy is light having a wavelength of about 0.5 micrometer. In various embodiments, the light has a wavelength of about 650 nm, and preferably about 647 nm. In an exemplary embodiment, reaction cell 702 has a diameter of less than or equal to about 0.6 micrometer. In various embodiments, the reaction cell has a diameter of less than 200 nm, and preferably about 180 nm, and more preferably about 50 nm. In an exemplary embodiment, waveguide 710 has a thickness of about 1 micrometer in a region adjacent the reaction cell. In an exemplary embodiment, dielectric slab 714 has a thickness of about 10 nm to about 20 nm. In an exemplary embodiment, the second and third region comprising the MIM structure and transition portion has a length of about 1 micrometer.

In operation, the optical signal is introduced into waveguide 710 through inlet 711. The optical signal is funneled between the cladding layer and dielectric slab at the waveguide inlet. The optical signal travels through the waveguide towards the MIM structure. The optical signal may be directed by total internal reflection, refractive devices, and the like. At an opposite end, in the third region, the waveguide interfaces with the metal layer along the transition portion. The optical signal undergoes a change as it moves into the transition portion. Some of the optical signal will be lost to the metal layer where it will disperse. Although some energy will not be transferred to the MIM structure, the loss is insignificant because of the greatly increased energy transfer efficiency of the SPP device as described above. In an exemplary embodiment, about 70% of the optical signal strength will be focused into the MIM structure by the transition portion. The optical signal travels into the MIM structure and causes SPPs to be generated. In turn, the SPPs are applied to the reaction cell in the first region. In general, the energy in the waveguide encounters the metal interface along the transition portion 710*b* and sonic of the energy propagates down the circular taper around the reaction cell 702.

In one example, light having a wavelength of about 647 nm is incident on taper 710*b* that is connected to dielectric slab 714 that is about 5 nm thick. The slab is sandwiched between two gold layers. A plasmonic field with a wavelength essentially equivalent to a 120 nm ZMW diameter is generated. The SPPs are then applied to the reaction cell in various fashion such as in bursts or essentially continuously. In various embodiments, the MIM structure is positioned in close proximity to the reaction cell so the SPPs are efficiently transferred to the cell. One will appreciate that the SPPs reduce the amount of background noise because the SPPs generally will not excite materials outside the reaction cell volume unlike a laser light that typically has accompanying background noise issues.

The exemplary device is configured for flood illumination from an edge of the device via inlet 711. The exemplary reaction cells are illuminated from various angles in the plane and inherent optical uniformity results. An optional plasmonic lens may also be fabricated at the bottom of the reaction cell to better focus the signal energy to an integrated detector.

One will appreciate from the description herein that the plasmonic resonator device allows for flexibility in tuning. By example, as the taper dimension is reduced, the plasmonic wavelength is reduced, the group velocity is proportionally reduced, and the skin depth is also minimized (linear with the thickness). The overall Quality Factor and efficiency can then be calculated and tuned for the input wavelength and the required plasmon frequency with a minimal insertion loss. The taper 710*b* may be thought of as an index waveguide with a continuously increasing diameter moving upwards. The exemplary device has an insertion loss in the reaction cell less than or equal to about 10 dB.

The chart in FIG. 38 illustrates the results when the thickness of the insulator in the MIM structure is adjusted. The results were obtained with a standard MIM structure such as that shown in FIG. 33. As shown in the chart, the plasmon wavelength and energy level may be tuned by adjusting the dimensions of the MIM structure. FIG. 38 shows the results of adjusting the dielectric thickness.

The plamonic excitation device has several advantages over light-based excitation devices. With reference to FIG. 39, for example, the reaction cell (ZMW) can be tuned to locate the fluorophore in line with the dielectric ring height. The use of plasmons for excitation also means that the diameter of the reaction cell can be tuned to the plasmon and chemical geometrical requirements. In contrast, conventional light-based ZMWs generally require tuning the ZMW based on the incident photonic requirements. The reduced wavelength of the plasmons may provide for the possibility of a reduction in the ZMW dimension. It is apparent that, with sufficient optical shielding, the incident light may be blocked from the reaction cell thus providing inherent gains in the detectivity and discrimination of the tag signal.

The exemplary device may be manufactured using standard semiconductor techniques. FIG. 36 is an exemplary process flow. The optical waveguide device 700 can be fabricated with two dielectrics. An area around the reaction cell 702 is etched away and a metal layer 712 is deposited in step c. A very thin oxide layer (plasmon dielectric slab 714) is deposited in step d. A balance of the metal layer is added in step e. The oxide is optionally anisotropically etched and the shape is used to pattern the metal plate taper in step g. An optional cladding layer 716 is added and the top metal layer 712' is added in step j.

In the exemplary structure, the reaction cell area and surroundings are generally formed of known materials with the exception of a very thin dielectric ring that is the waveguide. The reaction cell aperture is formed in step k. One will appreciate from the description herein that the above method may be modified and other fabrication techniques may be used. In various embodiments, the illumination fabrication is performed as part of the monolithic growth of the reaction cells described herein or as an intermediate layer in a hybrid assembly.

VIII. Scattering Illumination and Detection

Figure 42:
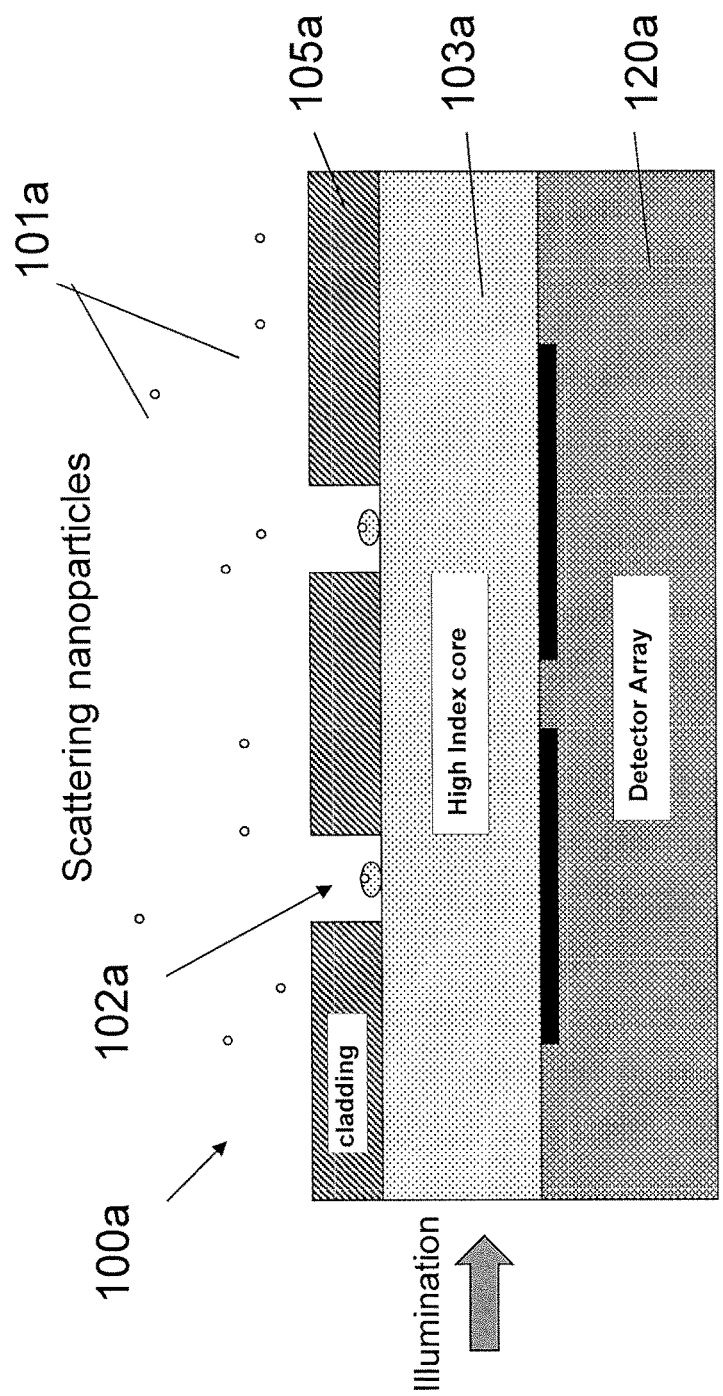
FIG. 42 is a schematic diagram of an analytical device with an array of reaction cells and waveguides configured for measuring scattering from nanoparticles.

Referring to FIG. 42, an integrated device 100*a* similar to the device of FIG. 1 is shown. The integrated device is configured for detection of scattering nanoparticles 101*a* while undergoing synthesis by DNA polymerase via the SMRT sequencing principle. The nanoparticles, such as gold or silver particles, are coupled to dNTPs to form phospholink analogs. The exemplary device is formed of a high index of refraction base substrate 103*a*, such as lithium niobate, into which illumination light is directed, in various respects to cause dark-field illumination or total internal reflection illumination of the top surface. The top surface has ZMWs 102*a* fabricated from a lower index of refraction material 105*a*, such as glass or alumina. The illumination creates the same observation volume confinement created in regular ZMWs, but the transparent nature of the top surface layer minimizes scattering of the incident light.

The backscattering of metallic nanoparticles is detected while they are processed by the enzyme. A different sized particle is conjugated to each of the four bases. In the exemplary device, differentiation of the bases is performed by the different scattering cross sections inherent in different particle sizes (corresponds with the sixth power of diameter), translating to different scattering "brightness" of the different bases. The bottom side of the integrated device carries an integrated detector 120*a*, such as a CCD camera, for detecting the scattered light from the ZMW. One will appreciate, therefore, that conventional optical components (e.g. objectives, lenses, mirrors, wedges) are not needed for detection.

One will appreciate from the description herein that the materials and configuration of the device may vary. Other metals or alloys can serve as a base substrate for the particles. The high index of refraction substrate can be different materials, glasses, polymers and the like. The high refraction index material can span the entire substrate or can be a thin layer on a carrier substrate configured as a waveguide. The top layer can be other materials, such as polymers or different glasses, or composite materials. The device can also be a multilayered structure, e.g., glass with an alumina coating. A thin layer can be placed between the core and cladding, e.g., a glass layer to enable surface chemistries.

Detection using the device shown in FIG. 25 may be carried out by directing different wavelengths to influence the scattering characteristics of different nanoparticle materials. A white light source (e.g. xenon lamp), which would enable spectral detection, can be used. In an exemplary embodiment, various input wavelengths are gated in time, and the differentiation of detection is based on time-gated detection.

The bottom side of the device can also carry a cladding layer, which can be of the same or different material of the top side, to provide a spacer between the device and the detection array. An optional mask is placed on the bottom surface to minimize crosstalk. In various embodiments, crosstalk is corrected computationally by cross-correlating signals from neighboring ZMWs. If the detector is spaced at some distance from the chip, spacer materials (e.g. solids, fluids, and gases) can be used to improve scattering light radiation efficiencies. In various embodiments, surface morphologies are built into the back side of the chip to enhance the direction of the scattering signals to the detection unit.

Unlike fluorescence detection, the integrated device of FIG. 42 generally reduces problems with respect to signal-to-noise (dye brightness) and photodamage. The device also does not require powerful lasers, sophisticated optics, and expensive detection technologies.

It is to be understood that the above description is intended to be illustrative and not restrictive. It readily should be apparent to one skilled in the art that various embodiments and modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. In describing the invention herein, references to any element in the singular will include references to plural, and vice versa, unless it is clear from the context that this was explicitly not intended. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated herein by reference in its entirety for all purposes.

What is claimed is:

1. A method for sequencing a nucleic acid comprising: providing an integrated analytical device comprising
an optically opaque cladding layer having a plurality of nanoscale apertures extending through the cladding layer into a transparent substrate below the cladding layer, the nanoscale apertures separated by regions of the substrate from any other nanoscale apertures, wherein the nanoscale apertures each define a reaction cell for receiving a set of sequencing reagents, the sequencing reagents comprising a plurality of fluorescently labeled nucleotides each having a different excitation spectrum;
a waveguide layer below the reaction cells comprising a plurality of waveguides that direct excitation illumination to the reaction cells; and
a detection layer below the waveguide layer comprising a plurality of sensor elements in optical communication with the reaction cells, wherein each reaction cell has at least one sensor element associated with it, wherein each sensor element comprises a pixel having multiple integrated storage elements;
carrying out nucleic acid sequencing reactions in the reaction cells while illuminating the reaction cells with a pulsed excitation light comprising pulses of at least two different excitation wavelengths iteratively over time, wherein each respective excitation wavelength in the at least two different excitation wavelengths of the pulsed excitation light corresponds to the excitation spectrum of a corresponding fluorescently labeled nucleotide in the plurality of fluorescently labeled nucleotides, and the excitation light at each respective excitation wavelength excites the corresponding fluorescently labeled nucleotide to emit a signal;
measuring emitted signals over time from each reaction cell while carrying out the sequencing reactions; and
correlating said emitted signals with the timing of the pulses of the pulsed excitation light to identify the fluorescently labeled nucleotides excited by the excitation light at each respective excitation wavelength in the at least two different excitation wavelengths, thereby sequencing the nucleic acid.

2. The method of claim 1 wherein the plurality of fluorescently labeled nucleotides comprise four fluorescently labeled nucleotides.

3. The method of claim 1 wherein a single sensor element is associated with each reaction cell.

4. The method of claim 1 wherein the pixel has four integrated storage elements.

5. The method of claim 4 wherein each of the storage elements are electronically gated by the activation of a separate excitation source.

6. The method of claim 4 wherein the analytical device further comprises a modulated controller element coupled to both the detector layer and the waveguide layer to synchronize illumination and storage.

7. The method of claim 1 wherein a delay between an excitation event and emission for each label is preprogrammed into the sensor elements.

8. The method of claim 1 wherein the sensor elements comprise a CMOS, NMOS, or PMOS sensors.

9. The method of claim 1 wherein the analytical device comprises between about 1,000,000 and 10,000,000 sensor elements.

10. The method of claim 1 wherein the reaction cells comprise zero mode waveguides.

11. The method of claim 1 wherein the analytical device further comprises a fluidic conduit that extends across multiple reaction cells.

12. The method of claim 1 wherein the analytical device further comprises a transmission layer between the waveguide layer and the detector layer that transmits emitted light from the reaction cells to the detector layer.

13. The method of claim 12 wherein the transmission layer comprises an optical tunnel.

14. The method of claim 12 wherein the transmission layer comprises optical filters.

15. The method of claim 1, wherein each integrated storage element is an integrating node, wherein the integrating nodes are independently reset to clear previous charges from their circuits prior to transfer operations.

* * * * *